US010351903B2

(12) United States Patent
Zhou et al.

(10) Patent No.: US 10,351,903 B2
(45) Date of Patent: Jul. 16, 2019

(54) ALLELE AMPLIFICATION BIAS

(71) Applicant: University of Utah Research Foundation, Salt Lake City, UT (US)

(72) Inventors: Luming Zhou, Salt Lake City, UT (US); Robert Andrew Palais, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 251 days.

(21) Appl. No.: 15/163,624

(22) Filed: May 24, 2016

(65) Prior Publication Data

US 2016/0319336 A1 Nov. 3, 2016

Related U.S. Application Data

(62) Division of application No. 13/128,289, filed as application No. PCT/US2009/063634 on Nov. 6, 2009, now Pat. No. 9,422,597.

(60) Provisional application No. 61/117,371, filed on Nov. 24, 2008, provisional application No. 61/112,495, filed on Nov. 7, 2008.

(51) Int. Cl.
  *C12Q 1/68* (2018.01)
  *C12Q 1/6827* (2018.01)
  *C12Q 1/6886* (2018.01)

(52) U.S. Cl.
  CPC ......... *C12Q 1/6827* (2013.01); *C12Q 1/6886* (2013.01); *C12Q 2600/156* (2013.01)

(58) Field of Classification Search
  None
  See application file for complete search history.

(56) References Cited

U.S. PATENT DOCUMENTS

| 7,297,484 | B2 | 11/2007 | Wittwer et al. |
| 7,387,887 | B2 | 6/2008 | Wittwer et al. |
| 7,582,429 | B2 | 9/2009 | Wittwer et al. |
| 9,422,597 | B2 | 8/2016 | McKinney |
| 2003/0104438 | A1 | 6/2003 | Eyre et al. |
| 2003/0108913 | A1 | 6/2003 | Schouten |
| 2006/0003333 | A1 | 1/2006 | Puskas |
| 2006/0019253 | A1 | 1/2006 | Wittwer et al. |
| 2007/0020656 | A1* | 1/2007 | Sorge ................. C12Q 1/6816 435/6.11 |
| 2008/0193934 | A1 | 8/2008 | Wangh |
| 2009/0222503 | A1 | 9/2009 | Palais et al. |

FOREIGN PATENT DOCUMENTS

| CA | 2680121 | 9/2008 |
| CN | 1934270 | 3/2007 |
| EP | 1580269 | 9/2005 |
| EP | 2031074 | 4/2009 |
| WO | WO9745559 | 12/1997 |
| WO | WO2004038038 | 5/2004 |
| WO | WO2006110735 | 10/2006 |
| WO | WO2007035806 | 3/2007 |
| WO | WO2007106534 | 9/2007 |
| WO | WO2007106899 | 9/2007 |
| WO | WO2008109823 | 9/2008 |
| WO | WO2010054254 | 5/2010 |

OTHER PUBLICATIONS

Seyama et al. (Nucleic Acids Research, 1992, 20(10): 2493-2496) (Year: 1992).*
Wilton et al. (Human Mutation, 1998, 11:252-258). (Year: 1998).*
Zhou et al. (Clinical Chemistry, 2008, 54:10, p. 1648-1656) (Year: 2008).*
Cha, Rita S., et al., "Mismatch Amplification Mutation Assay (MAMA): Application to the c-H-ras Gene," *Genome Research; Cold Spring Harbor Laboratory*, vol. 2, pp. 14-20 (1992).
Dabritz, J., et al., "Detection of Ki-ras Mutations in Tissue and Plasma Samples of Patients with Pancreatic Cancer Using PNA-Medicated {CR Clamping and Hybridisation Probes," *British Journal of Cancer*, 2005, vol. 92, pp. 405-412.
Dominguez, Patrick L., et al. "Wild-Type Blocking Polymerase Chain Reaction for Detection of Single Nucleotide Minority Mutations From Clinical Specimens," *Department of Medicine, Division of Dermatology*, Oncogene, Oct. 13, 2005, vol. 24, No. 45, pp. 6830-6834.
Easterday, William R., et al., "Specific Detection of Bacillus Anthracis Using a TaqMan Mismatch Amplification Mutation Assay," *BioTechniques*, vol. 38, No. 5, (2005), pp. 731-735.
European Search Report for EP09825516 dated Jan. 11, 2013.
Gibbs, Richard, et al., "Detection of Single DNA Base Differences by Competitive Oligonucleotide Priming," *Nucleic Acids Research*, vol. 17, No. 7, (1989).
Gundry et al., "Base-Pair Neutral Homozygotes can be Discriminated by Calibrated High-Resolution Melting of Small Amplicons," Nucleic Acids Research, 2008, 36:10, pp. 3401-3408.
Harteveld, Cornelis L. et al., "Prenatal Diagnosis of Hemoglobin Disorders: Present and Future Strategies, Clinical Biochemistry 42," 2009, pp. 1767-1779, available online at www.sciencedirect.com.
International Search Report and Written Opinion for PCT/US09/63634 dated Mar. 26, 2010.
Jeong, S, et al. "Accurate Auantitation of Allele-Specific Expression Patterns by Analysis of DNA Melting," *Genome Research*, published online Jun. 1, 2007, vol. 17, pp. 1095-1100.
Li, Baohui, et al., "Genotyping With TaqMAMA," *Genomics* 83 (2004), pp. 311-320, available online at www.sciencedirect.com.
Li, Jin, et al. "Replacing PCR with COLD-PCR Enriches Variant DNA Sequences and Redefines the Sensitivity of Genetic Testing," *Nature Medicine*, vol. 14, No. 5, (2008), pp. 579-584.

(Continued)

*Primary Examiner* — Stephanie K Mummert
(74) *Attorney, Agent, or Firm* — Workman Nydegger

(57) ABSTRACT

Methods are provided for nucleic acid analysis. In an illustrative method, allele amplification bias is used to amplify preferentially a target nucleic acid that is present in a low allele fraction.

10 Claims, 62 Drawing Sheets
Specification includes a Sequence Listing.

(56) References Cited

OTHER PUBLICATIONS

Liew et al., "Genotyping of Single-Nucleotide Polymorphisms by High-Resolution Melting of Small Amplicons," Clinical Chemistry, 2004, 50:7, pp. 1156-1164.
Luo, Ji-Dung, et al., "Detection of Rare Mutant K-ras DNA in a Single-Tube Reaction Using Peptide Nucleic Acid as Both PCR Clamp and Sensor Probe," *Nucleic Acids Reseasrch*, 2006, vol. 34, pp. 1-7.
Newton, C.R., et al. Analysis of Any Point Mutation in DNA: The Amplification Refractory Mutation System (ARMS), *Nulceic Acids Research*, vol. 17, No. 7 (1989).
Nielsen, Peter E., et al., "Sequence-Selective Recognition of DNA by Strand Displacement with a Thymine-Substituted Polyamide," *Science*, vol. 254 (1991), pp. 1497-1500.
Orou, Andreas, et al., "Allele-Specific Competitive Blocker PCR: A One-Step Method With Applicability to Pool Screening," *Human Mutation*, vol. 6, pp. 163-169 (1995).
Palais et al., "Chapter 13: Mathematical Algorithms for High-Resolution DNA Melting Analysis," Methods of Enzymology, 2009, 454:323-43.
Rand, Keith N. et al., "Headloop Supression PCR and Its Application to Selective Amplification of Methylated DNA Sequences," *Nucleic Acids Research*, 2005, vol. 33, No. 14.
Rowe et al., "Utility of BRAF V600E Mutation Detection in Cytologically Indeterminate Thyroid Nodules," CytoJournal, 2006, 3:10.
Seyama et al., "A Novel Blocker-PCR Method for Detection of Rare Mutant Alleles in the Presence of an Excess Amount of Normal DNA," Nucleic Acids Research, vol. 20, No. 10, p. 2493-2496.
Snell et al., "BRCA 1 Promoter Methylation in Peripheral Blood DNA of Mutation Negative Familial Breast Cancer Patients with a BRCA1 Tumour Phenotype," Breast Cancer Research, 2008, 10:R12.
Soltar, et al., "One-Step Detection of c-kit Point Mutations Using Peptide Nucleic Acid-Mediated Polymerase Chain Reaction Clamping and Hybridization Probes," *American Journal of Pathology*, vol. 162, No. 3, Mar. 2003, pp. 737-746.
Tan, Angela Y.C. PhD., et al., "A Simple, Rapid, and Sensitive Method for the Detection of the JAK2 V617F Mutation," *American Society for Clinical Pathology*, vol. 127, (2007) pp. 977-981.
Tan, Angela, et al. "Sensitive Detection of KIT D816V in Patients With Mastocytosis," *Clinical Chemistry*, vol. 52, No. 12 (2006) pp. 225-2257.
Wang et al., "High-Throughput SNP Genotyping by Single-Tube PCR with Tm-Shift Primers," BioTechniques, 2005, 39:6, p. 885-893.
Whitcombe, David, et al. "Detection of PCR Products Using Self-Probing Amplicons and Fluorescence," *Nature Biotechnology*, vol. 17, Aug. 1999, pp. 804-807.
Willmore-Payne, et al., "The Use of EGFR Exon 19 and 21 Unlabeled DNA Probes to Screen for Activating Mutations in Non-Small Cell Lung Cancer," Journal of Biomolecular Techniques, 2008, 19:217-224.
Wilton, Steve D., et al., "Snapback SSCP Analysis: Engineered Conformation Changes for the Rapid Typing of Known Mutations," *Human Mutation*, 1998, vol. 11, pp. 252-258.
Yu, Dan, et al. "Specific Inhibition of PCR by Non-Extendable Oligonucleotides Using a 5' to 3' Exonuclease-Deficient DNA Polymerase," *BioTechniques*, vol. 23, No. 4 (1997) pp. 714-720.
Zhou et al., "Enrichment and Detection of Rare Alleles by Means of Snapback Primers and Rapid-Cycle PCR," Clinical Chemistry, 2010, 56:5, pp. 814-822.
Zhou et al., "Snapback Primer Genotyping with Saturating DNA Dye and Melting Analysis," Clinical Chemistry, 2008, 54:10, pp. 1648-1656.
U.S. Appl. No. 13/128,289, dated Nov. 4, 2013, Office Action.
U.S. Appl. No. 13/128,289, dated Aug. 18, 2014, Final Office Action.
U.S. Appl. No. 13/128,289, dated Sep. 10, 2015, Office Action.
U.S. Appl. No. 13/128,289, dated May 5, 2016, Notice of Allowance.

* cited by examiner

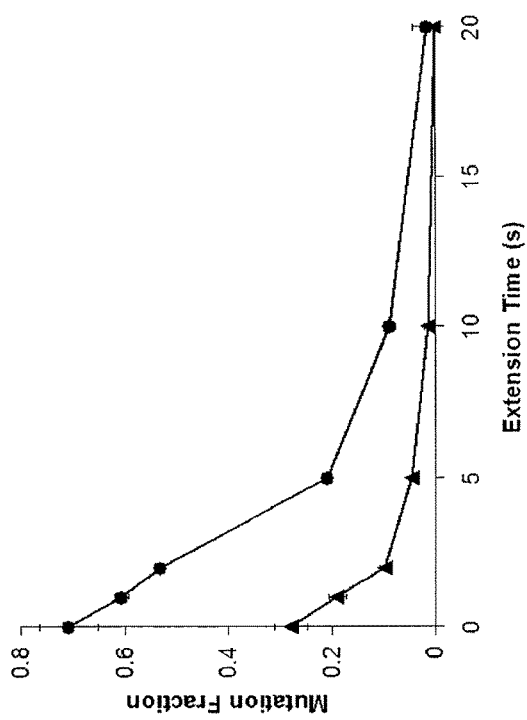
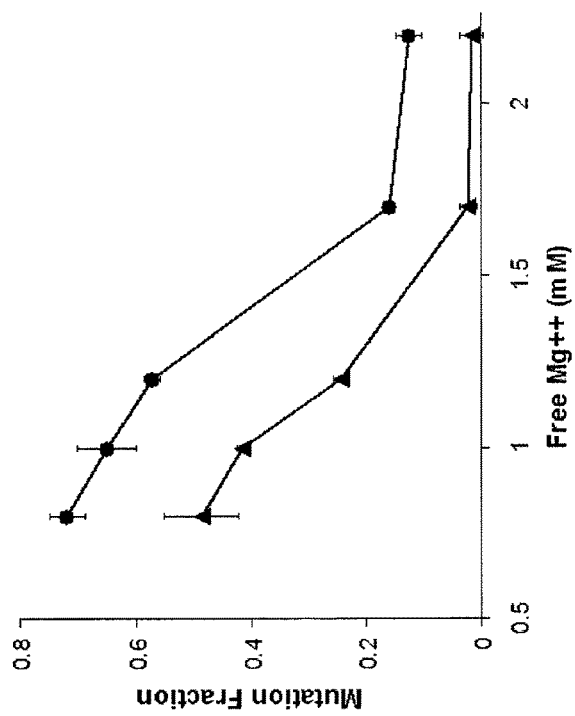
Fig. 26a
Fig. 26b

```
                              SEQUENCE LISTING

<160> NUMBER OF SEQ ID NOS: 16

<210> SEQ ID NO 1
<211> LENGTH: 24
<212> TYPE: DNA
<213> ORGANISM: Plasmodium falciparum

<400> SEQUENCE: 1
ttcttgtctt ggtaaatgtg ctca                                              24

<210> SEQ ID NO 2
<211> LENGTH: 28
<212> TYPE: DNA
<213> ORGANISM: Plasmodium falciparum

<400> SEQUENCE: 2
cggatgttac aaaactatag ttaccaat                                          28

<210> SEQ ID NO 3
<211> LENGTH: 28
<212> TYPE: DNA
<213> ORGANISM: Plasmodium falciparum
<220> FEATURE:
<221> NAME/KEY: mutation
<222> LOCATION: (6)..(6)
<223> OTHER INFORMATION: SNP site
<220> FEATURE:
<221> NAME/KEY: mutation
<222> LOCATION: (14)..(14)
<223> OTHER INFORMATION: SNP site
<220> FEATURE:
<221> NAME/KEY: mutation
<222> LOCATION: (15)..(15)
<223> OTHER INFORMATION: SNP site
<220> FEATURE:
<221> NAME/KEY: mutation
<222> LOCATION: (17)..(17)
<223> OTHER INFORMATION: SNP site
<220> FEATURE:
<221> NAME/KEY: mutation
<222> LOCATION: (19)..(19)
<223> OTHER INFORMATION: SNP site

<400> SEQUENCE: 3
gtgtatgtgt aatgaataaa attttttgc                                         28

<210> SEQ ID NO 4
<211> LENGTH: 20
<212> TYPE: DNA
<213> ORGANISM: Homo sapiens

<400> SEQUENCE: 4
ctactgggac ggaacagctt                                                   20

<210> SEQ ID NO 5
<211> LENGTH: 19
<212> TYPE: DNA
<213> ORGANISM: Homo sapiens

<400> SEQUENCE: 5
gtgaggctcc cctttcttg                                                    19

<210> SEQ ID NO 6
<211> LENGTH: 23
<212> TYPE: DNA
```

```
<213> ORGANISM: Homo sapiens
<220> FEATURE:
<221> NAME/KEY: mutation
<222> LOCATION: (9)..(9)
<223> OTHER INFORMATION: SNP site

<400> SEQUENCE: 6
tgaggtgcgt gtttgtgcct gtc                                           23

<210> SEQ ID NO 7
<211> LENGTH: 23
<212> TYPE: DNA
<213> ORGANISM: Homo sapiens

<400> SEQUENCE: 7
aagacagcca tccaaaatta cac                                           23

<210> SEQ ID NO 8
<211> LENGTH: 23
<212> TYPE: DNA
<213> ORGANISM: Homo sapiens

<400> SEQUENCE: 8
tttgtcacca cctcaccta ctt                                            23

<210> SEQ ID NO 9
<211> LENGTH: 24
<212> TYPE: DNA
<213> ORGANISM: Homo sapiens
<220> FEATURE:
<221> NAME/KEY: mutation
<222> LOCATION: (15)..(15)
<223> OTHER INFORMATION: SNP site

<400> SEQUENCE: 9
gagttccagc ccctgtatta cgtg                                          24

<210> SEQ ID NO 10
<211> LENGTH: 20
<212> TYPE: DNA
<213> ORGANISM: Homo sapiens

<400> SEQUENCE: 10
agctcagaac tgcctggtgt                                               20

<210> SEQ ID NO 11
<211> LENGTH: 46
<212> TYPE: DNA
<213> ORGANISM: Artificial Sequence
<220> FEATURE:
<223> OTHER INFORMATION: Primer and probe elements are both Homo
      sapiens, but combined to produce a new sequence, with a 5'
      mismatch.
<220> FEATURE:
<221> NAME/KEY: misc_feature
<222> LOCATION: (1)..(2)
<223> OTHER INFORMATION: 5' mismatch
<220> FEATURE:
<221> NAME/KEY: misc_feature
<222> LOCATION: (3)..(23)
<223> OTHER INFORMATION: probe element
<220> FEATURE:
<221> NAME/KEY: mutation
<222> LOCATION: (13)..(13)
<223> OTHER INFORMATION: SNP site

<400> SEQUENCE: 11
acgttctttg cagaactggc tggtctctgg gctgtccaca cctgaa                  46
```

```
<210> SEQ ID NO 12
<211> LENGTH: 27
<212> TYPE: DNA
<213> ORGANISM: Homo sapiens

<400> SEQUENCE: 12
tgttttcctt tacttactac acctcag                                              27

<210> SEQ ID NO 13
<211> LENGTH: 50
<212> TYPE: DNA
<213> ORGANISM: Artificial Sequence
<220> FEATURE:
<223> OTHER INFORMATION: Primer and probe elements are both Homo
      sapiens, but combined to produce a new sequence, with a 5'
      mismatch.
<220> FEATURE:
<221> NAME/KEY: misc_feature
<222> LOCATION: (1)..(2)
<223> OTHER INFORMATION: 5' mismatch
<220> FEATURE:
<221> NAME/KEY: misc_feature
<222> LOCATION: (3)..(26)
<223> OTHER INFORMATION: Probe element
<220> FEATURE:
<221> NAME/KEY: mutation
<222> LOCATION: (14)..(14)
<223> OTHER INFORMATION: SNP site

<400> SEQUENCE: 13
aatctagcta cagtgaaatc tcgatgtcag tggaaaaata gcctcaattc                      50

<210> SEQ ID NO 14
<211> LENGTH: 24
<212> TYPE: DNA
<213> ORGANISM: Homo sapiens

<400> SEQUENCE: 14
tcagtggaaa aatagcctca attc                                                 24

<210> SEQ ID NO 15
<211> LENGTH: 20
<212> TYPE: DNA
<213> ORGANISM: Homo sapiens

<400> SEQUENCE: 15
tggatcccag aaggtgagaa                                                      20

<210> SEQ ID NO 16
<211> LENGTH: 45
<212> TYPE: DNA
<213> ORGANISM: Artificial Sequence
<220> FEATURE:
<223> OTHER INFORMATION: Primer and probe elements are both Homo
      sapiens, but combined to produce a new sequence, with a 5'
      mismatch.
<220> FEATURE:
<221> NAME/KEY: misc_feature
<222> LOCATION: (1)..(2)
<223> OTHER INFORMATION: 5' mismatch
<220> FEATURE:
<221> NAME/KEY: misc_feature
<222> LOCATION: (3)..(24)
<223> OTHER INFORMATION: probe element

<400> SEQUENCE: 16
ccagagaagc aacatctccg aaagagcaga aactcacatc gagga                          45
```

ALLELE AMPLIFICATION BIAS

CROSS-REFERENCE TO RELATED APPLICATIONS

This application is a divisional of U.S. patent application Ser. No. 13/128,289, filed Jul. 29, 2011, entitled "Allele Amplification Bias", which application claims priority to and the benefit of PCT Application No. PCT/US2009/063634, filed Nov. 6, 2009, entitled "Allele Amplification Bias", which claims priority to and the benefit of U.S. Provisional Application Nos. 61/117,371, filed Nov. 24, 2008, entitled "Allele Amplification Bias with Snapback Primers", and 61/112,495, filed Nov. 7, 2008, entitled "Allele Amplification Bias". All of the aforementioned applications are incorporated by reference herein in their entirety.

GOVERNMENT LICENSE RIGHTS

This invention was made with government support under Grant Number GM082116 awarded by National Institutes of Health. The government has certain rights in the invention.

BACKGROUND OF THE INVENTION

The human genome project has succeeded in sequencing most regions of human DNA. Work to identify the genes and sequence alterations associated with disease continues at a rapid pace. Linkage studies are used to associate phenotype with genetic markers such as simple sequence repeats or single nucleotide polymorphisms (SNPs) to identify candidate genes. Sequence alterations including SNPs, insertions, and deletions that cause missense, frameshift, or splicing mutations then may be used to pinpoint the gene and the spectrum of responsible mutations.

However, even when the genetic details become known, it is difficult to use this knowledge in routine medical practice, in large part because the methods to analyze DNA are expensive and complex. When costs are significantly lowered and the methods dramatically simplified, it is expected that DNA analysis will become accessible for use in everyday clinical practice for effective disease detection and better treatment. Ideal DNA analysis is rapid, simple, and inexpensive.

When a disease is caused by a limited number of mutations, or when a few sequence alterations constitute a large proportion of the disease cases, direct genotyping is feasible. Traditional methods range from classical restriction digestion of PCR products to closed-tube fluorescent methods. Closed-tube methods of DNA analysis can be simple to perform. Once PCR is initiated, no further reagent additions or separations are necessary. However, when one allele is present in small quantities, that allele may be difficult to detect.

Sequencing is currently the gold standard for identifying sequence variation. Even though costs are decreasing, sequencing is still a complex process that is not rapid, simple, or inexpensive when applied to specific genetic diagnosis or pharmacogenetics. Standard sequencing requires seven steps: 1) amplification by PCR, 2) clean up of the PCR product, 3) addition of cycle sequencing reagents, 4) cycle sequencing for dideoxy termination, 5) clean up of the termination products, 6) separation by electrophoresis, and 7) data analysis. This complexity can be automated and has been in some sequencing centers, but sequencing still remains much more complex than the methods of the present invention. Further, when large or multiple genes are analyzed, often over 90% of the sequenced products come back normal. Moreover, current sequencing methods fail to identify low copy alleles, particularly when the alleles are present in an allele fraction of less than 20%. Identifying the presence of these low-copy alleles is important in a number of settings, illustratively in identifying the presence of certain oncogene mutations or changes in tumor samples or peripheral fluids such as blood. The presence or absence of such alleles can be particularly important for the selection of treatment protocols, illustratively with detection/confirmation of common somatic mutations (p53, EGFR, BRAF) and early identification of mutant bacterial infections (e.g., malaria) where standard therapies are contraindicated. Other examples of low levels of mutant alleles that can be found against a predominantly wild-type background are in mitochondrial DNA and fetal DNA present within maternal circulation. In addition, detection of low levels of epigenetic mutations is desired. For example, it was recently found that BRCA1 promoter methylation between 1 and 10% was associated with breast cancer phenotypes (Snell et. al., 2008, Breast Cancer Research)

PCR-based techniques for enriching the proportion of minority alleles and mutations in a sample are known. When the genotype of the mutation is unknown, COLD-PCR can be used (Li J, et al., Nat Med 2008; 14:579-84). This technique can detect down to a 1:100 ratio of mutant allele to wild type. However, because it is nonspecific and detects any variant that occurs, additional analysis is necessary to identify the products. For enriching known SNPs, some of the most popular techniques are ARMS (Newton C R, et al., Nucleic Acids Res 1989; 17:2503-16), PNA-mediated PCR (Nielsen P E, et al., Science 1991; 254:1497-500; Dabritz J, et al., Br J Cancer 2005; 92:405-12), LNA-mediated WTB-PCR (Dominguez P L, Kolodney M S. Wild-type blocking polymerase chain reaction for detection of single nucleotide minority mutations from clinical specimens. Oncogene 2005; 24:6830-4), MAMA-PCR (Cha R S, et al., PCR Methods Appl 1992; 2:14-20), TaqMAMA (Li B, et al., Genomics 2004; 83:311-20; Easterday W R, et al., Biotechniques 2005; 38:731-5), and SCORPION® primers (Whitcombe D, et al., Nat Biotechnol 1999; 17:804-7). These methods detect mutations by allele specific PCR, noting differences in quantification cycle (ACq) and can detect a 1:1000 ratio of mutant allele to wild type.

High resolution melting was introduced as a homogeneous method of scanning PCR amplicons for heterozygous sequence variants. See, e.g., U.S. Pat. Nos. 7,387,887 and 7,582,429, herein incorporated by reference in their entirety. Based on the use of dsDNA saturating dyes, high resolution melting is capable of detecting SNPs and insertions/deletions in amplicons up to 400 bp at a sensitivity >99%. Since its introduction in 2003, additional applications for high resolution melting have been developed, including genotyping for known sequence variants using small amplicons or unlabeled probes (LUNAPROBES™) Unlabeled probes are blocked on the 3'-end to prevent extension during PCR and may use a dsDNA saturation dye, illustratively LCGREEN® Plus (Idaho Technology, Salt Lake City, Utah), to discriminate the genotype of the allele based on probe melting temperature (Tm). The probe sequence can be designed to match either allele and is based on maximizing the ΔTm between the perfect match and mismatched probe. For more information on the use of unlabeled probes, see U.S. Pat. No. 7,387,887, already incorporated by reference.

It has been found that the probes themselves may be used to bias amplification of low fraction alleles. Examples 1-5 below are presented using unlabeled probes. Examples 6-8 are presented using Snapback primers. With a Snapback primer, the primer comprises a probe element specific for a locus of the target nucleic acid and a template-specific primer region, wherein the probe element is 5' of the template-specific primer region. After amplification, the probe element may hybridize to the locus to form a hairpin in an intramolecular reaction or may hybridize to its complement strand in an intermolecular reaction. Thus, a Snapback primer incorporates the probe element into the same oligonucleotide as the primer. Snapback primers may be labeled, but they are often used unlabeled, in a manner similar to unlabeled probes. See WO 2008/109823 (PCT/US08/56217), incorporated herein in its entirety for a detailed discussion of Snapback primers.

While unlabeled probes and unlabeled Snapback primers are used herein, it is understood that the probes may be labeled as well. When unlabeled probes are used they tend to be somewhat larger than other probes (often 25-30 bp) to generate sufficient fluorescent signal from the dsDNA binding dye, and due to this length they are well suited to bias preferentially the amplification of the mismatched allele. The probe (whether unlabeled probe, Snapback probe element, or other probe) is matched to the higher fraction allele, and "allele amplification bias" is empirically determined by setting the annealing temperature (or extension temperature, if used) of PCR somewhere between the Tm of the perfectly matched and somewhat below the Tm of the mismatched probe, illustratively at the Tm of the lower allele or about half way between the Tms, depending on how much melting peaks for the two alleles overlap. At this mid-Tm annealing temperature, the perfectly matched probe is bound to its target (often the wild type allele) and is stable enough to retard amplification. In one embodiment, rapid cycle PCR performed on the LIGHTSCANNER® 32 ("LS32", Idaho Technology, Inc.) was used to aid the stringency of the target annealing temperature and hinder amplification of the wild type allele, although it is understood that other instruments may be suitable. An exo⁻ polymerase may also be used to avoid probe digestion and aid in biasing amplification of the lower Tm allele.

SUMMARY OF THE INVENTION

Accordingly, allele amplification bias is described herein.

In one aspect of the present invention a method for amplification and allele detection of a biological sample is provided, wherein the biological sample comprises a first allele and a second allele of a target nucleic acid, the first allele being present in a higher concentration than the second allele, comprising the steps of adding a thermostable polymerase, a probe, and a pair of primers configured for amplification of the target nucleic acid to the biological mixture, wherein the probe is configured to hybridize to the target nucleic acid and the probe has a first Tm when hybridized to the first allele and second Tm when hybridized to the second allele, wherein the first Tm is higher than the second Tm, amplifying the target nucleic acid in the biological mixture by thermal cycling between a denaturation temperature and an annealing temperature, wherein the annealing temperature is below the first Tm, and detecting the first allele and the second allele.

In illustrative embodiments, the cycling is performed with a ramp rate of at least 4° C., and more illustratively, at least 6° C. In other illustrative embodiments, the first allele and the second allele are detected using melting curve analysis.

In one illustrative example, the melting curve analysis includes high resolution melting using a saturation dye and an unlabeled probe.

In another illustrative method, amplification and allele detection of a biological sample using Snapback primers is provided, wherein the biological sample comprises a first allele and a second allele of a target nucleic acid, the first allele being present in a higher concentration than the second allele, comprising adding a thermostable polymerase, a first primer and a second primer to the biological sample, the primers configured for amplifying the target nucleic acid, wherein the first primer comprises a probe element specific for a locus of the target nucleic acid and a template-specific primer region, wherein the probe element is 5' of the template-specific primer region, wherein the probe element is configured to hybridize to the target nucleic acid and the probe element has a first Tm when hybridized to the first allele and second Tm when hybridized to the second allele, wherein the first Tm is higher than the second Tm, amplifying the target nucleic acid in the biological mixture by thermal cycling between a denaturation temperature and an annealing temperature, wherein the annealing temperature is below the first Tm, and detecting the first allele and the second allele.

In still another embodiment, kits are provided for the methods described herein. The kits comprise the primers, an additional probe element (either as part of a Snapback primer or as a separate probe), and may contain one or more of a polymerase, dNTPs, fluorescent dye, and PCR buffers.

In yet another embodiment, methods are provided for determining allele fractions.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 5a shows the entire derivative melting curve, FIG. 5b shows normalized probe melting peaks, and FIG. 5c shows amplification curves displaying variation based on annealing temperature only, and not on differential probe:target stability.

FIG. 6a shows the entire derivative melting curve, FIG. 6b shows probe normalized melting peaks, and FIG. 6c shows amplification curves.

FIG. 20a shows melting of the probe element, while FIG. 20b shows the whole amplicon melting.

FIG. 21a shows melting of the probe element, while FIG. 21b shows the whole amplicon melting.

FIGS. 26a-b show the effect of extension time (FIG. 26a) and $Mg^{++}$ concentration (FIG. 26b) on allele enrichment using a 5'-exonuclease negative polymerase and snapback primer PCR. Minor allele ratios were either 1:100 (circles) or 1:1000 (triangles). In FIG. 26a, the wild type probe Tm is 75° C. and therefore an extension temperature of 70° C. was chosen, with extension times varying between 0 and 20 s at a free $Mg^{++}$ concentration of 1.2 mM. In FIG. 26b, the free $Mg^{++}$ concentrations used were 0.8 mM, 1 mM, 1.2 mM, 1.7 mM, and 2.2 mM with wild type probe Tm's of 73° C., 74° C., 75° C., 76° C., and 77° C. respectively with an extension temperature of 70° C. for 0 s. The shorter the extension time and the lower the $Mg^{++}$ concentration, the higher the mutant allele fractions obtained. Experiments were performed in triplicate and standard deviations are indicated.

DETAILED DESCRIPTION

Figure 1:
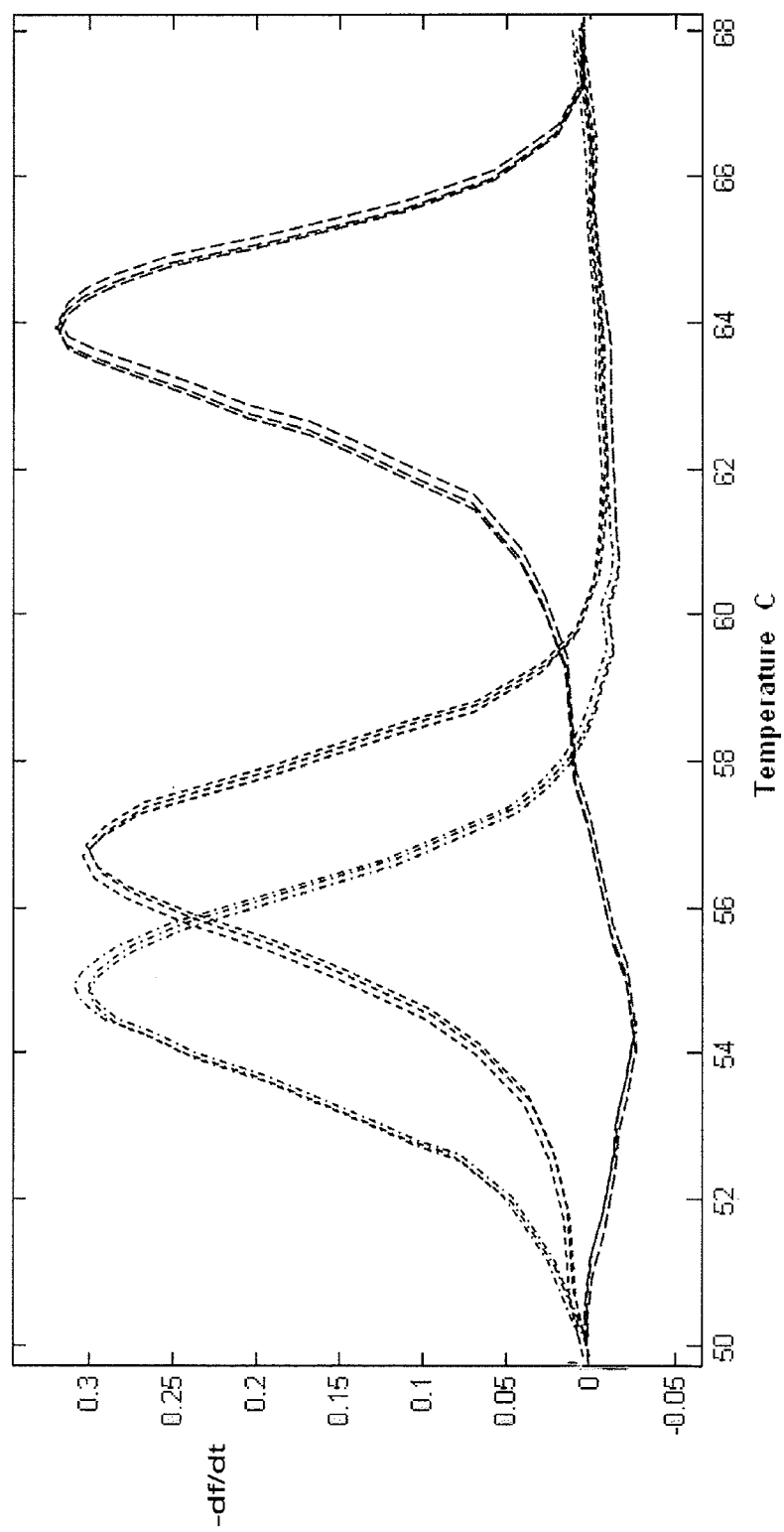
FIG. 1 shows results are from an unlabeled probe genotyping assay (in triplicate) of the malaria P. falciparum CRT gene. The (– – – –) sample is wild type (3D7), the (------) sample is mutant (7G8), and (– ·· – ·· –) show three different mutant samples (FCR3).

Detection sensitivity of a mutant allele without allele amplification bias was previously determined to be about 5% (Wall, M, et al., American Society of Human Genetics, 2007). This work involved use of an unlabeled probe and high resolution melting on the LIGHTSCANNER plate-based instrument (Idaho Technology, Salt Lake City, Utah). Several common polymorphisms were chosen as targets and unlabeled probe assays developed to ascertain the genotype of several random DNA samples. For each locus, 3 samples were chosen representing each of the possible genotypes. The two samples representing the homozygous forms of the genotype were quantified and mixed at the following ratios: 95:5, 90:10, 75:25, 50:50, 25:75, 10:90, and 5:95. Melting profiles of the unlabeled probes were converted to derivative peaks and the peak heights at each melting temperature of the probe were calculated. In this work, discrimination of allele fraction down to 5% for both alleles was possible. However, it has been difficult to discriminate alleles at fractions below 5%.

The LIGHTSCANNER 32 (LS32) is a new hybrid instrument integrating rapid PCR, real-time monitoring, and high resolution melting. PCR and analysis by melt profiling is performed seamlessly in the same instrument. Melt profiling with a saturating dsDNA-binding dye, illustratively LCGREEN Plus, identifies sequence variations in fragments, illustratively from 40-1000 bp. Furthermore, site-specific genotyping may also be performed, illustratively using LCGREEN dye and unmodified oligonucleotide probes or Snapback primers (see WO 2008/109823, herein incorporated by reference in its entirety). Other probe systems may be used as well, such as SIMPLEPROBE, TAQMAN, HYBPROBE, and other probe systems as are known in the art. Other illustrative probe systems include PNA, LNA, or any synthetic base analog-containing probes, biotin-labeled, or any hybridizing protein/nucleic acid or macromolecule or structure that is sequence-dependent and specific in its affinity to template strand such that there is a Tm difference between the alleles. Further, while longer unlabeled probes have been used in the unlabeled probe examples herein, probes of varying length may be used to provide a suitable difference in the Tm between the two alleles. Amplicon melt profiling and probe-based analysis may be performed concurrently in the same run. The LS32 automates PCR and high resolution melt profiling into a unified walk-away system.

High resolution DNA melting analysis was developed in 2003 (see, e.g. U.S. Pat. Nos. 7,387,887 and 7,583,429, already incorporated by reference). As the name suggests, it is a process that heats DNA and records the signal as the DNA double helix dissociates (or "melts") into two single strands. Exactly how the DNA melts depends on the DNA sequence of the specimen. With the aid of a saturation dye, the difference between samples that differ by a single position in the DNA sequence can be distinguished, even in fragments over 800 bases in length.

High-resolution melting is a powerful genetic analysis technique. The advantages of high-resolution melting include the following:

everything is done in solution (the process requires no physical separation),
the system is closed tube (no contamination risk),
very little added cost beyond the cost of PCR itself (labeled probes may be used, but add substantially to the cost), and
the method is simple (no need for automation, reagent additions, or intermediate purification).

The LS32 integrates high resolution melting with rapid PCR of up to 32 samples, allowing amplification in less than 15 min., followed by automatic high-resolution melting. While other systems are available to do rapid cycling followed by high resolution melting and are contemplated by this disclosure, the LS32 is well suited to the present methods and is used as the illustrative instrument in many of the examples herein.

Example 1. Genotypin Using High Resolution Melting

The malaria *P. falciparum* CRT gene was amplified using the following primers and probe:

```
pfCRT Fwd-
                                    (SEQ ID NO. 1)
5' TTCTTGTCTTGGTAAATGTGCTCA pfCRT Rev-
                                    (SEQ ID NO. 2)
5' CGGATGTTACAAAACTATAGTTACCAAT pfCRT Probe-
                                    (SEQ ID NO. 3)
5' GTGTATGTGTAATGAATAAAATTTTTG-C3 blocker
```

For the probe, the underlined bases are the SNP sites, with the bases shown matched to the wild type. While five SNP sites are shown, only four were used in this study.

Amplification was performed with an initial hold of 30 sec. at 95° C., followed by 55 cycles of 95° C. for 2 sec., 58° C. for 15 sec., with a ramp rate measured at approximately 4 to 6° C./s., on 3D7 (wild type) two mutant strains (7G8 and Dd2) of the malaria *P. falciparum* CRT gene. Subsequent to thermal cycling, the samples were held at 95° C. for 2 sec. and then cooled to 40° C. for 30 sec., with a cooling ramp rate of 10° C./s. Melting was from 45° C. to 88° C., with a 0.3° C./s ramp rate and continuous acquisition. Results of probe melting are shown in FIG. 1 (amplicon melting is not shown). The probe is designed as a perfect match to the wild type allele at each locus (codons 72, 75, and 76). Thus sample 3D7 (– – – –) displays the highest melting peak (Tm) possible with this probe. Sample 7G8 (------) is mismatched under the probe at 72 (TT mismatch) and 76 (CT mismatch). Samples Dd2, V1/S, and FCR3 (-·-·-·-) are all the same genotype (see sequencing results below), and are mismatched to the probe at 75 (GT and AA mismatch, 1$^{st}$ and 3$^{rd}$ bases of codon 75) and 76 (CT mismatch). If a sample were mismatched with the probe at only a single base site, the melting peak would be somewhere between the (------) and (– – – –) peak. If a sample were mismatched at all 4 of these sites, one would expect the melting peak to be lower than the (-·-·-·-) peak.

Example 2. Low Allele Fraction Detection

The malaria *P. falciparum* CRT gene was amplified using the primers and probe described above. Mixtures containing various ratios of the wild type and the 7G8 mutant from above were prepared.

Figure 2:
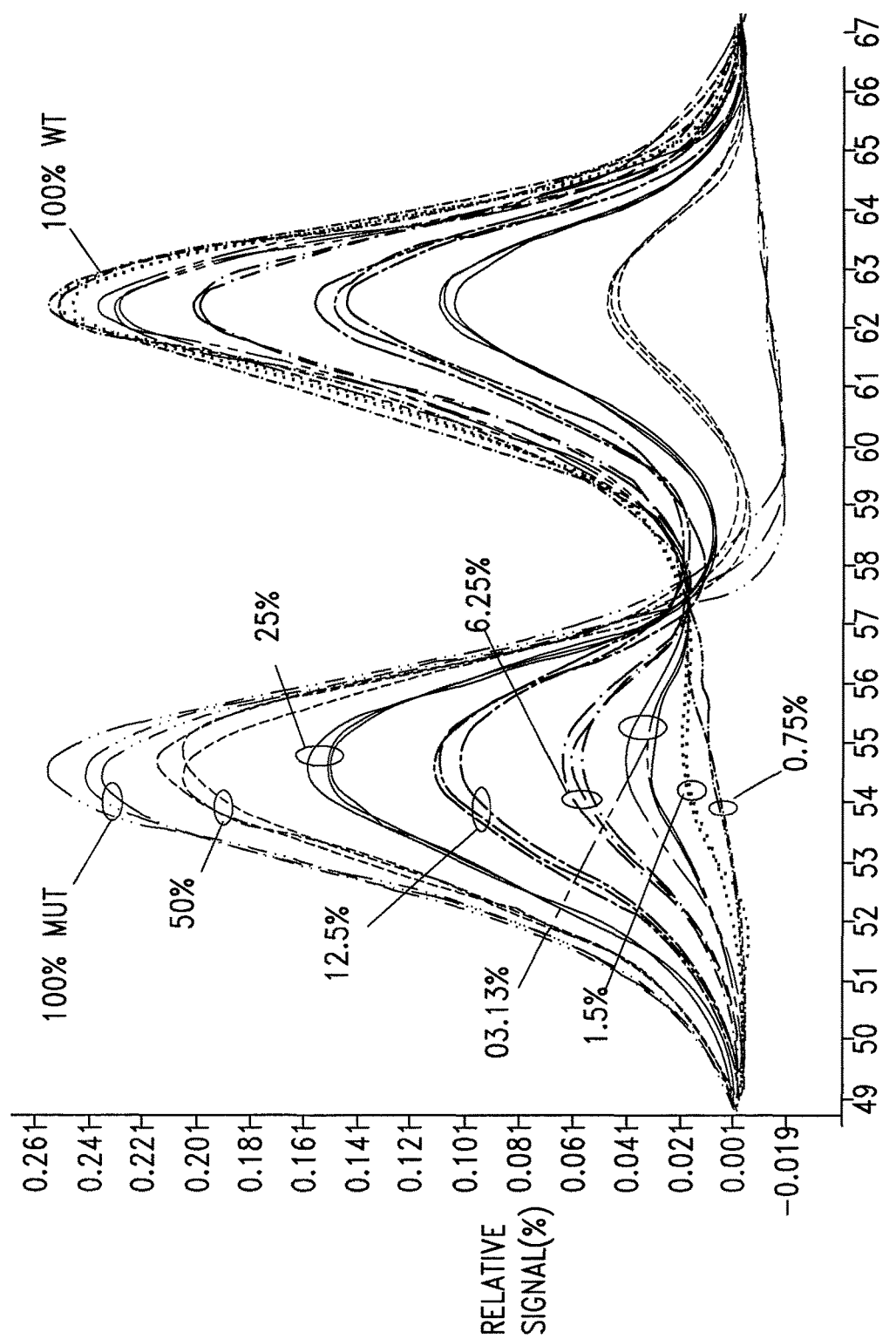
FIG. 2 shows normalized derivative peaks using an unlabelled probe. The wild type allele has a Tm of 62° C. and the mutant allele has a Tm of 54° C. An annealing temperature of 58° C. was used to bias the amplification of the mutant allele in the 50-50 mixed samples. The samples were as follows: (– ·· – ·· –)=100% mutant, (------)=50% mut, (———)=25% mut, (– – – –)=12.5% mut, (– · – · –)=6.25% mut, (– – –)=3.13% mut, (– – – –)=1.5% mut, (– ·· – ·· –)=0.75% mut. This amplification bias allows greater resolution of the mutant allele by a factor of ~10× and sensitivity down to 0.7-1.5%.

Based on observed Tms of the unlabeled probe (62° C. and 54° C. for the wild type and mutant alleles, respectively), an annealing temperature of 58° C. was used (low Tm+½ΔTm) to induce allele amplification bias of the mutant allele in a dilution series of mixed samples. Rapid cycling (ramp rate 6-10° C.) was performed on an LS32, and the results are shown in FIG. 2. This protocol resulted in an allele amplification bias factor of approximately 10×, which permitted discrimination of the mutant allele down to 0.75-1.5%. Further experiments have confirmed this finding, allowing for discrimination down to approximately 0.1%. While an annealing temperature about half way between the two Tms was used, it is understood that any Tm may be used that destabilizes disproportionately the mismatched probe:target, compared with the matched probe:target hybrid. This can occur in a number of situations depending on the relative Tm values of each probe, programmed annealing temperatures, rates of the transitions especially in the 50° C. to 80° C. degree range, and temperature-dependent activity of the polymerase. Illustratively, the annealing temperature is at least 1.0° C. and more illustratively at least 2.0° C. above the lower Tm of the mismatched probe:target hybrid. It has also been found that an annealing temperature at or slightly below that of the probe to the mismatched allele can reduce mismatched probe:target binding sufficiently to provide allele amplification bias. Without being bound to any particular theory, it is expected that the activity of a polymerase is impaired by the bound probe (wild type in this illustrative example), while amplification of the allele having the lower Tm (mutant in this illustrative example) may proceed unimpeded. As shown in Example 4, it is preferred to use ex& polymerases such as KLENTAQ, that is polymerases lacking a 5' to 3' exonuclease activity. However, it is understood that any polymerase may be used that is impeded by the presence of a bound probe. Further, by impeded, it is meant that amplification may occur, but at a reduced efficiency, illustratively reduced by 10% or more, more illustratively reduced by 50% or more of amplification efficiency of the matched allele.

Allele amplification bias was not observed on this target sequence when the same approach to setting the annealing temperature of PCR was performed on a standard thermal block cycler (ramp rate of 1.5 to 2.0° C.). This is presumably due to the slower transition rates between annealing and denaturation temperatures, which would provide additional time for extension at temperatures slightly above the wild type Tm. Thus, a combination of annealing temperature preferentially biasing hybridization of the probe to the dominant allele, a polymerase that is impeded by the presence of the bound probe, and a ramp rate that heats sufficiently quickly, illustratively without a dedicated extension hold (which is often around 72° C.), such that the combination preferentially amplifies the minor allele is desired.

Example 3. Effects of Thermal Cycling Ramp Rate

Figure 3:
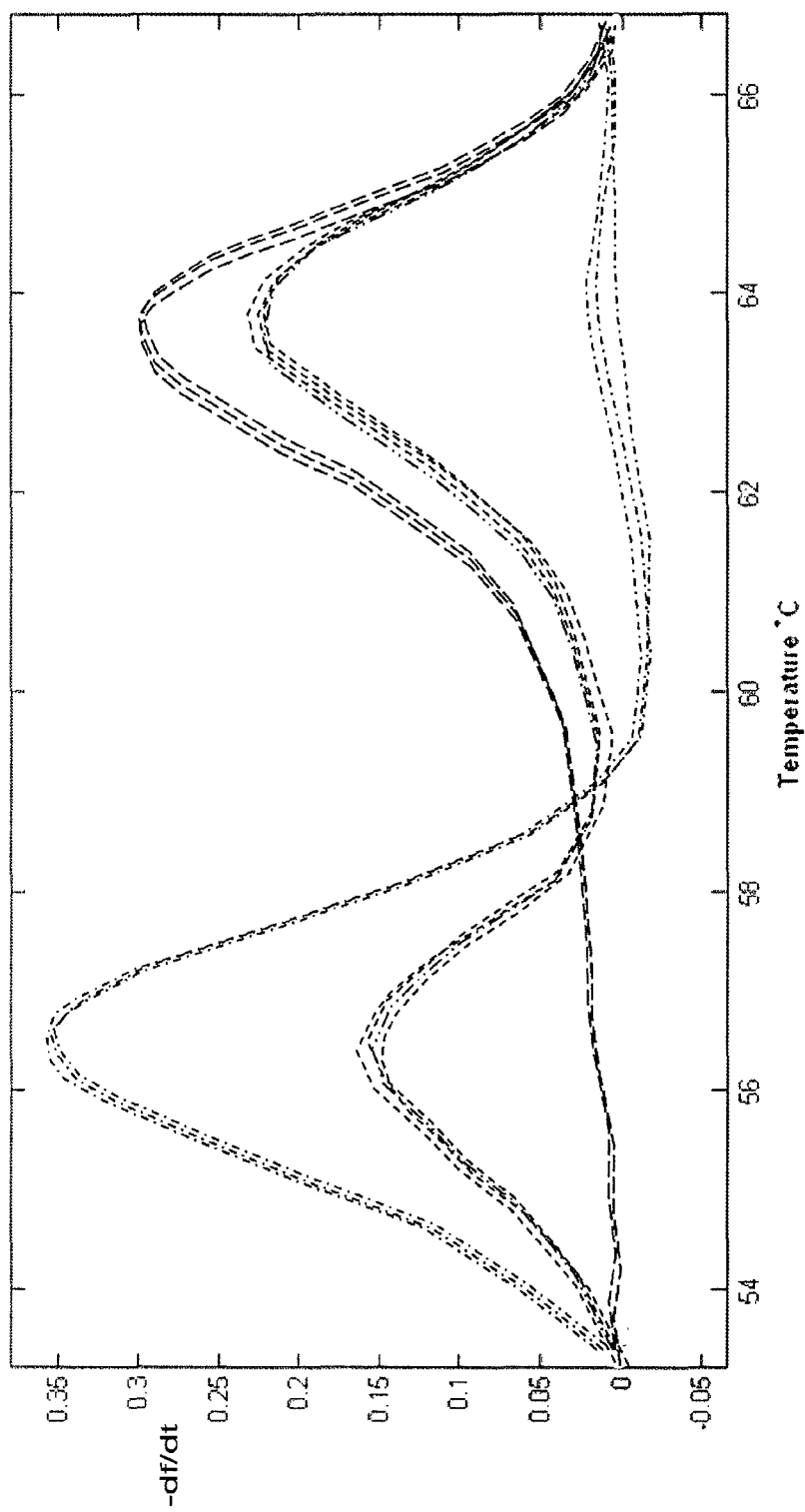
FIG. 3 shows results in which allele amplification bias was unsuccessfully attempted using a slow (1.5-2.0° C./sec) thermal cycler and 8 different annealing temperatures in the same malaria target as that used for FIG. 2 (wild type 3D7 strain (– – – –), mutant 7G8 strain (– ·· – ·· –), and a heterozygote with an equal allele ratio (------)).

A traditional block thermal cycler was used for this example, having a ramp rate of 1.5 to 2.0° C. FIG. 3 shows amplification of malaria CRT gene: wild type 3D7 strain (– – – –), mutant 7G8 strain (-··-··-), and a heterozygote with an equal allele ratio (------), in the presence of an exo⁻ polymerase, with an initial denaturation of a 2 min hold at 95° C., followed by 55 cycles of 94° C. for 30 sec, 30 sec of a programmed gradient annealing step between 50 and 68° C. (50° C., 51.4° C., 53.6° C., 56.8° C., 61.4° C., 64.6° C., 66.8° C., and 68° C.), that is, each sample was cycled using a 94° C. denaturation temperature and one of the various annealing temperatures. FIG. 3 shows no evidence in the heterozygotes of preferential amplification of the lower Tm allele despite eight different annealing temperatures used. Four samples amplified using the 56.8° C. and 61.4° C. (maximal allele amplification bias is predicted to be in this range) annealing temperatures are shown as (–··–) ··–), which is basically indistinguishable from the other heterozygotes.

Further experimentation has shown that a ramp rate 6° C./sec has produced satisfactory results for virtually all assays tested to date. Although individual assays may vary, it is expected that a ramp rate of at least 4° C. should be a sufficient rate for most assays, while many assays may fail to show allele amplification bias with a ramp rate of 2.0° C. or lower. Additionally, it is understood that the cooling ramp rate between the denaturation temperature and the annealing temperature may generate amplification bias depending so long as the primers are sufficiently stable to begin hybridization and the polymerase active to extend at the higher temperatures before reaching the programmed annealing temperature.

Example 4. Low Allele Fraction Detection

Effects of the use of an exo⁺ polymerase (NEB Taq) as compared to the use of an exo⁻ polymerase (Klentaq+ eEnzyme antibody) were studied. A 99 bp fragment of p53 exon 8 was amplified with the following primers and probe:

```
p53x8 FWD:
                                    (SEQ ID NO. 4)
CTACTGGGACGGAACAGCTT p53x8 REV:
                                    (SEQ ID NO. 5)
GTGAGGCTCCCCTTTCTTG p53x8 prb1 PROBE:
                                    (SEQ ID NO. 6)
TGAGGTGCgTGTTTGTGCCTGTC
```

Figure 4A:
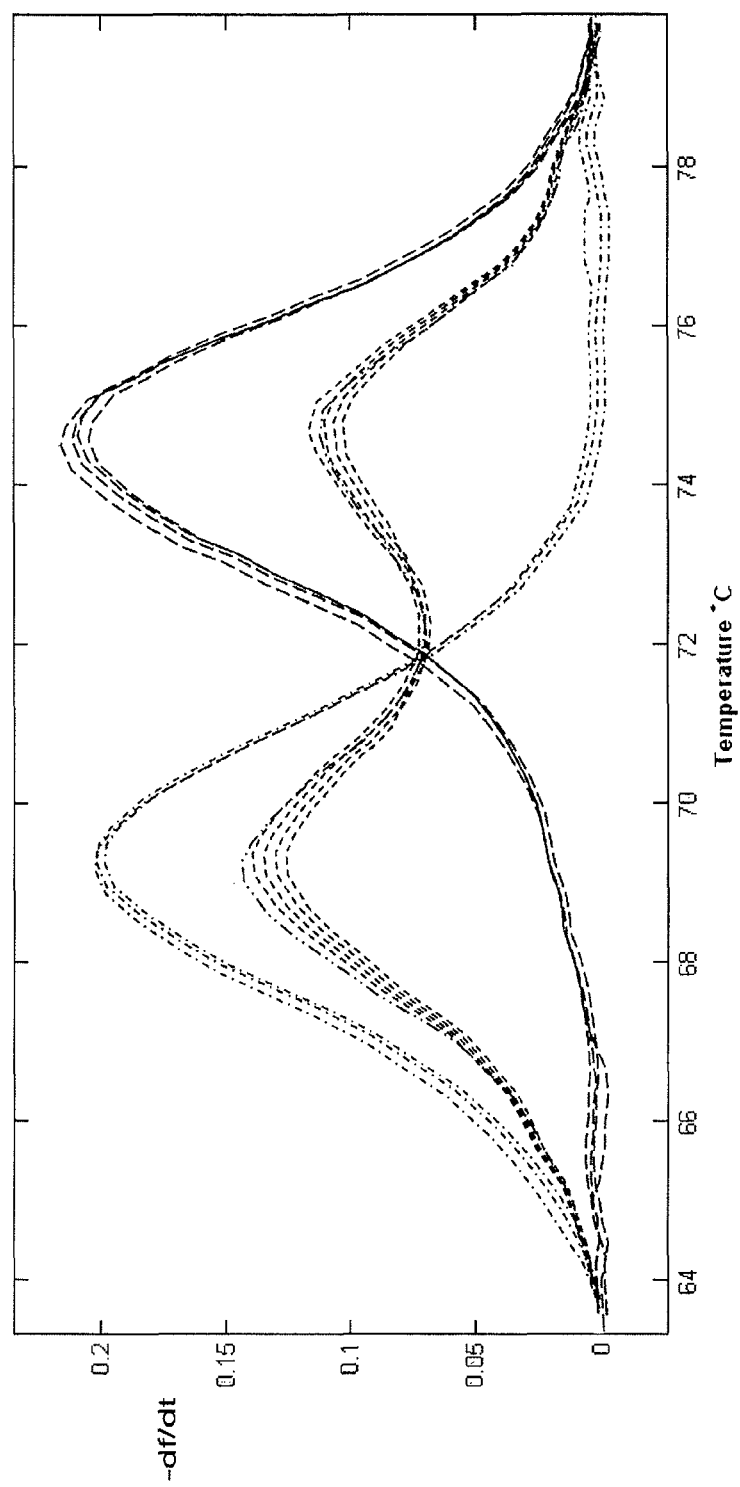
FIGS. 4a-b show unsuccessful and successful results of allele amplification bias using an 8 different annealing temperatures and an exo⁺ polymerase (FIG. 4a) or an exo⁻ polymerase (FIG. 4b), respectively (wild type (– – – –), mutant (– ·· – ·· –), and a heterozygote with an equal allele ratio ((------) at varying annealing temperatures and (—··—··—) at 69° C. annealing temp)).

The probe has a three-carbon spacer at the 3'-end to block extension, and has an observed Tm of about 75° C. A mutant having a mismatch at the 9$^{th}$ base, shown as a lower-case "g" above (G→T), has an observed Tm of about 69° C. FIG. 4a shows amplification of wild type (– – – –), mutant (-··-··-), and a heterozygote with an equal allele ratio (------), in the presence of an exo⁺ polymerase, with an initial denaturation of a 2 min hold at 95° C., followed by 55 cycles of 94° C. for 30 sec, 30 sec at an annealing temperature gradient between 63 and 73° C. (each sample having a slightly different annealing temperature), and 77° C. extension. FIG. 4a shows no evidence in the heterozygotes of preferential amplification of the lower Tm allele despite eight different annealing temperatures used. The (–··–··–) sample had an annealing temperature of 69° C. anneal, which still showed no amplification bias.

Figure 4B:
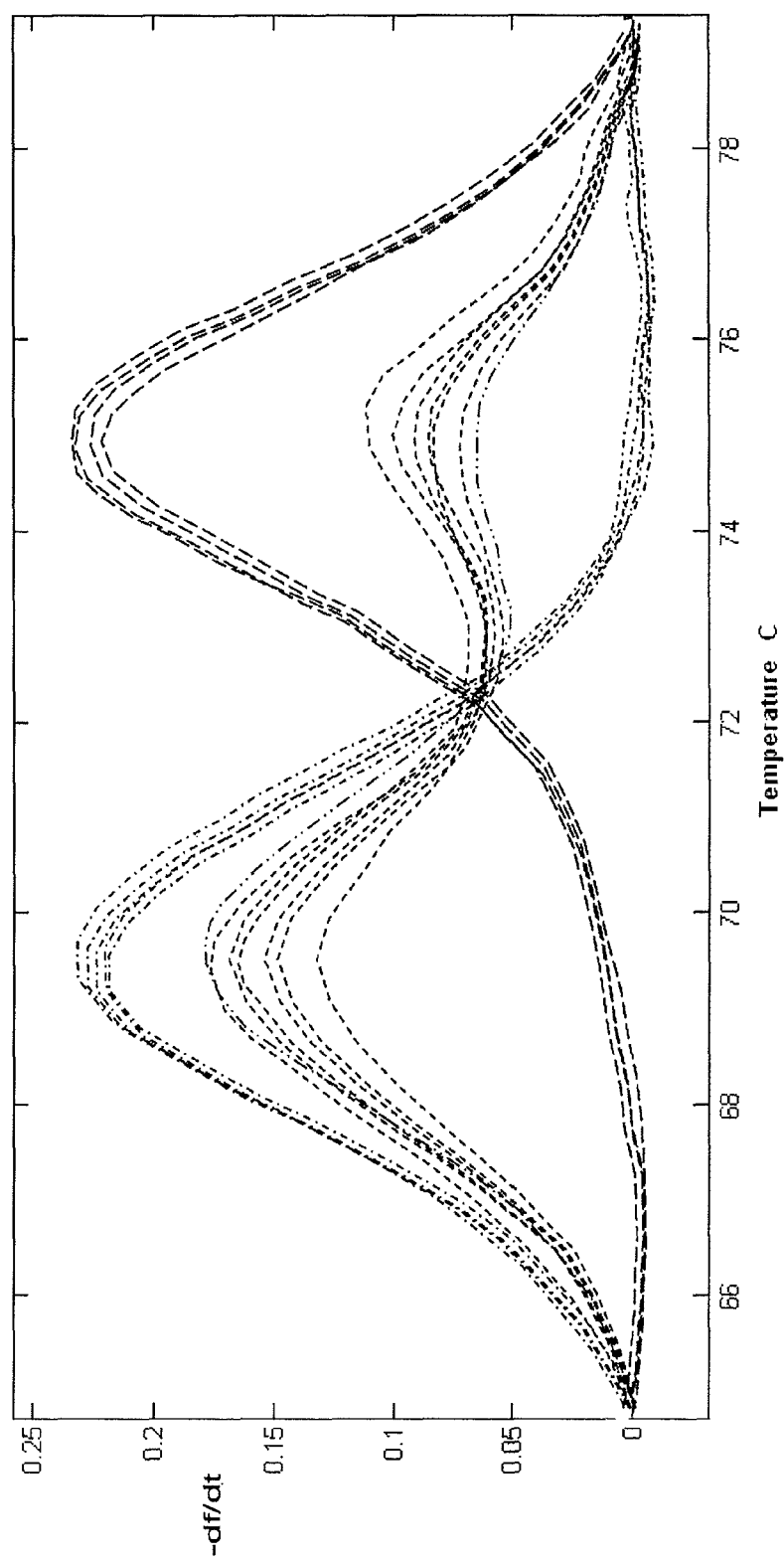

FIG. 4b shows reactions similar to those of FIG. 4a, except using an exo⁻ polymerase. These experiments were set up side-by-side and run on the exact same protocol as those seen in FIG. 4a. As can be seen in FIG. 4b, amplification of the mutant allele is favored. Thus, illustratively an exo⁻ polymerase, or other polymerase that is affected by the hybridization of the probe, is desired. The (–··–··–) sample corresponds to 69° C., which, in this example, provides the best allele amplification bias.

Example 5. Annealing Temperature Analysis

In this example, the effect of annealing temperature is studied. The target used in this example is the human PAH exon 11. Human genomic DNA is used in a concentration of 15 ng/reaction with the following primers and unlabeled probe.

```
Forward primer:
                                    (SEQ ID NO. 7)
AAGACAGCCATCCAAAATTACAC Reverse primer:
                                    (SEQ ID NO. 8)
TTTGTCACCACCTCACCTTACTT Probe:
                                    (SEQ ID NO. 9)
GAGTTCCAGCCCCTgTATTACGTG-C3 blocker
```

Amplification using the above primers results in an amplicon of 105 bp. The G/C SNP rs772897 is indicated in lower case. In all of these examples, the high Tm homozygotes are shown as (-··-··-), the heterozygotes (50:50 mix) are shown as (------) and the low Tm homozygotes are shown as (– – – –).

Figure 5A:
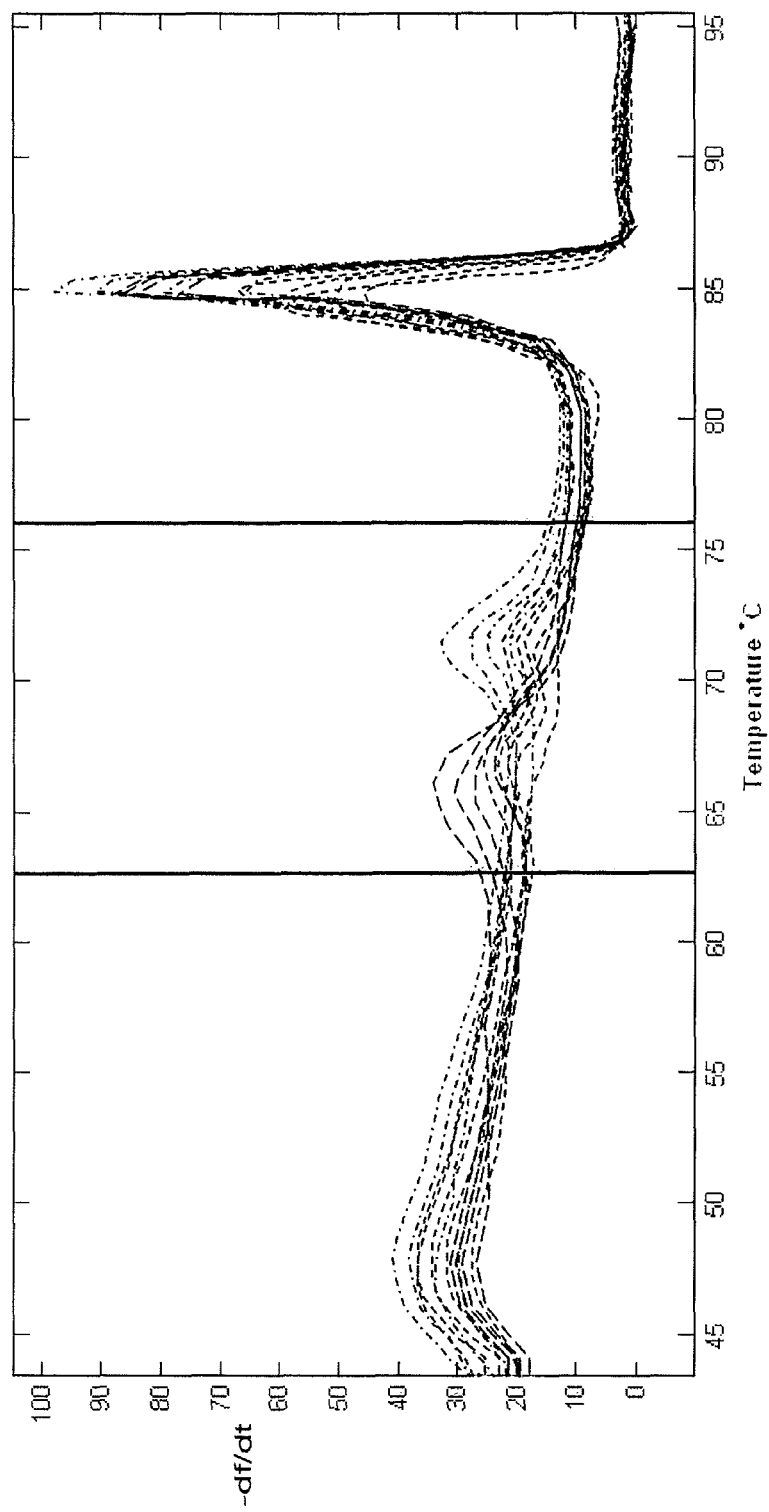
FIGS. 5a-c show result of allele amplification bias method of exon 11 of the PΔH gene using a slow (1.5-2.0° C./sec) thermal cycler and a gradient of annealing temperatures (high Tm homozygotes (—··—··—), heterozygotes (50:50 mix) (------), low Tm homozygotes (— — —))
Figure 5B:
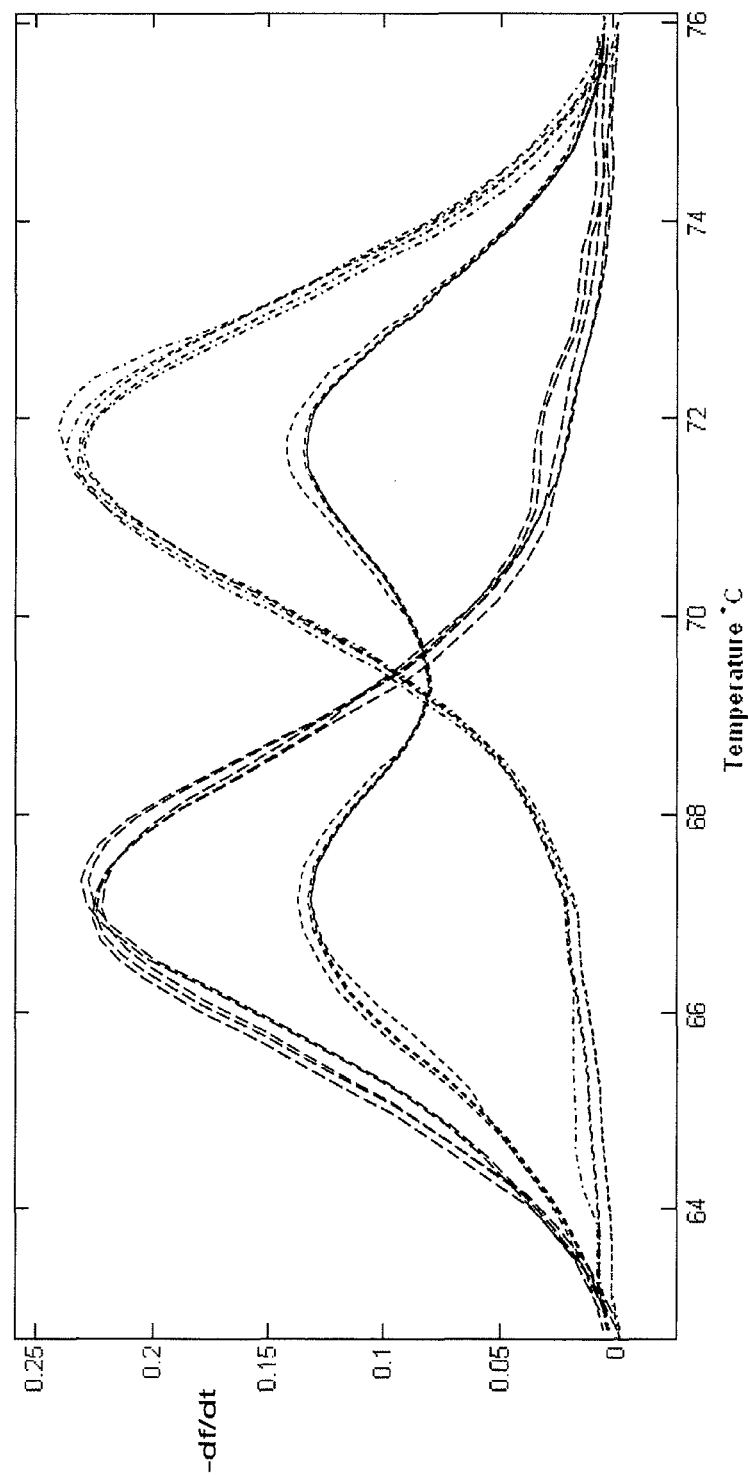
Figure 5C:
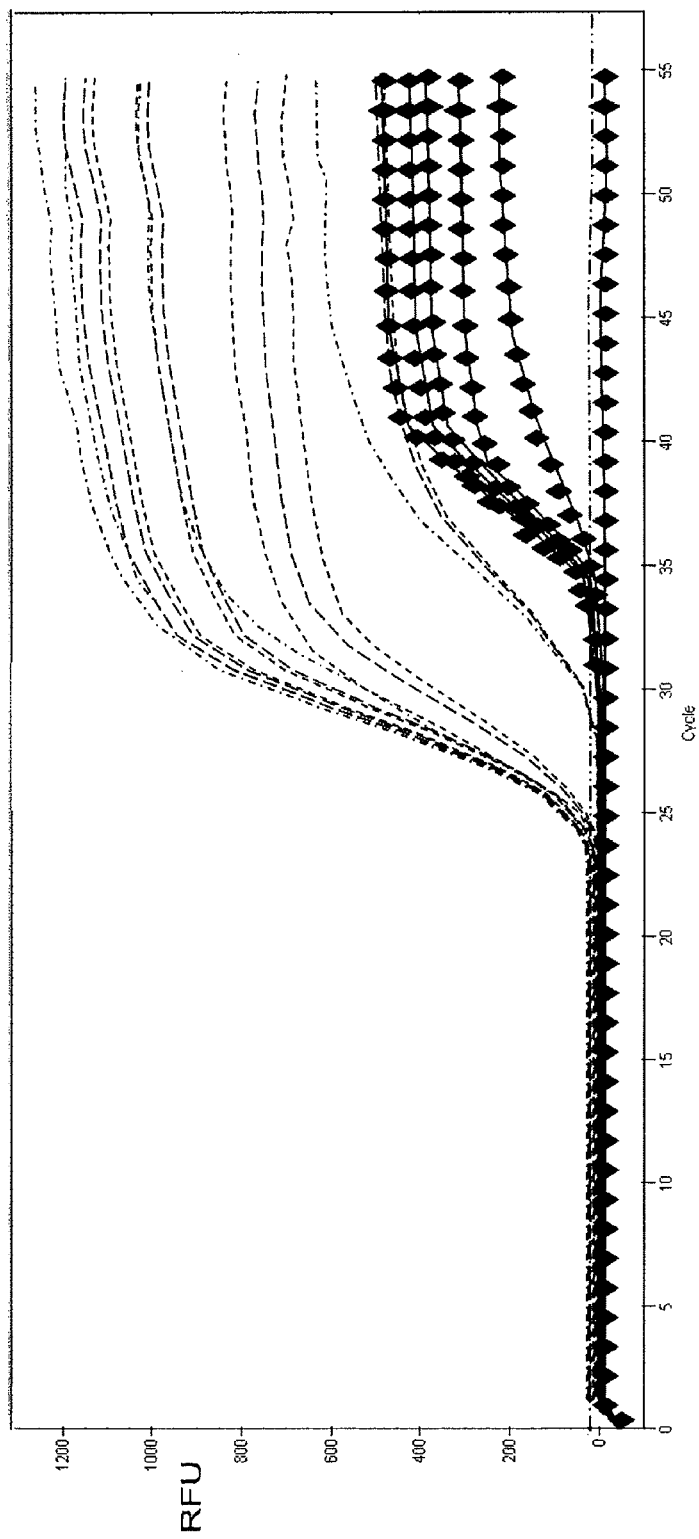

FIGS. 5a-c show the results of amplification on the iCycler (Bio-Rad) with the following cycling conditions:

95° C. for 2 minutes initial denaturation, followed by 55 cycles of 94° C. for 30 sec and X° C. for 30 sec, wherein X is an annealing temperature between 60 and 72° C. in 1° C. increments; that is, each sample was cycled using a 94° C.

denaturation temperature and one of the various annealing temperatures, with a ramp rate of between 1.5 and 2.0° C./sec. After PCR, heteroduplexes are generated by melting at 95° C. for 30 sec, followed by 28° C. for 30 sec. The resulting amplicons were melted on a LIGHTSCANNER melt from 45° C. to 95° C. at standard heating rate. As seen in FIG. 5b, regardless of which annealing temperature is used, the heterozygotes all result in two generally even melting peaks, indicating that there is no bias toward the allele having the lower Tm. As discussed above, it is believed that the ramp rate of 1.5 to 2.0° C./sec may be too slow for some assays, allowing the unlabeled probe to melt off of the higher Tm allele and allowing extension. It is noted that this assay sometimes results in some non-specific amplification, indicated by the negative controls in FIG. 5c (diamonds). The non-specific amplification usually results in a delayed crossing point and lower fluorescence in the amplification curve, as well as a lack of proper melting peaks in the derivative melting curves.

Figure 6A:
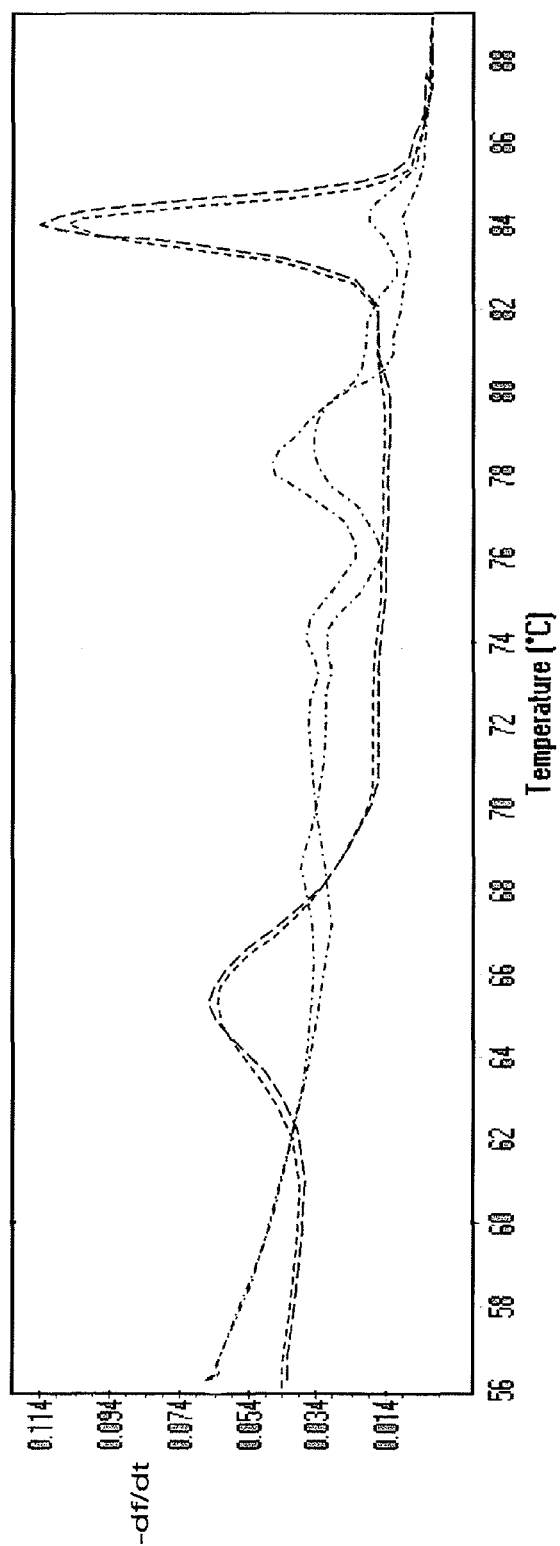
FIGS. 6a-c show amplification of exon 11 of the PΔH gene on a rapid cycling instrument with a 60° C. annealing temperature (high Tm homozygotes (—··—··—), heterozygotes (50:50 mix) (------), low Tm homozygotes (— — —))
Figure 6B:
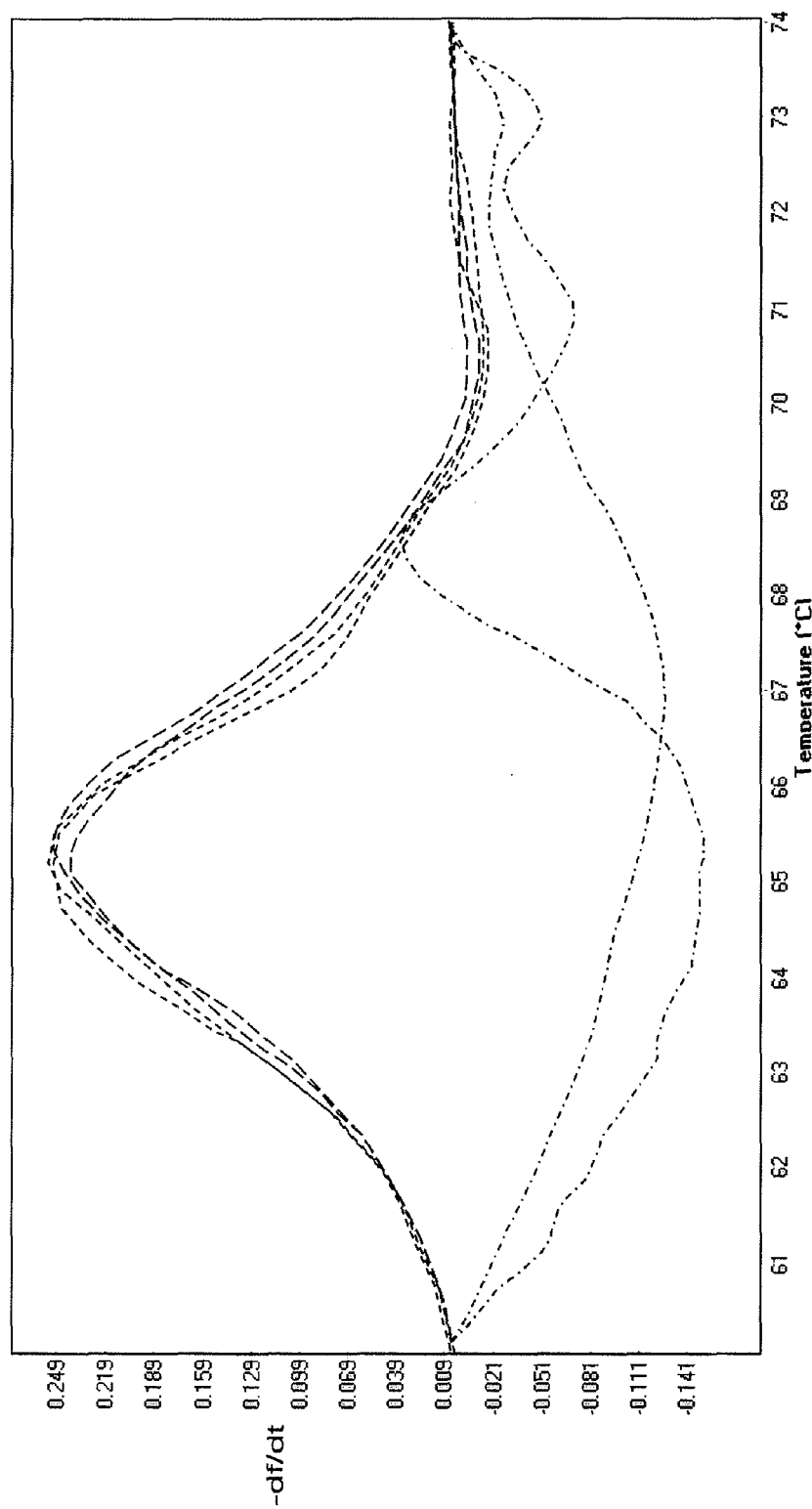
Figure 6C:
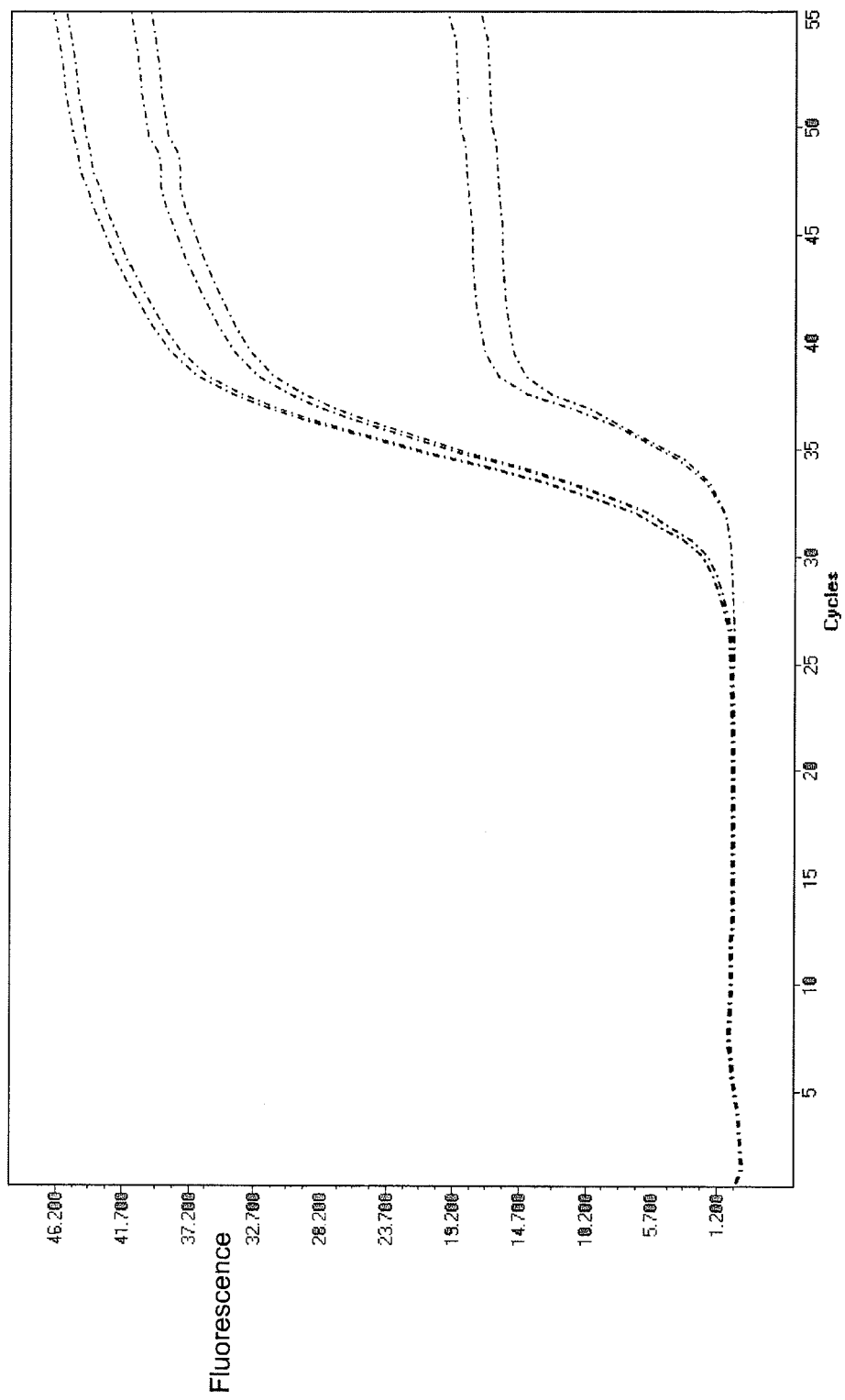

FIGS. 6a-c show the results of rapid cycling amplification at approximately 4-6° C./sec amplification ramp rates of the same target using a 60° C. annealing temperature. The lower Tm allele has an observed Tm of about 67° C., while the higher Tm allele has an observed Tm of about 72° C. Thus, the 60° C. annealing temperature is at the very low end of the lower Tm allele's melting peak and is far below the entire peak of the higher Tm allele. As seen in FIG. 6b, the low Tm homozygotes and the heterozygotes show almost identical melting curves, and the high Tm homozygote shows mostly non-specific amplification, indicating that the lower Tm allele is completely favored, to the elimination of virtually all amplification of the high Tm allele.

Figure 7A:
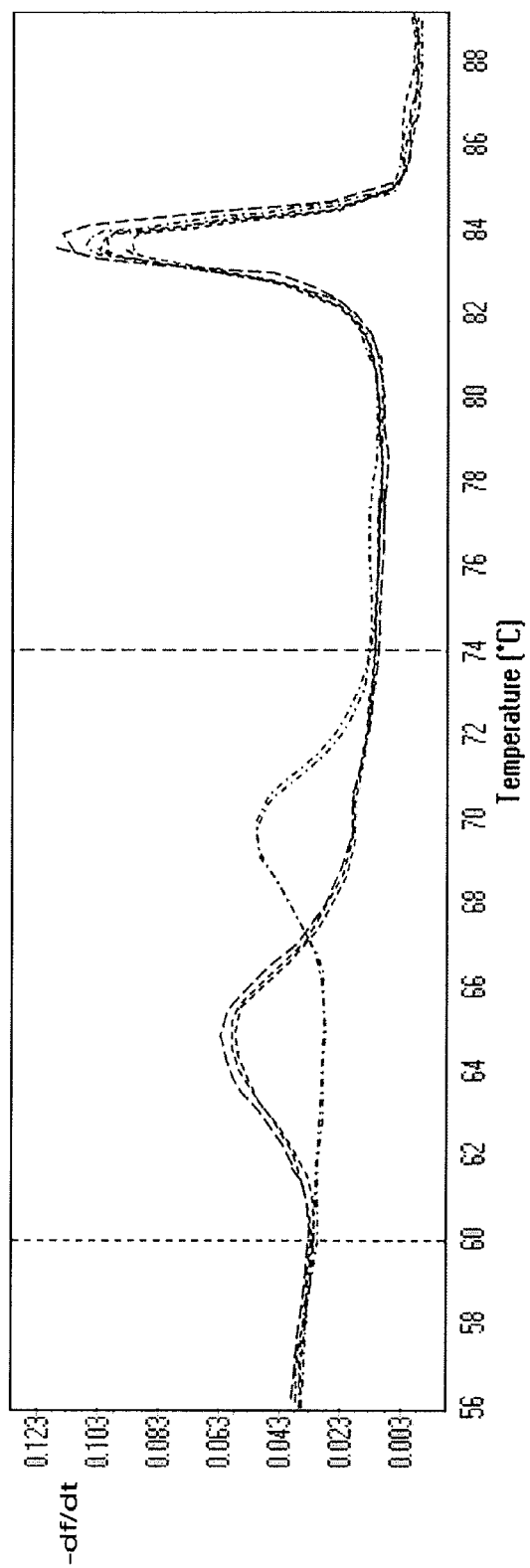
FIGS. 7a-c are similar to FIGS. 6a-c, except that a 62° C. annealing temperature is used.
Figure 7B:
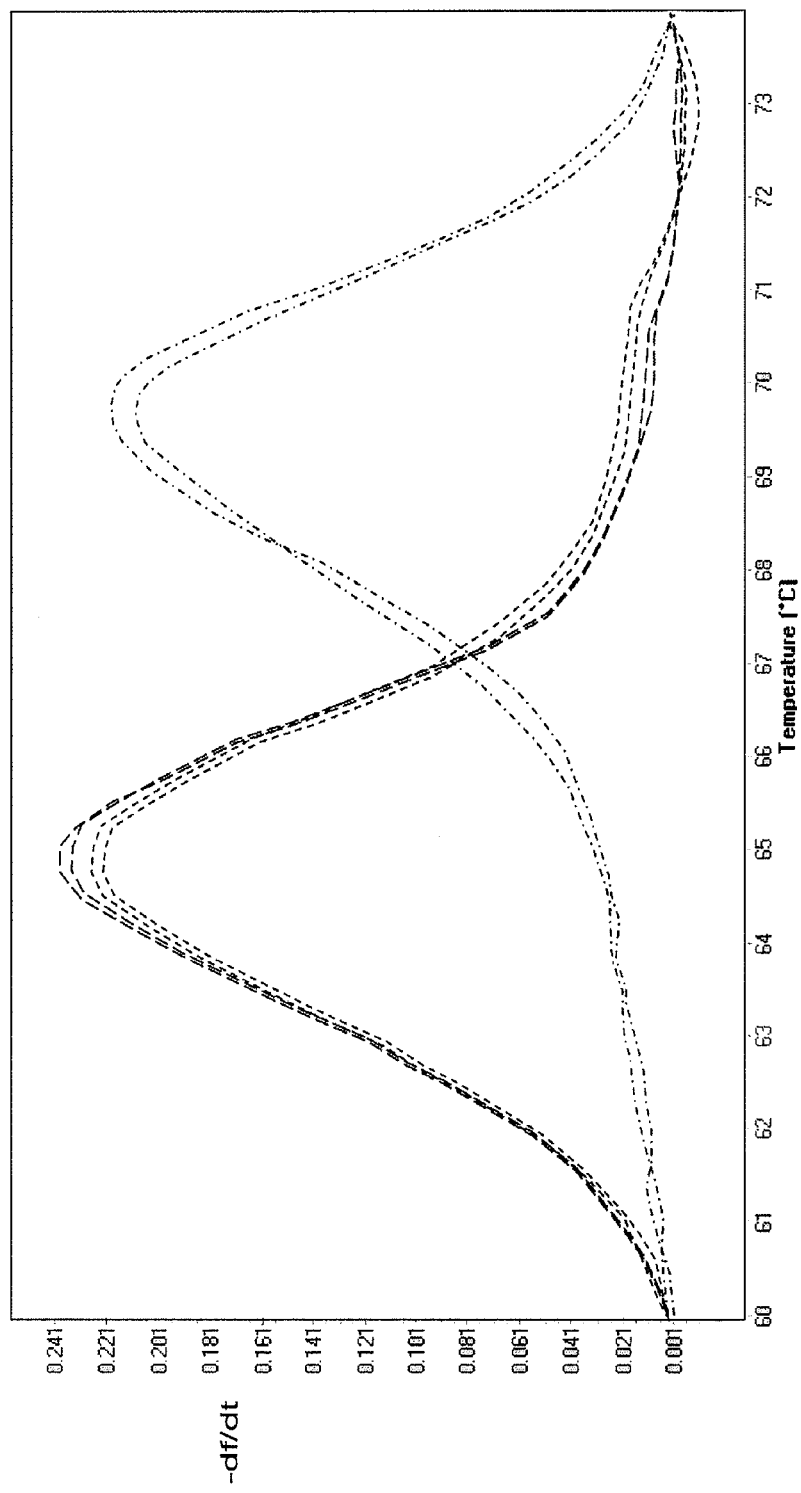
Figure 7C:
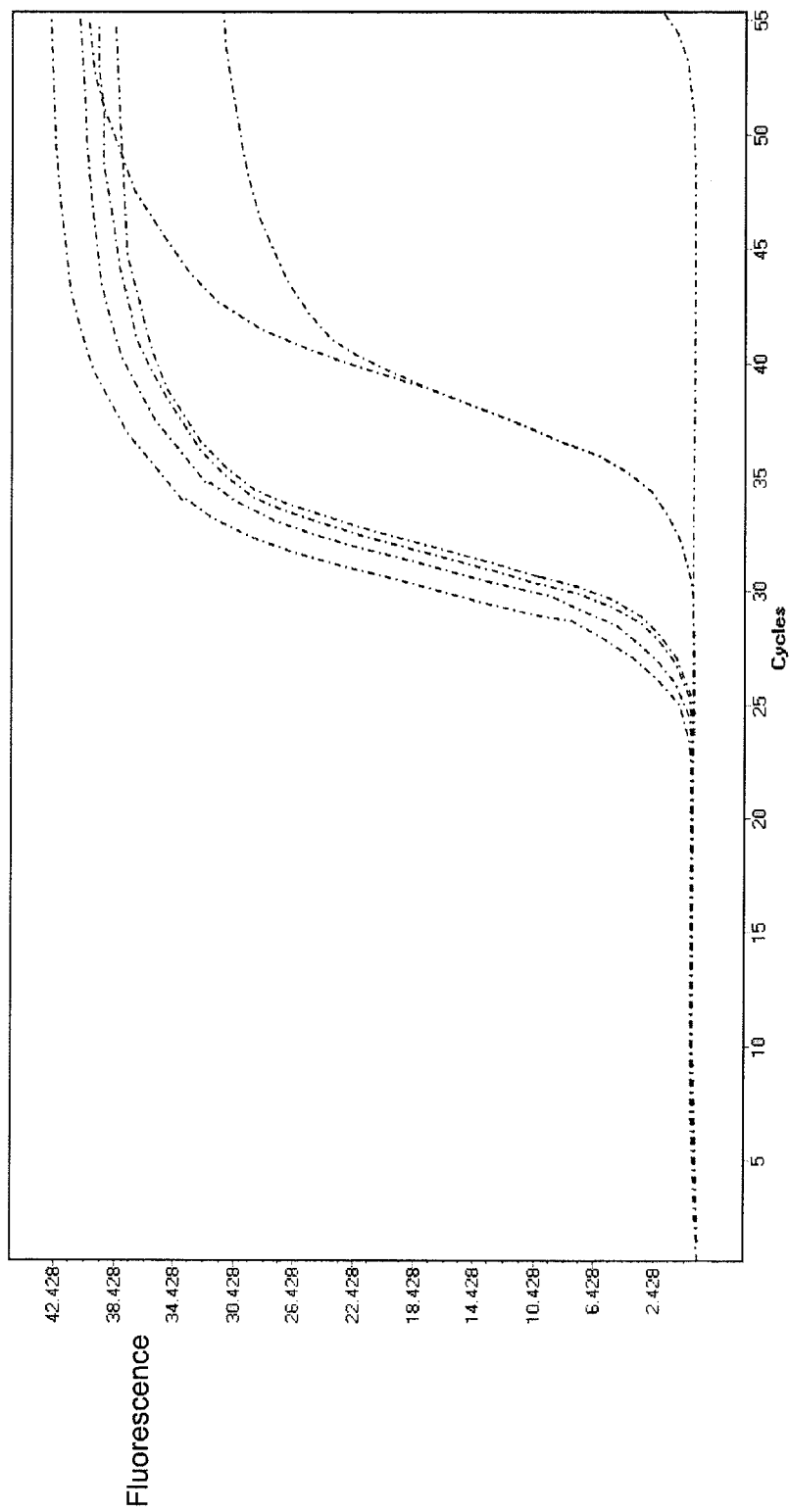

FIGS. 7a-c show similar results using a 62° C. annealing temperature. However, while the low Tm homozygotes and the heterozygotes show almost identical melting curves, a very small peak can be seen at 70° C. with the heterozygotes, and the high Tm homozygote shows some amplification. The crossing point of the high Tm allele is shifted about 6.5 cycles. Examination of the melting peak for the high Tm allele shows some slight area under the melting peak at 62° C. Because hybridization is a dynamic equilibrium, it is believed that some percentage of probes will be melted from the high Tm allele, even at 62° C., thus permitting some minimal amplification. Still, because binding of the probe to the high Tm allele is so stable, amplification of the low Tm allele is strongly favored.

Figure 8A:
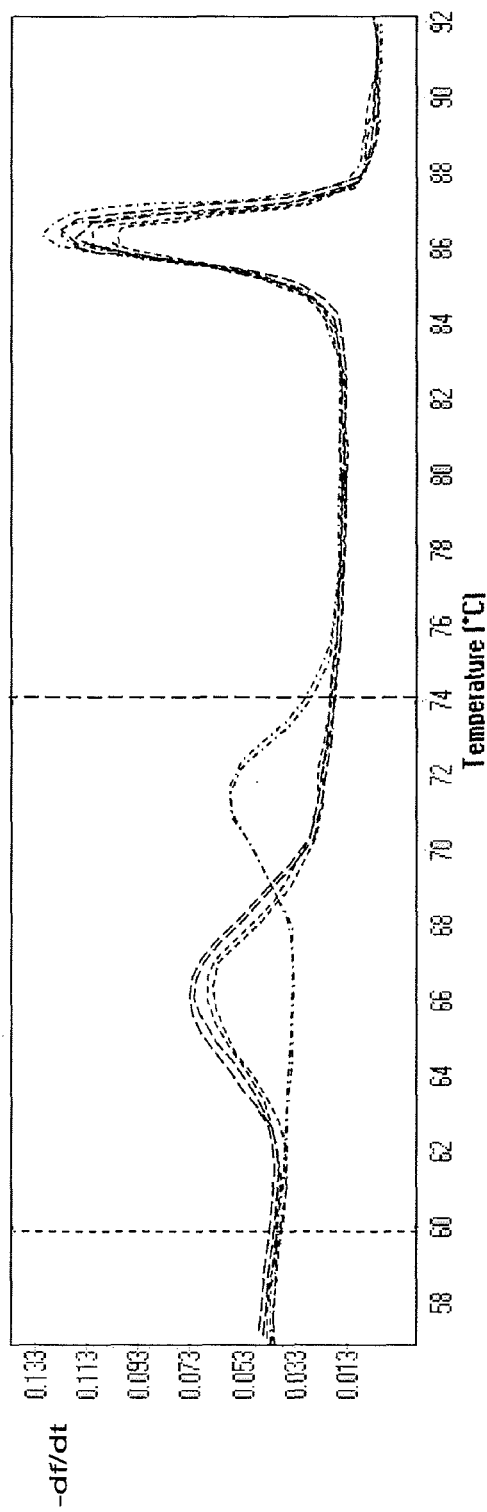
FIGS. 8a-c are similar to FIGS. 6a-c, except that a 64° C. annealing temperature is used.
Figure 8B:
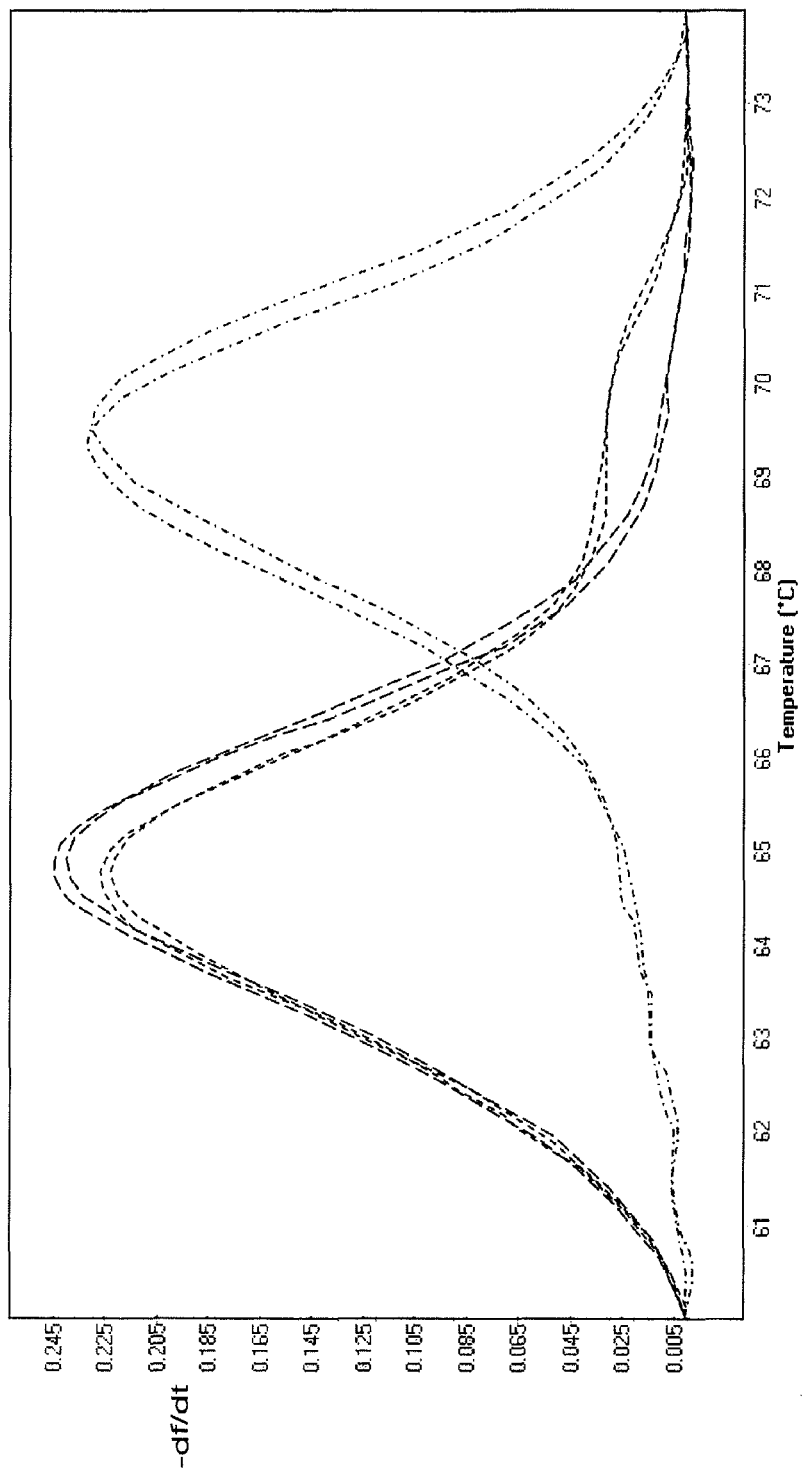
Figure 8C:
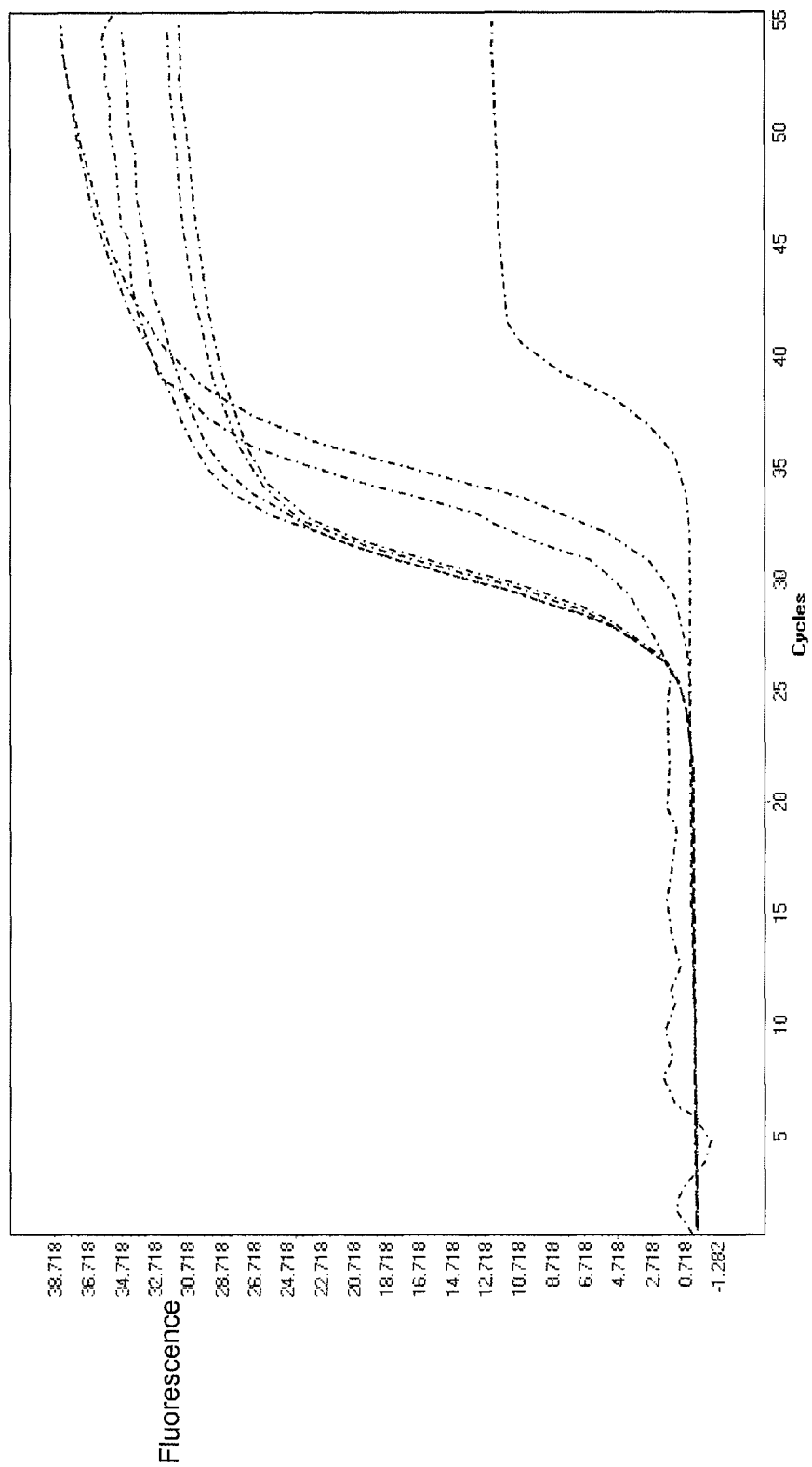

FIGS. 8a-c show similar results using a 64° C. annealing temperature. Amplification of the high Tm allele is delayed, but not as much as with a 62° C. annealing temperature (about 4 cycles vs. 6.5 cycles). In the heterozygotes, there is a small but easily distinguishable melting peak at 70° C., showing some amplification of the higher Tm allele in the heterozygotes.

Figure 9A:
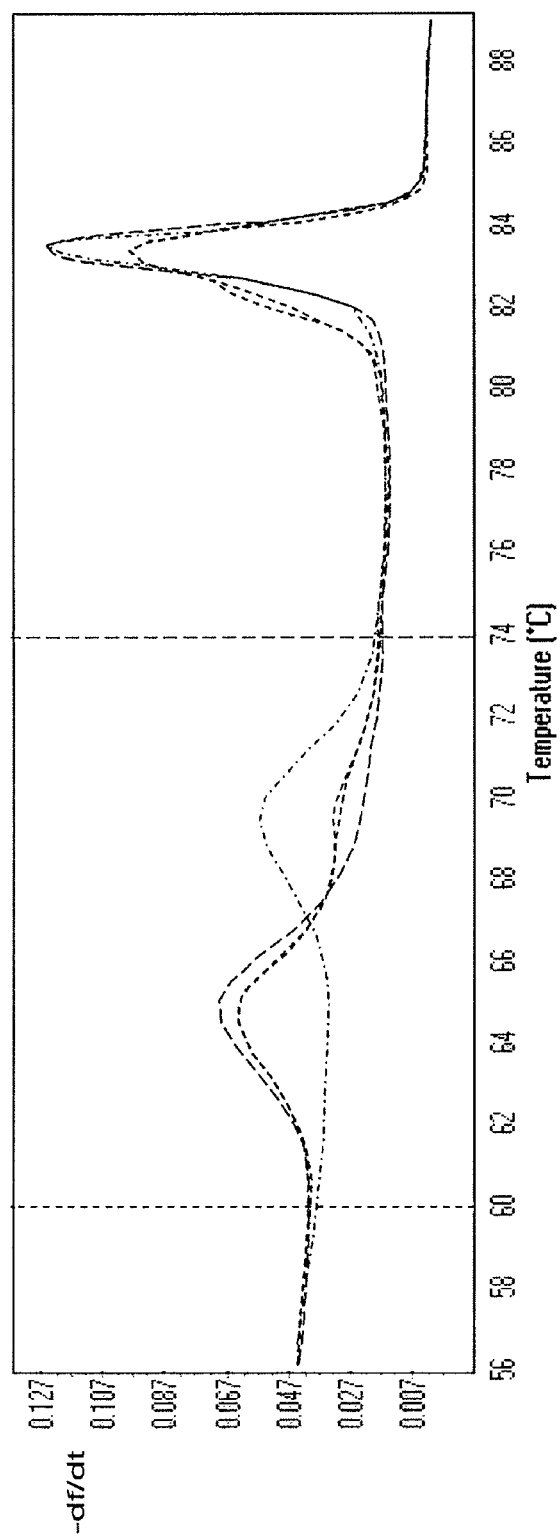
FIGS. 9a-c are similar to FIGS. 6a-c, except that a 65° C. annealing temperature is used.
Figure 9B:
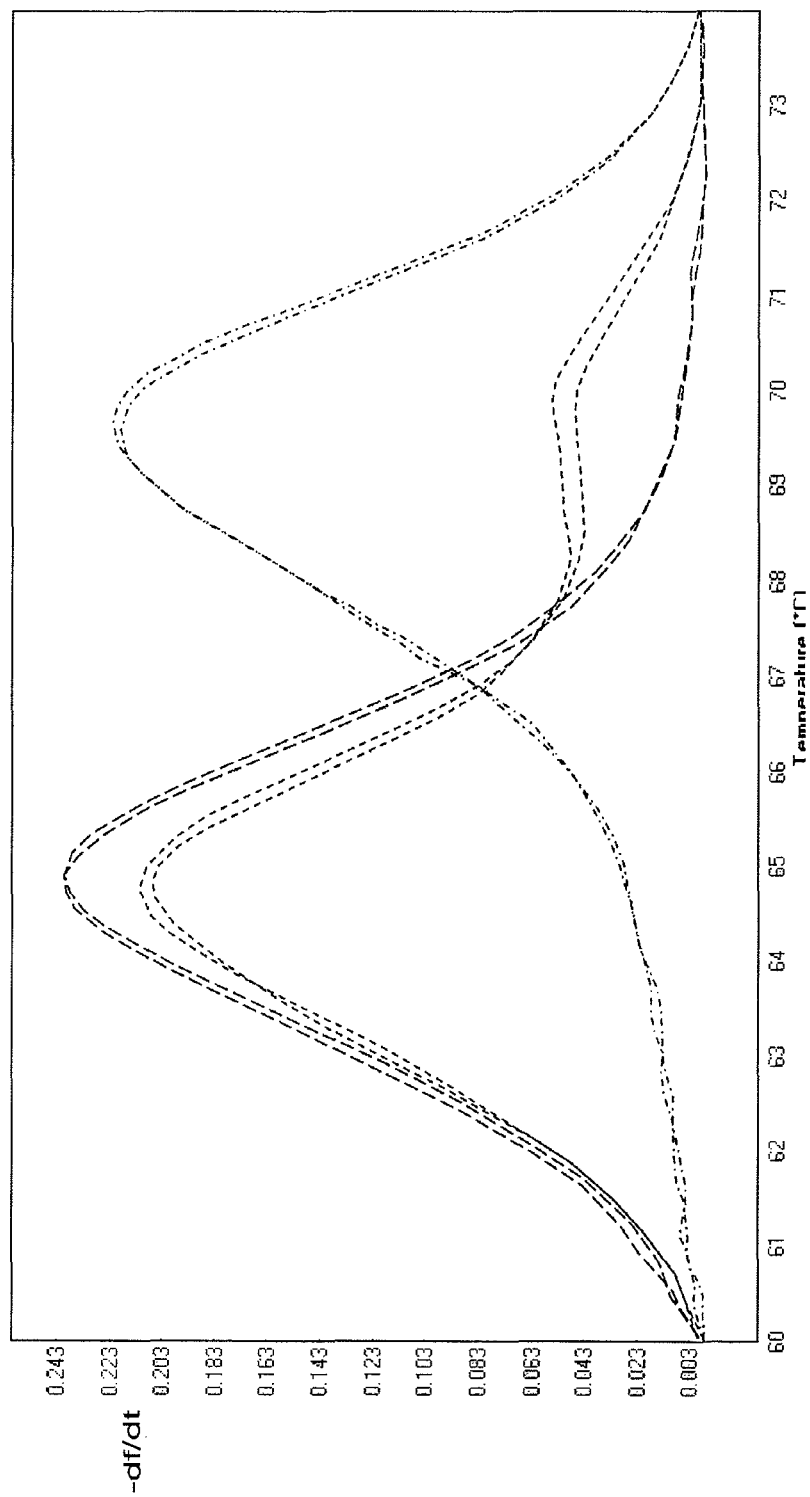
Figure 9C:
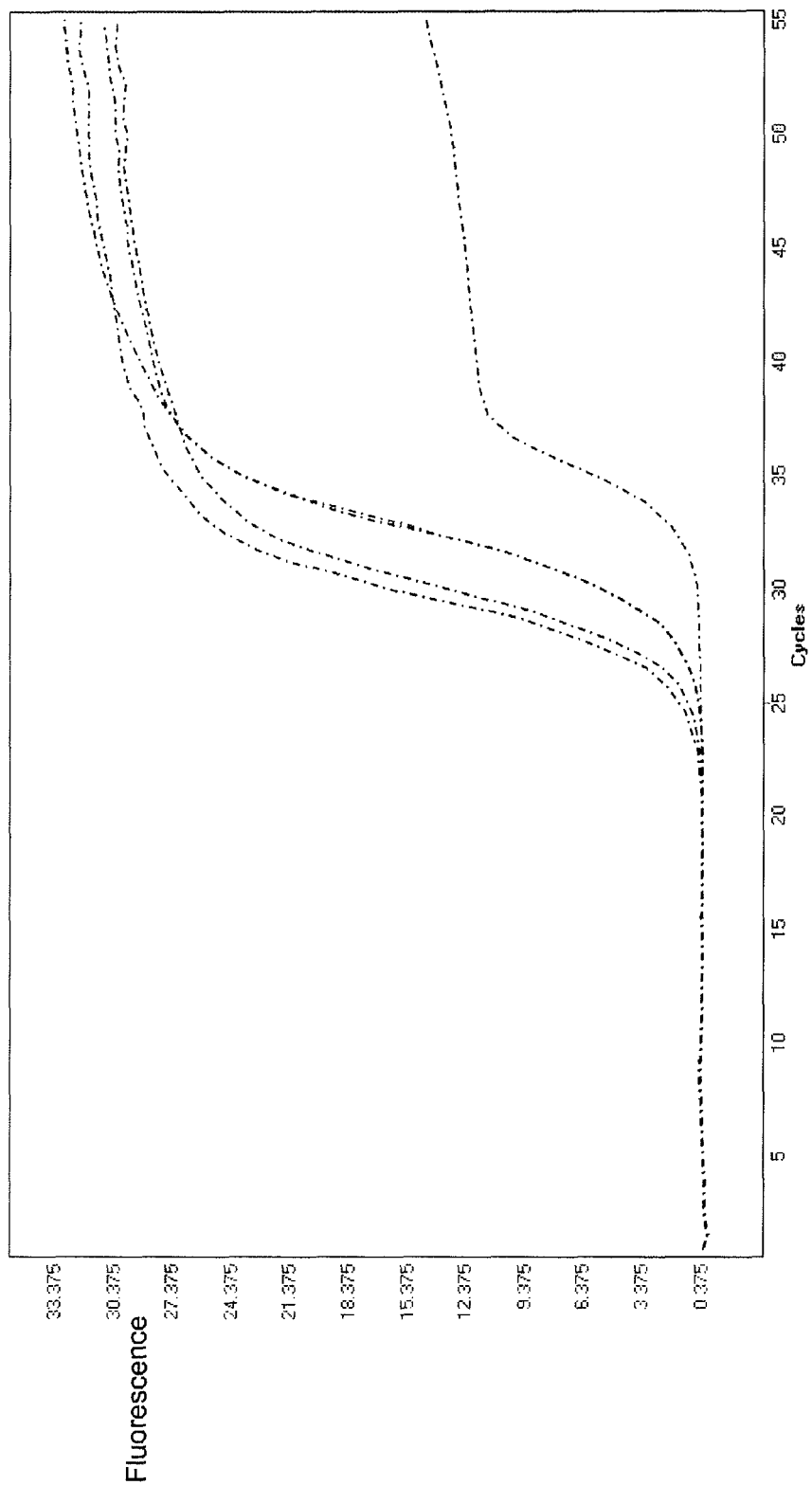

FIGS. 9a-c show the results with a 65° C. annealing temperature. Amplification of the high Tm homozygote is delayed only about 2.5 cycles, and the heterozygote shows a more defined peak at 70° C. Still, the low Tm allele is strongly favored.

Figure 10A:
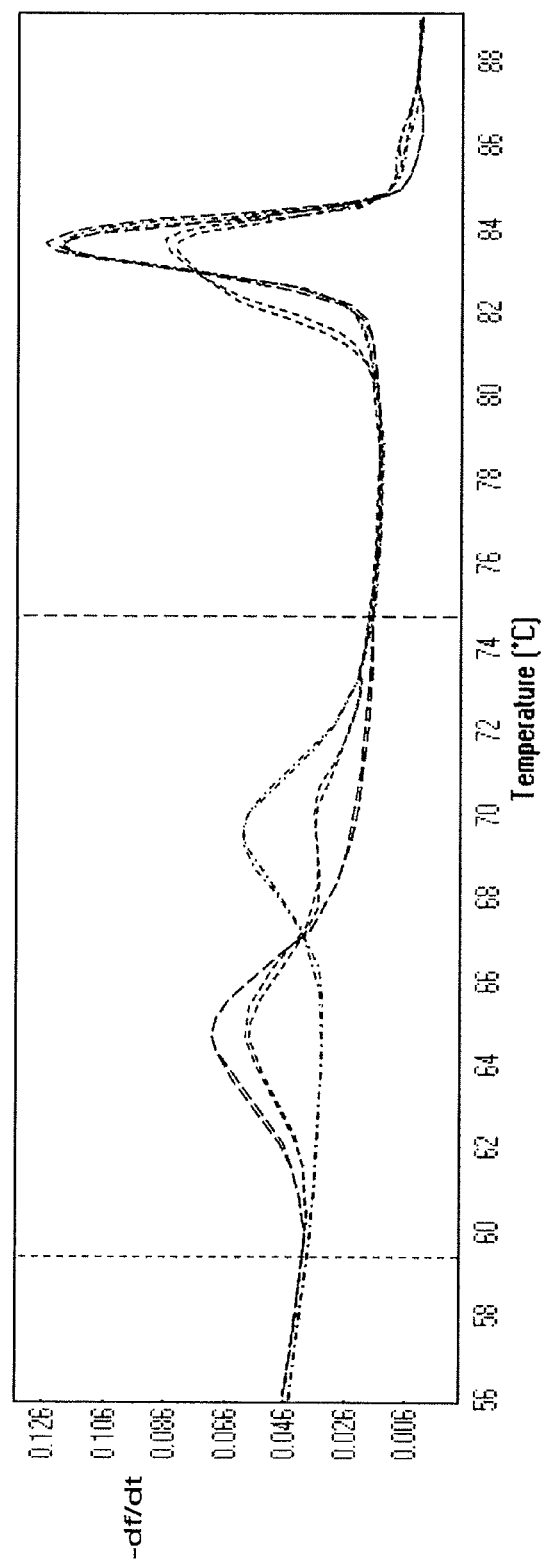
FIGS. 10a-c are similar to FIGS. 6a-c, except that a 67° C. annealing temperature is used.
Figure 10B:
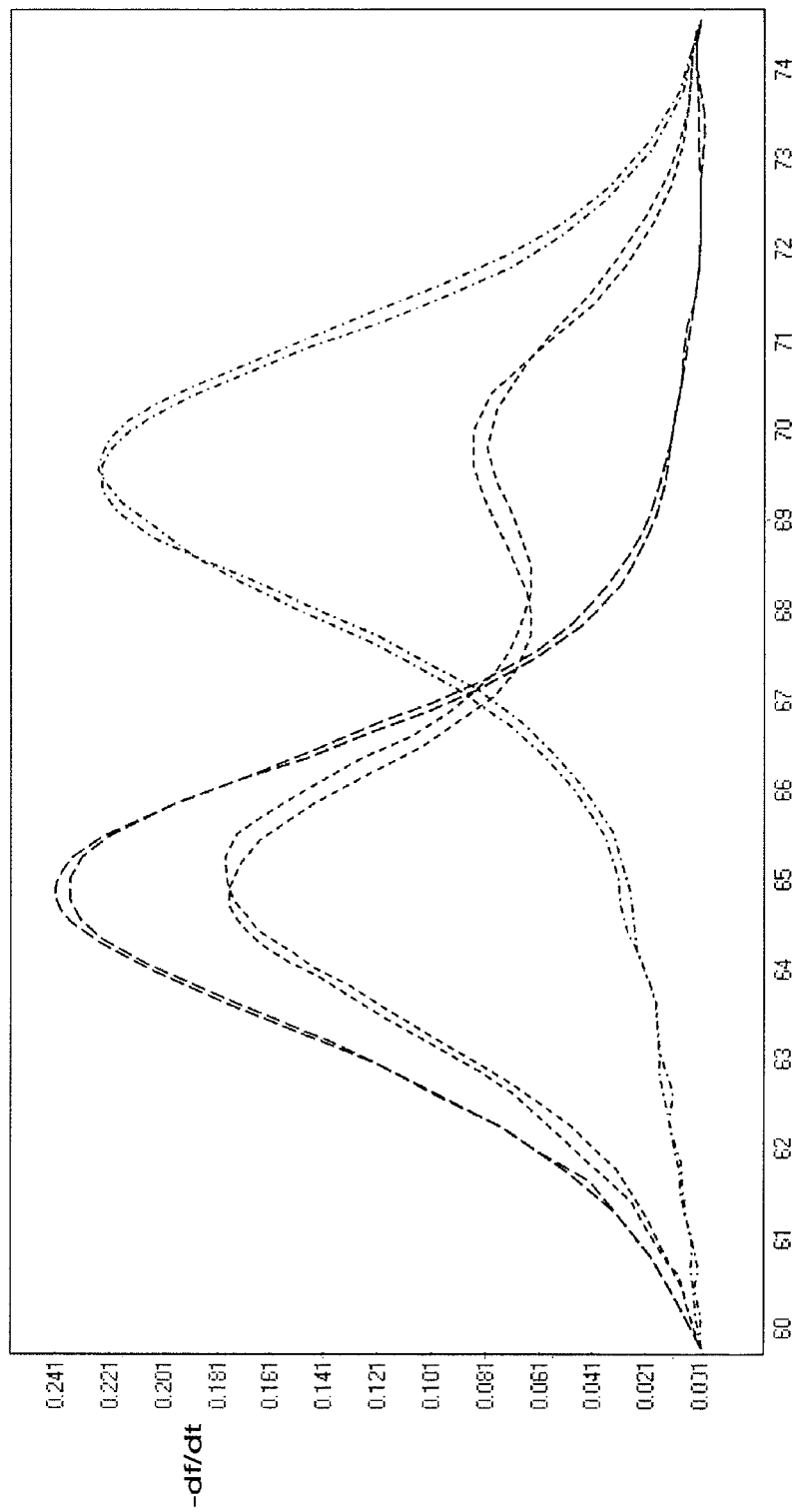
Figure 10C:
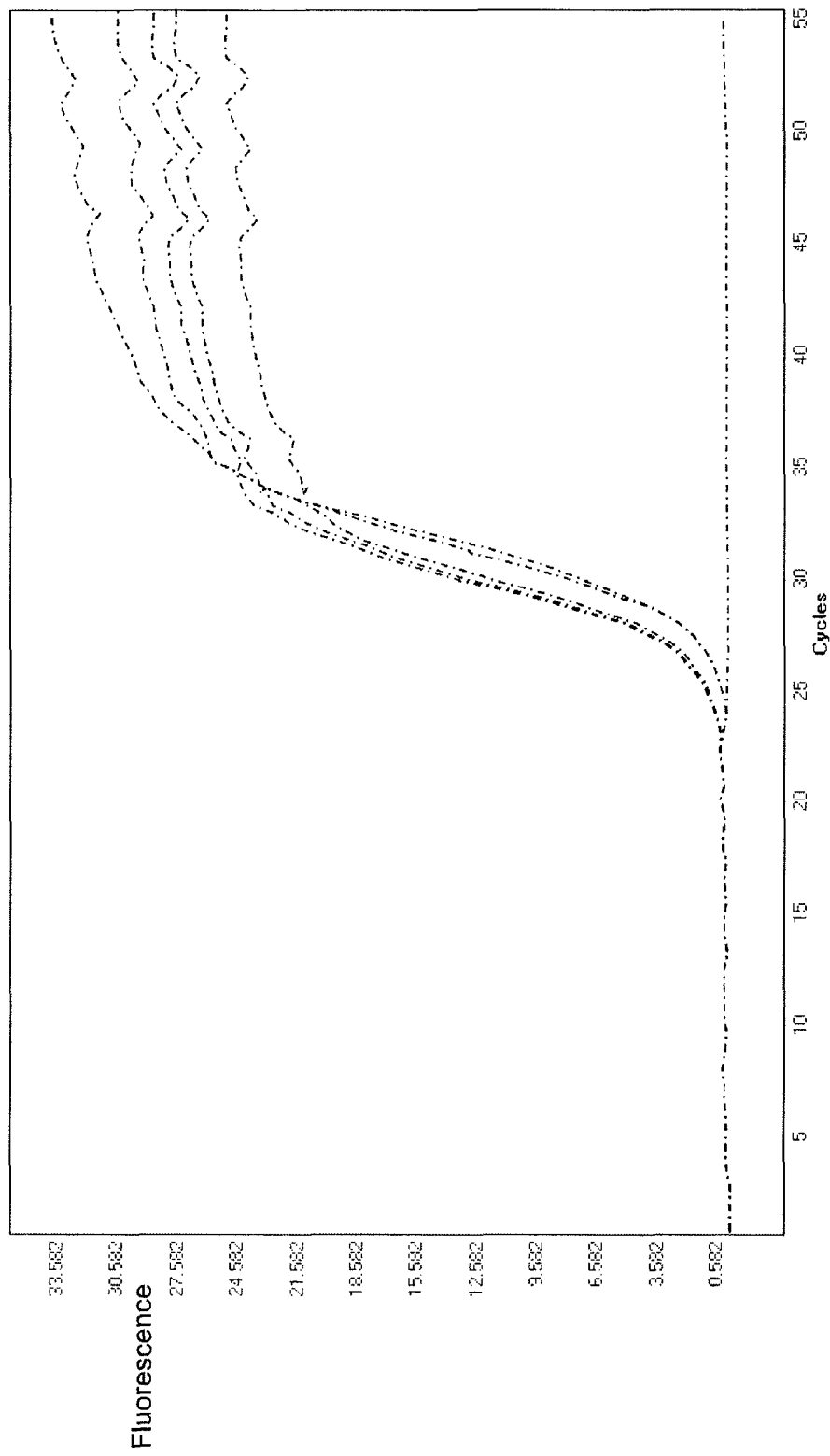

FIGS. 10a-c show the results with a 67° C. annealing temperature. This annealing temperature is about half way between the two Tms. Amplification of the high Tm homozygote is delayed only about 1.5 cycles. While the heterozygote clearly shows a melting peak at 70° C., the low Tm allele is still favored.

Figure 11A:
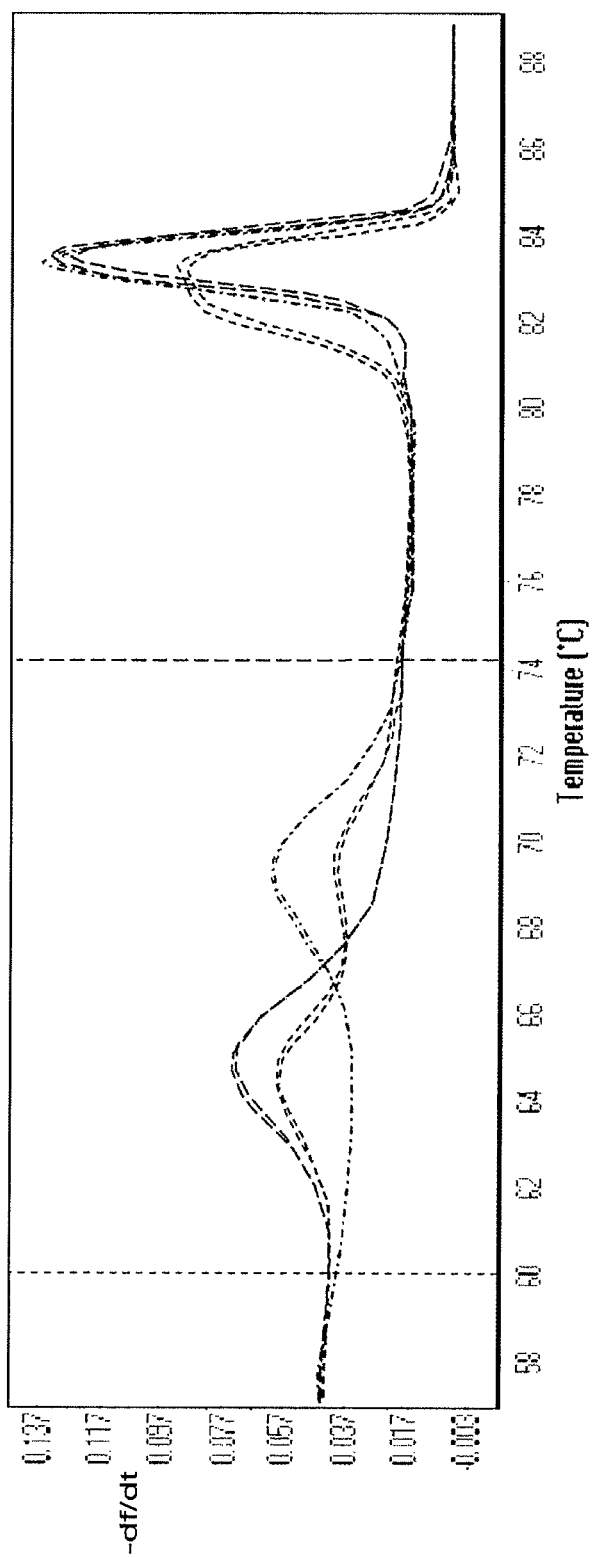
FIGS. 11a-c are similar to FIGS. 6a-c, except that a 68° C. annealing temperature is used.
Figure 11B:
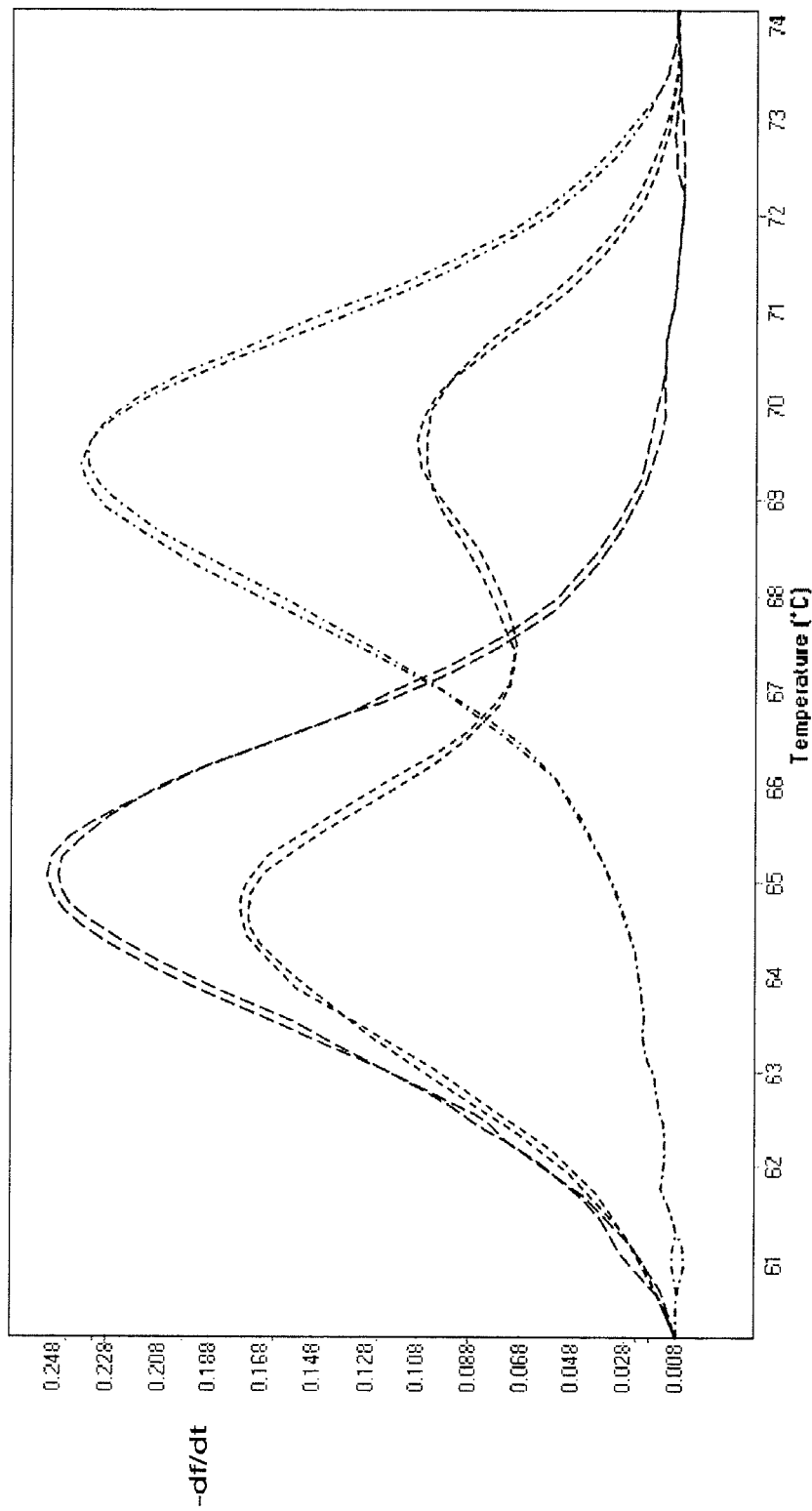
Figure 11C:
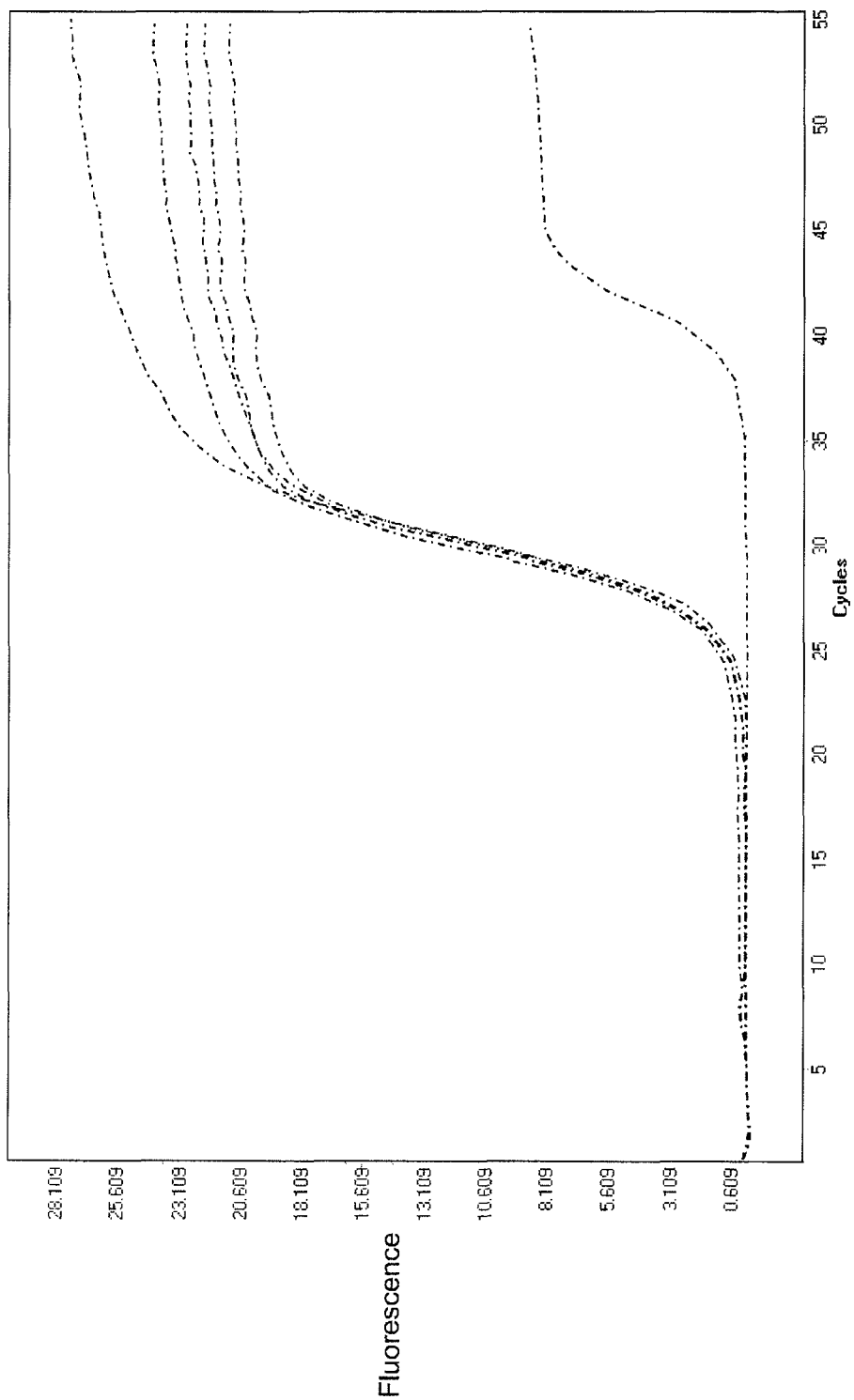

FIGS. 11a-c show the results with a 68° C. annealing temperature. Amplification of the high Tm homozygote is delayed only about 0.6 cycles. The heterozygote clearly shows a melting peak at 70° C., but the peak at 65° C. is still larger.

Figure 12A:
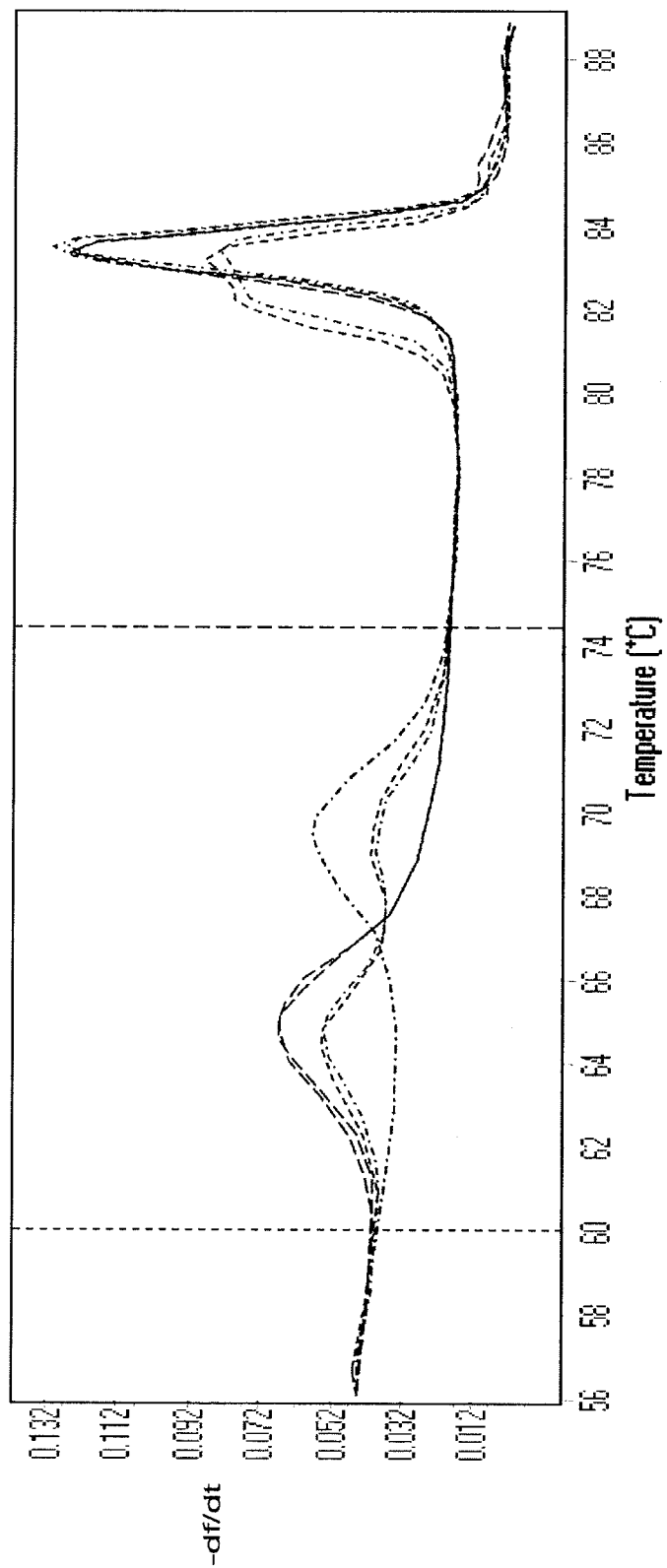
FIGS. 12a-c are similar to FIGS. 6a-c, except that a 69° C. annealing temperature is used.
Figure 12B:
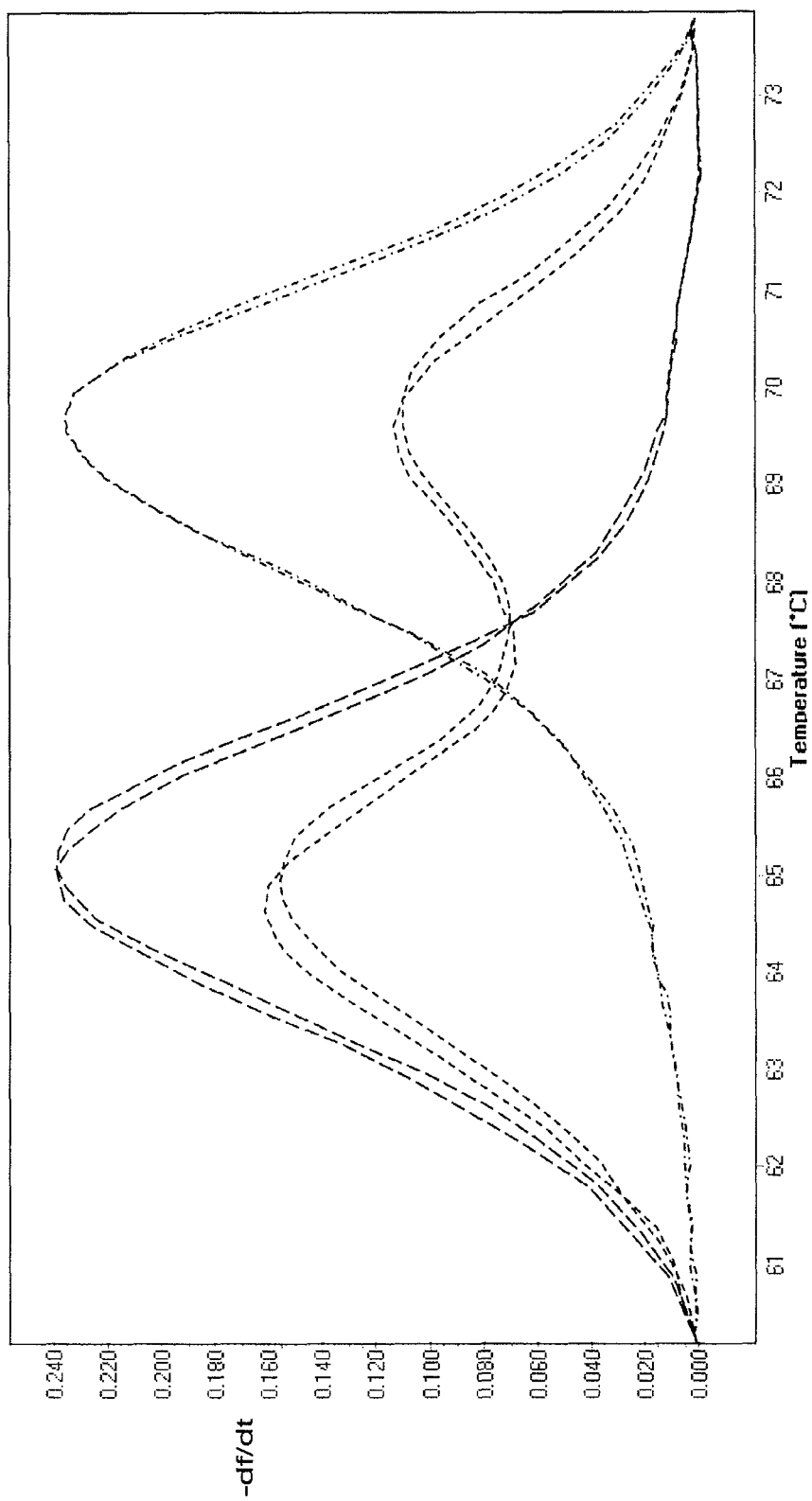
Figure 12C:
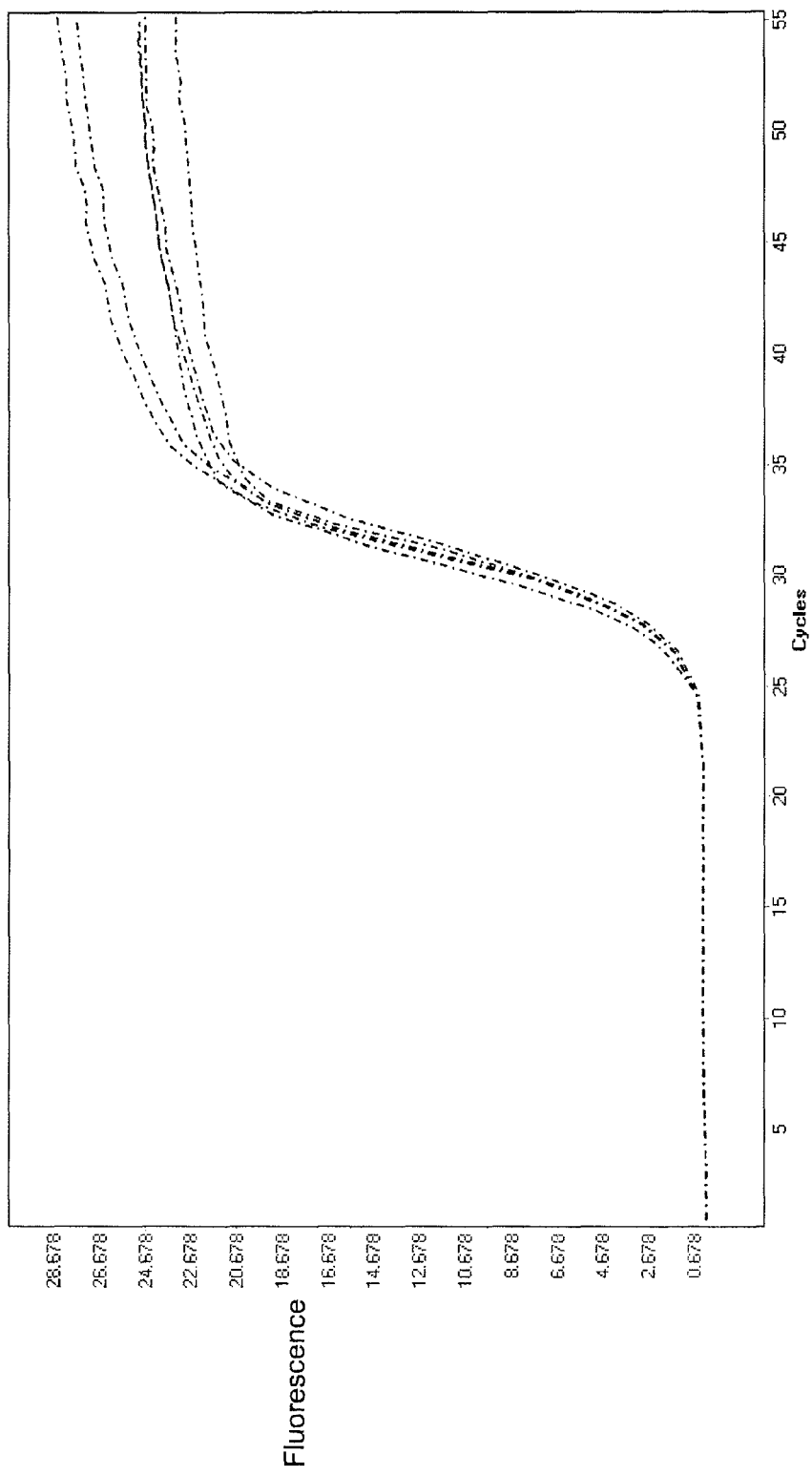

FIGS. 12a-c show the results with a 69° C. annealing temperature. This annealing temperature is only about one ° C. below the Tm of the high Tm allele. Amplification of the high Tm homozygote is delayed only about 0.7 cycles. Still, the melting peaks show that amplification the low Tm allele is still favored.

Figure 13A:
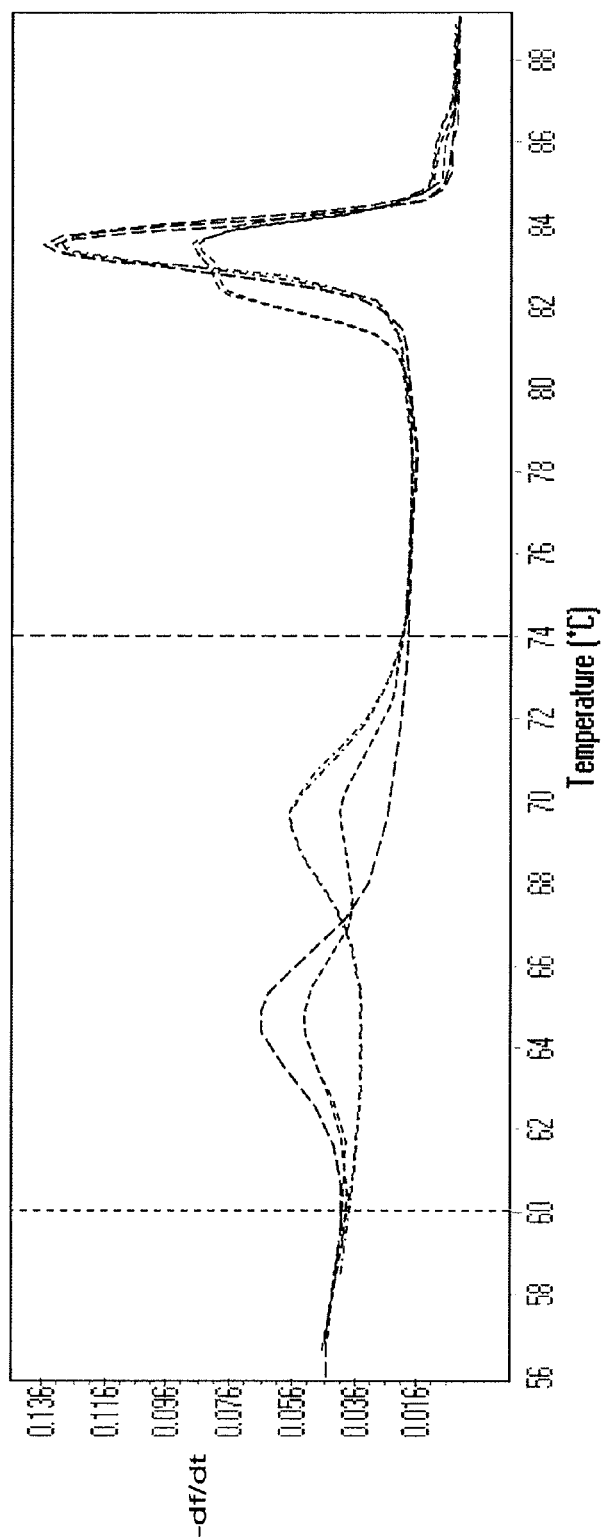
FIGS. 13a-c are similar to FIGS. 6a-c, except that a 70° C. annealing temperature is used.
Figure 13B:
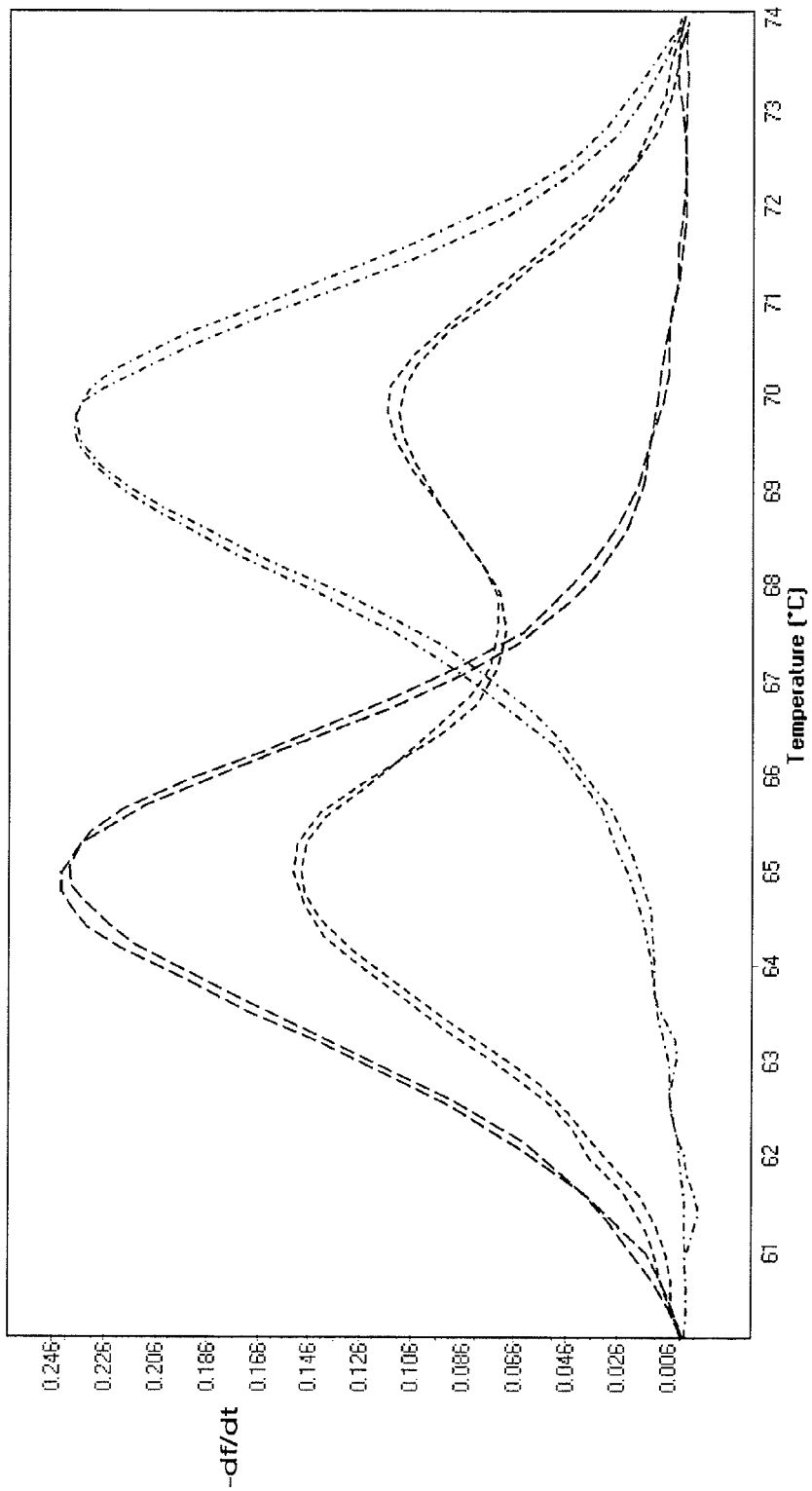
Figure 13C:
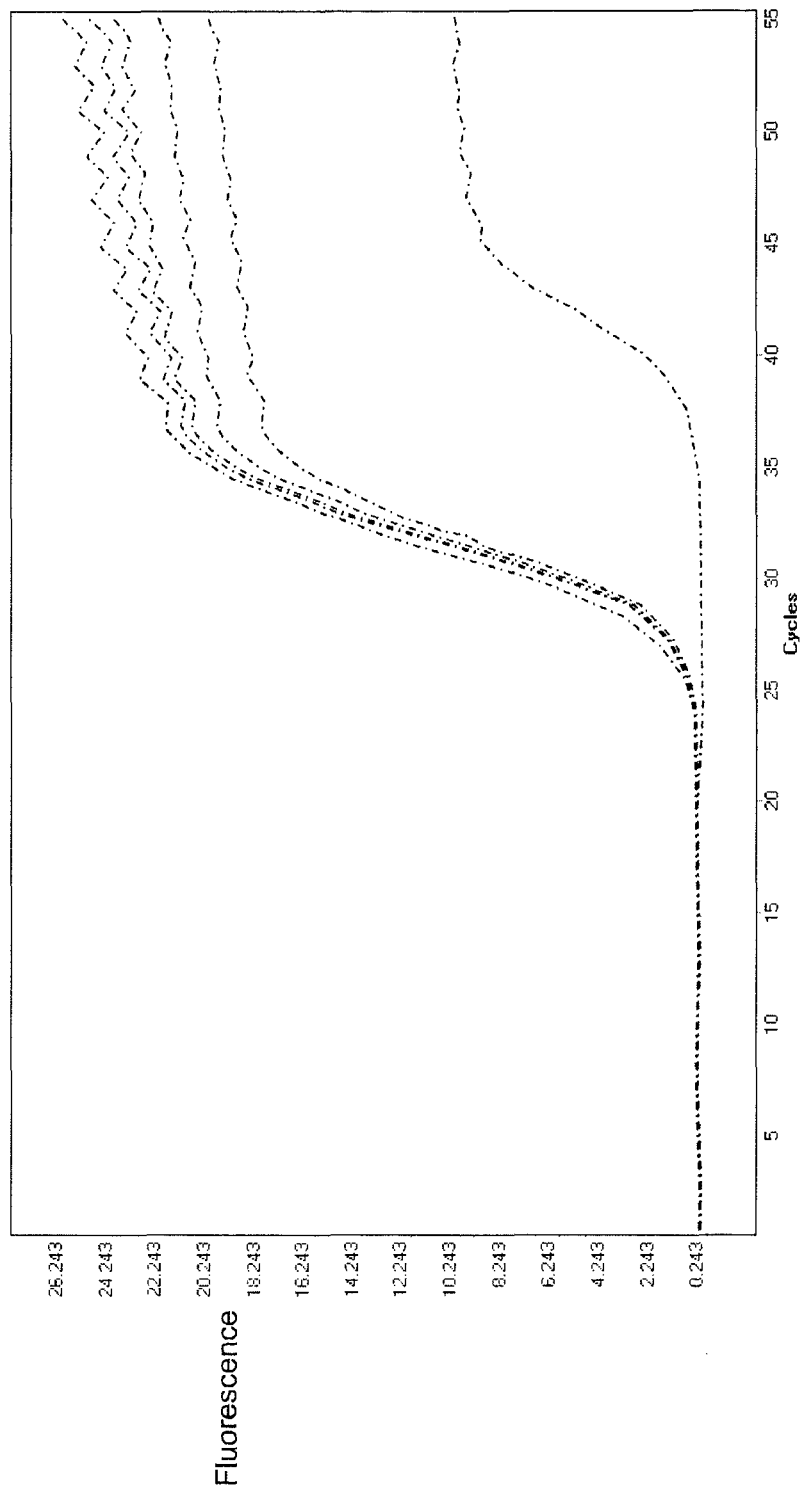
Figure 14A:
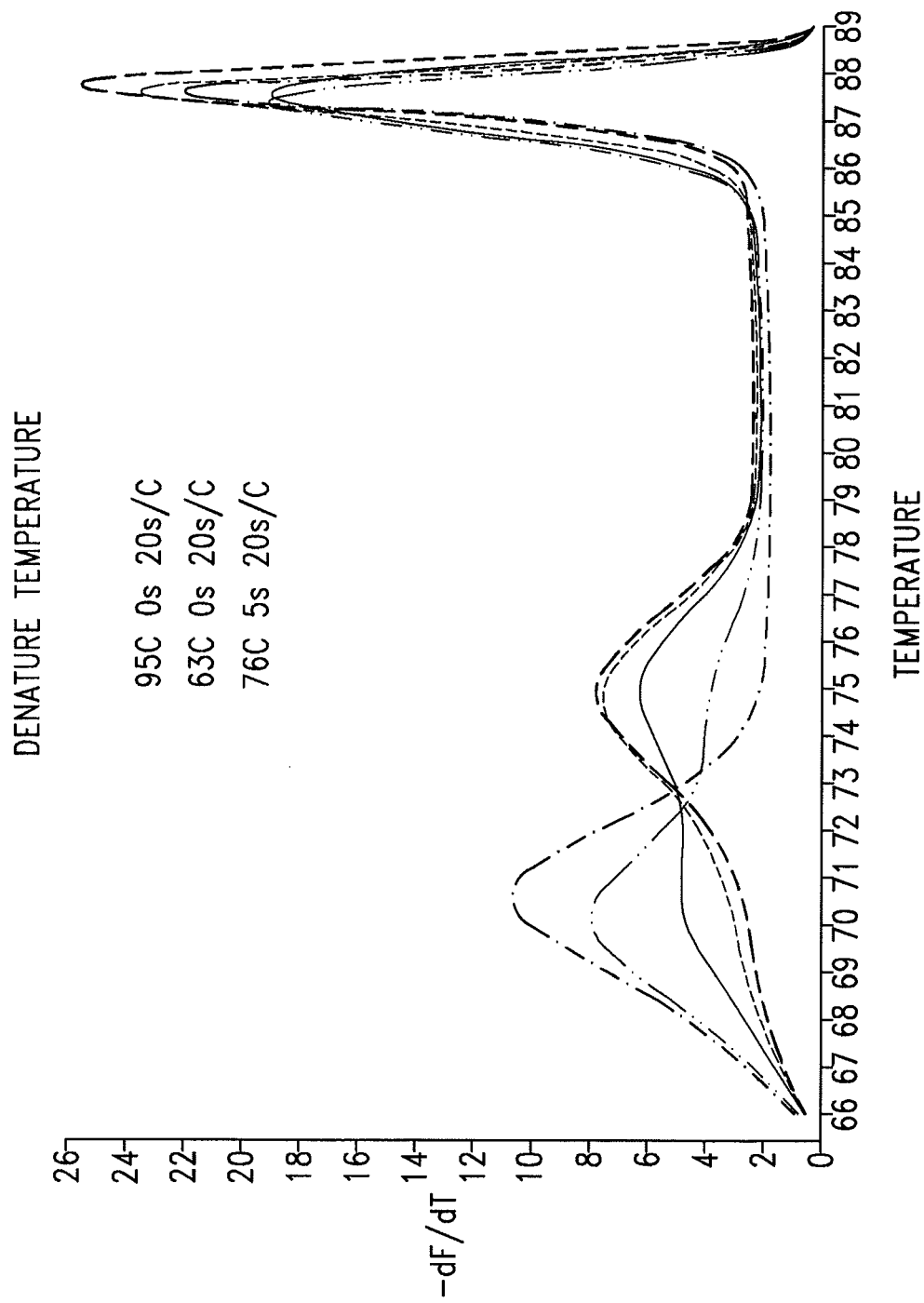
FIGS. 14a-d show melting of forensic SNP rs 1490413 A/G amplicon, using different denaturation temperatures ((———)=1A:10G; (------)=1A:100G; (— — —)=1A:1000G; (—··—··—)=A:G; (········)=G; (—·—·—)=A).
Figure 14B:
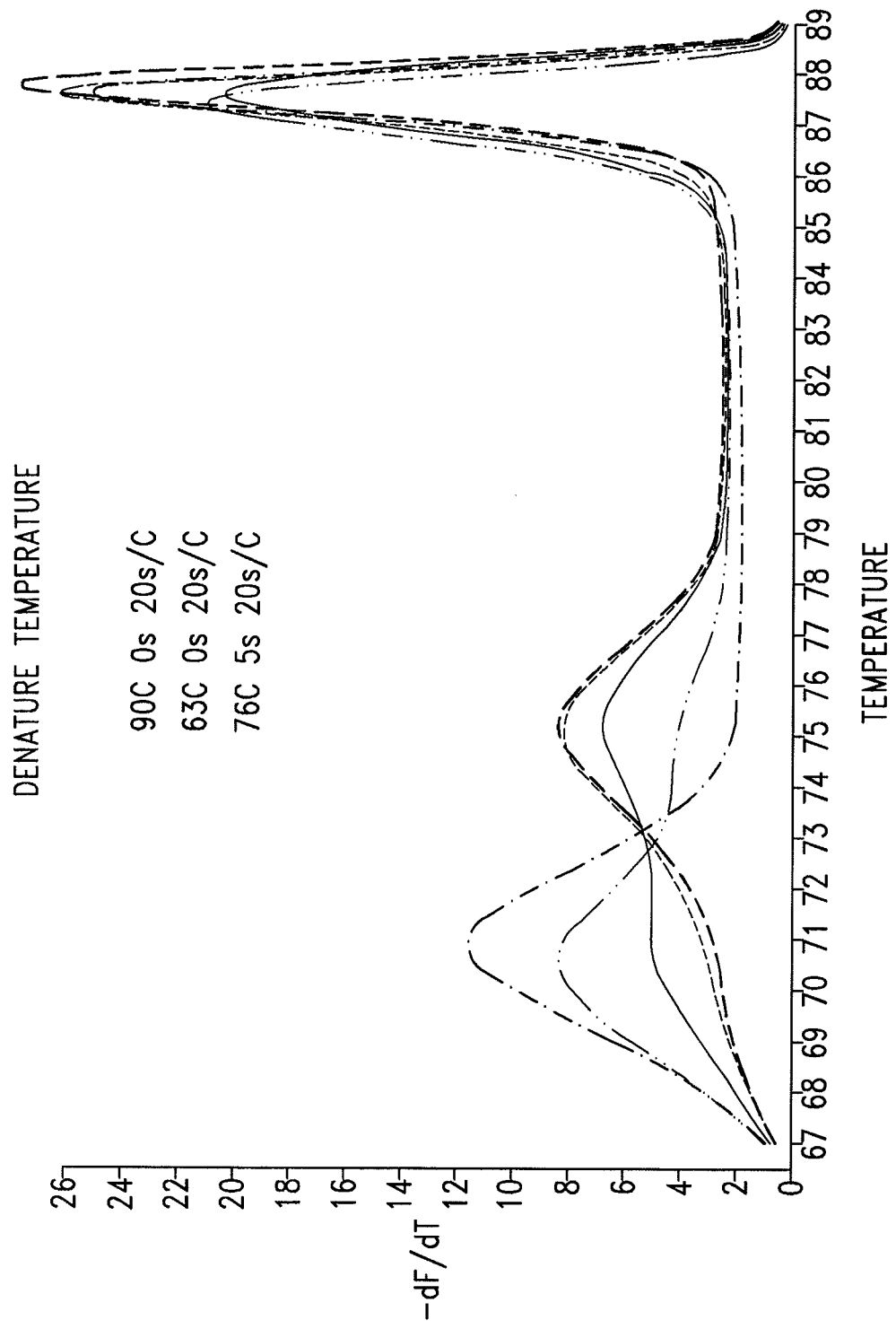
Figure 14C:
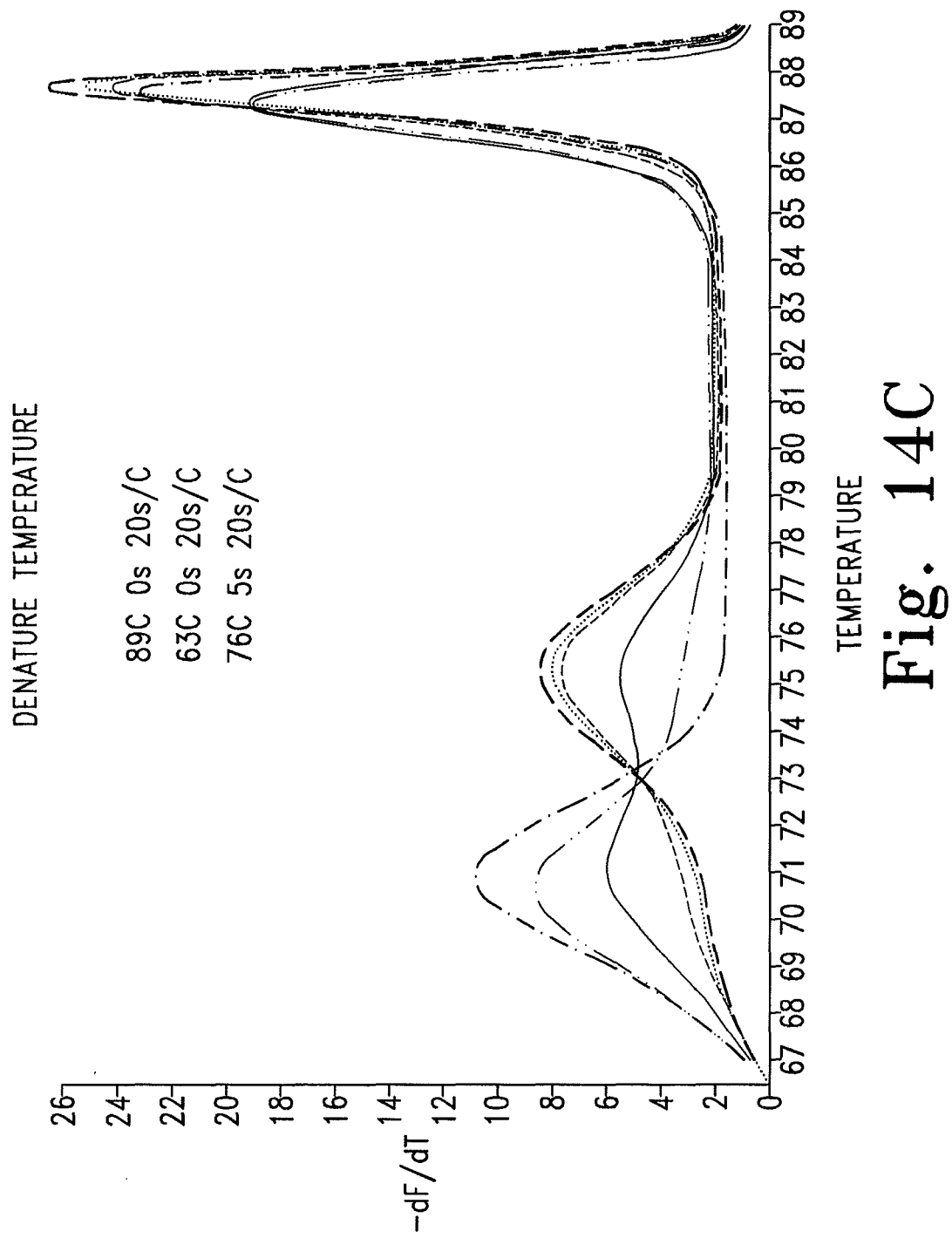
Figure 14D:
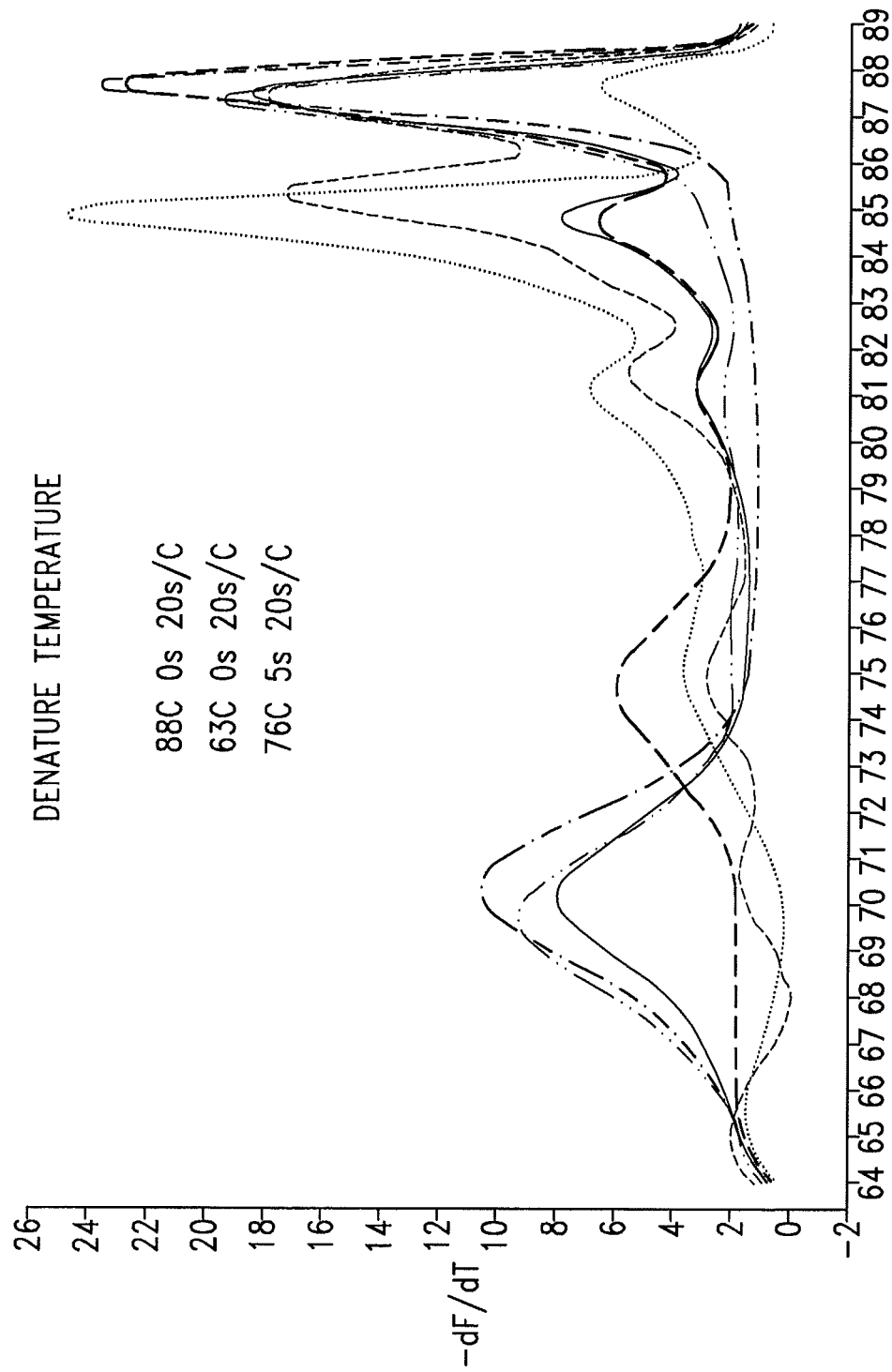
Figure 15A:
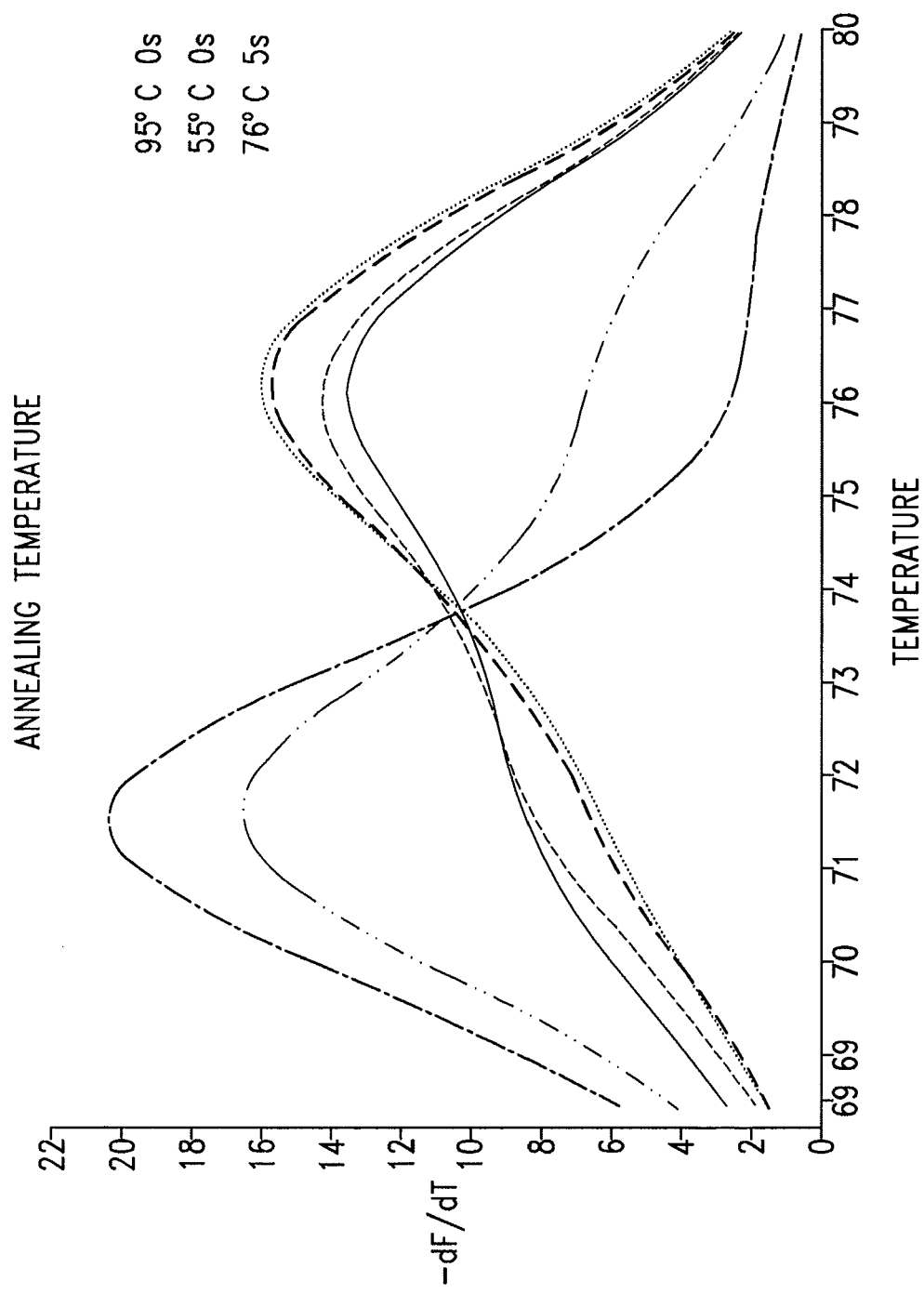
FIGS. 15a-d are similar to FIGS. 14a-d, except using different annealing temperatures ((———)=1A:10G; (------)=1A:100G; (— — —)=1A:1000G; (—··—··—)=A:G; (········)=G; (—·—·—)=A).
Figure 15B:
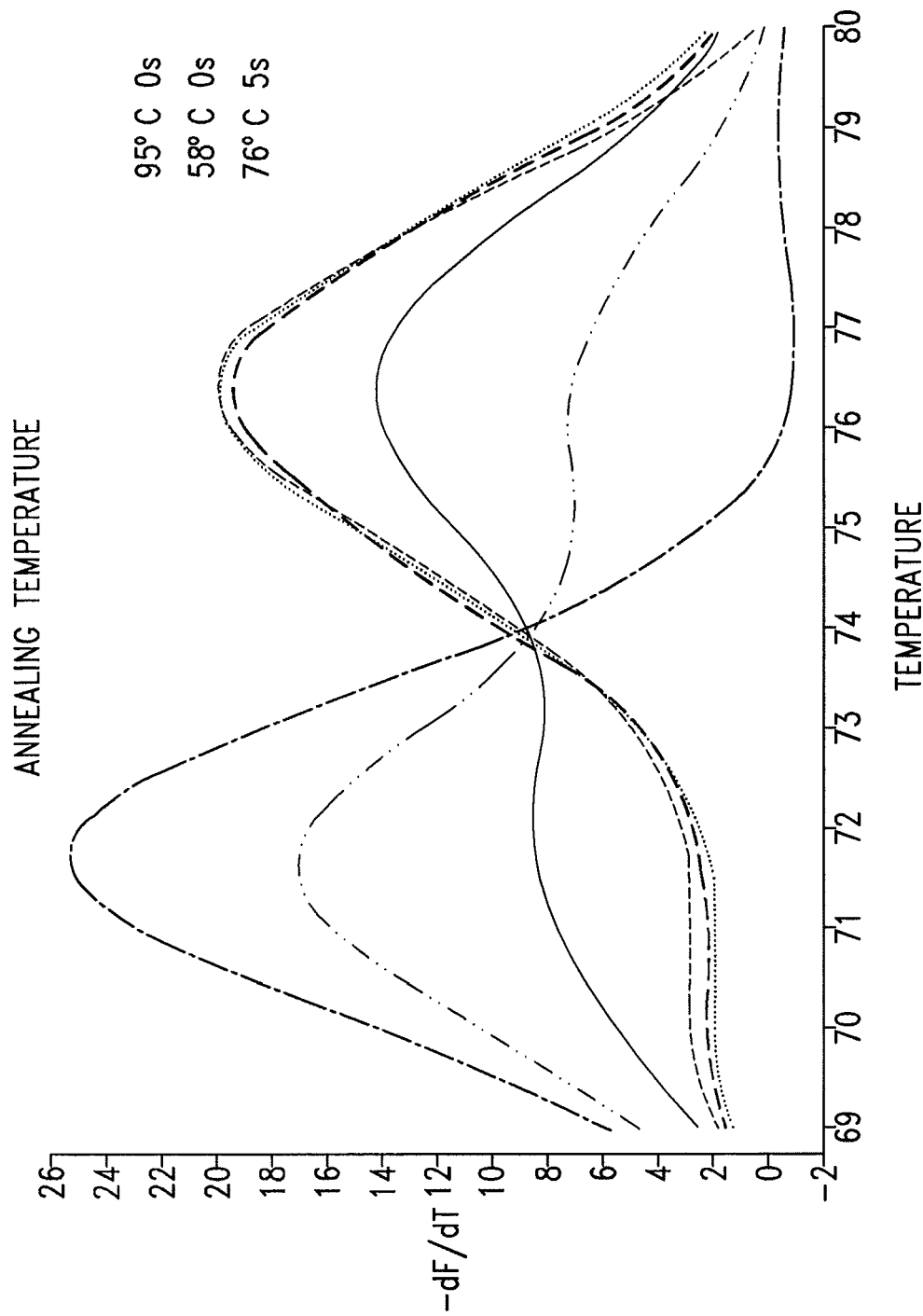
Figure 15C:
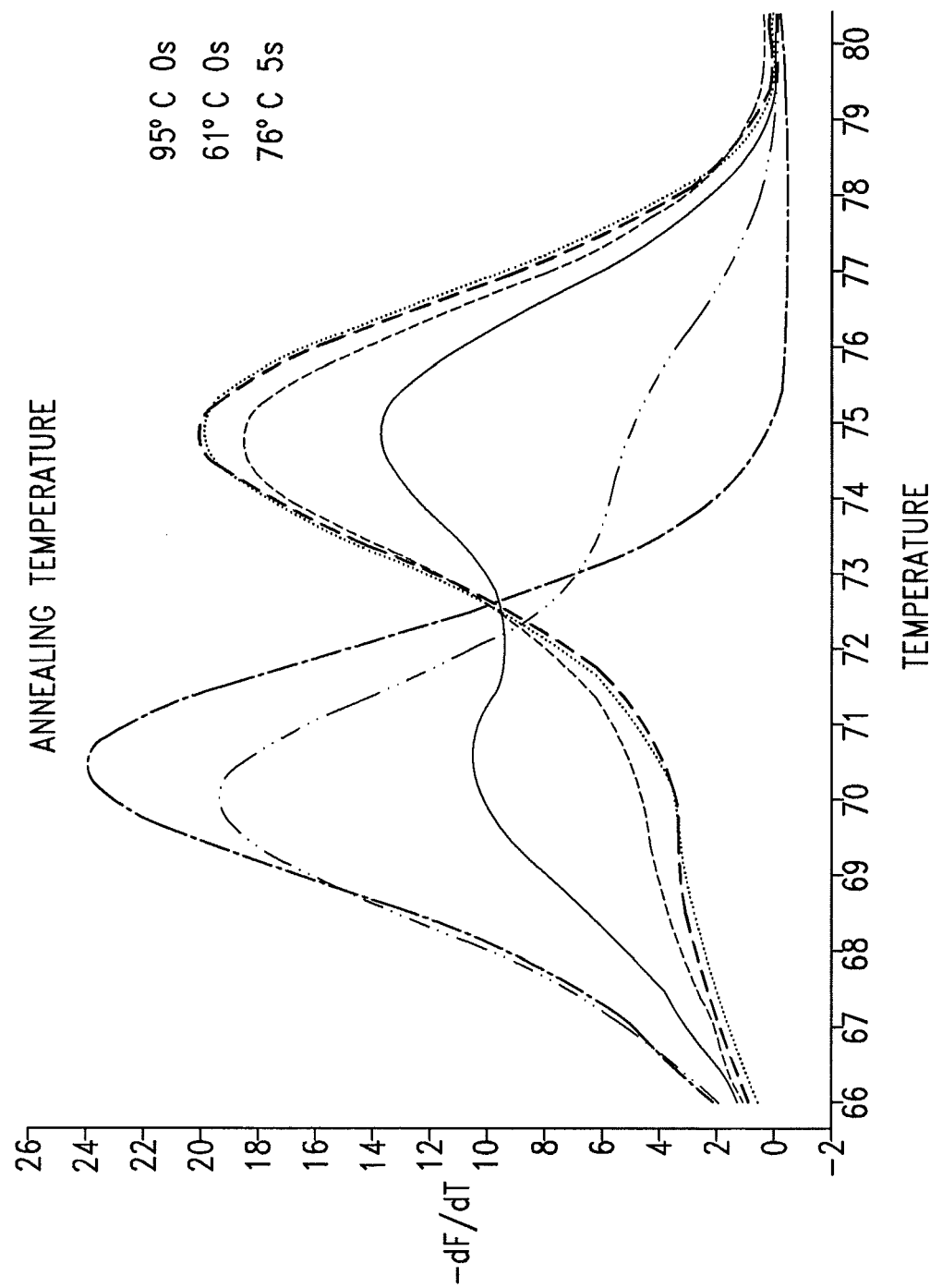
Figure 15D:
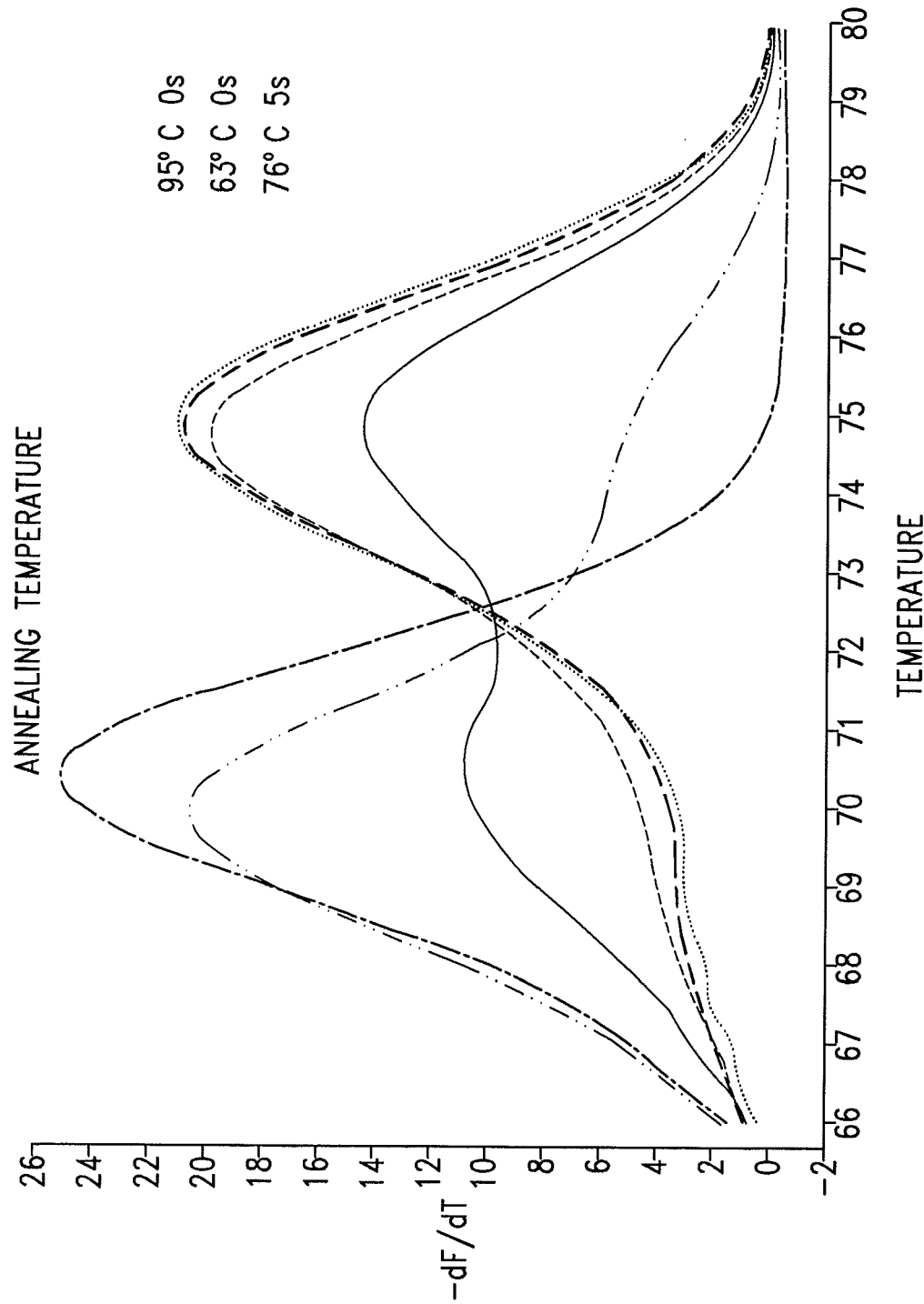
Figure 16A:
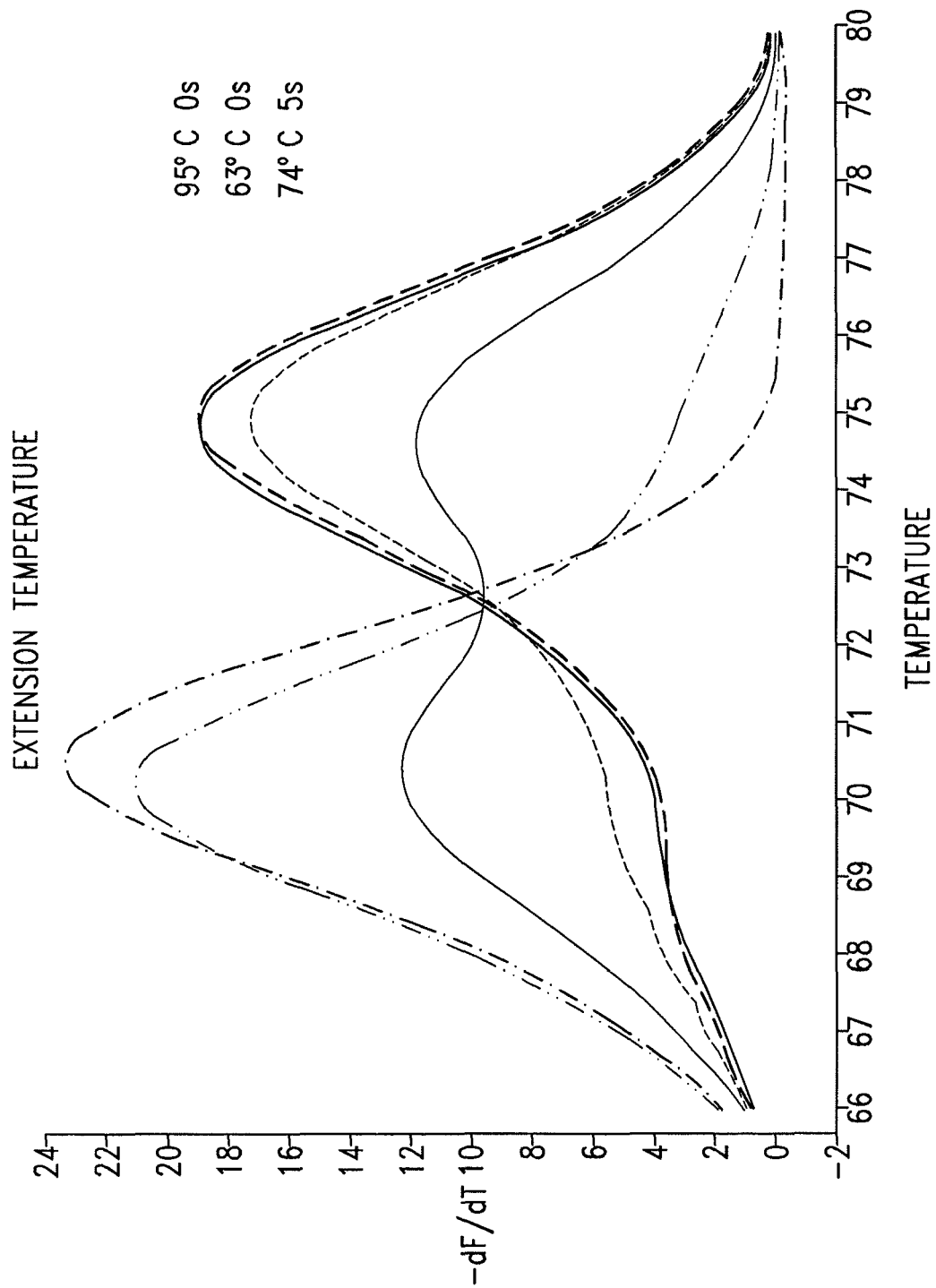
FIGS. 16a-d are similar to FIGS. 14a-d, except using different extension temperatures ((———)=1A:10G; (------)=1A:100G; (— — —)=1A:1000G; (—··—··—)=A:G; (········)=G; (—·—·—)=A).
Figure 16B:
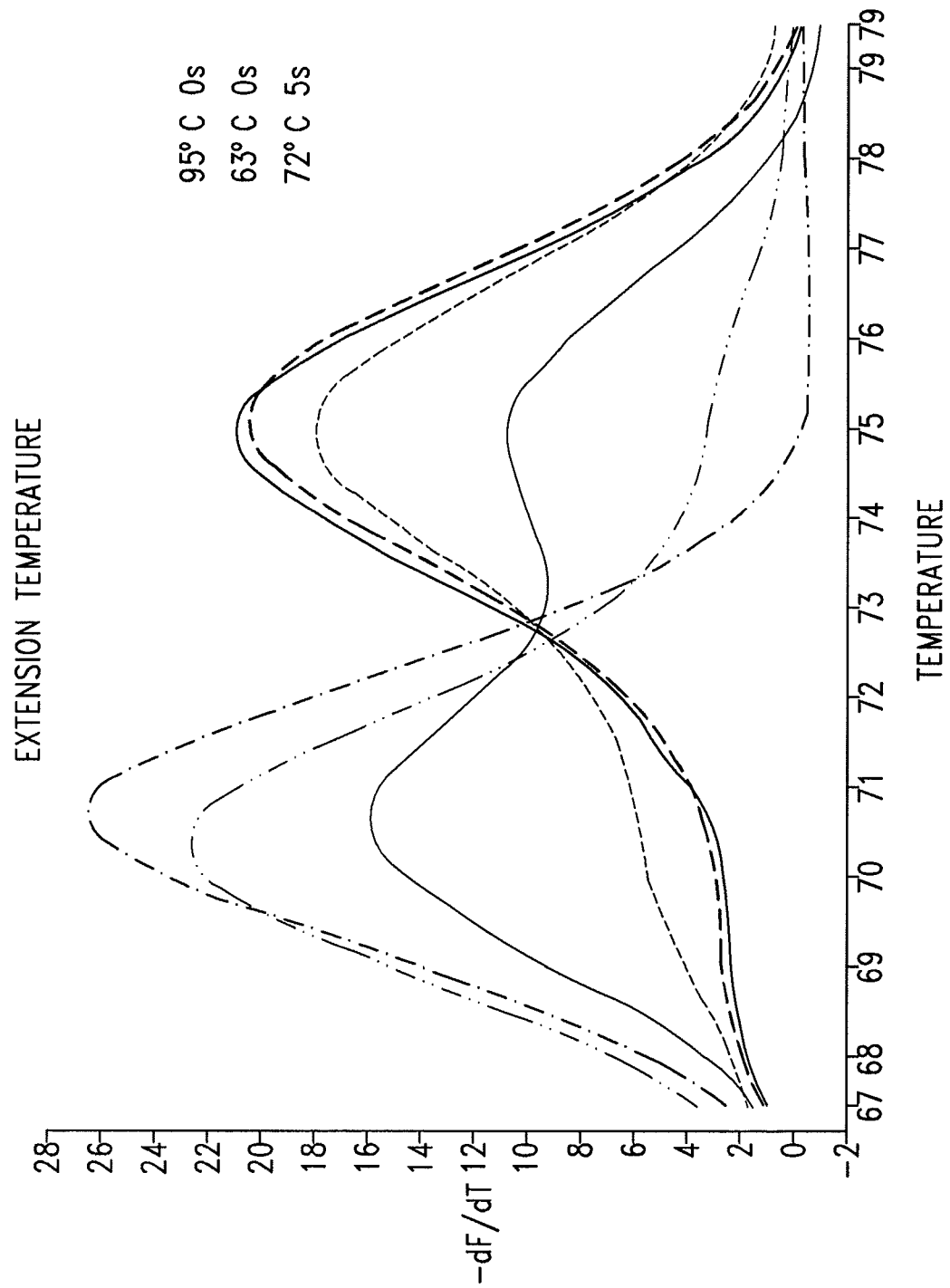
Figure 16C:
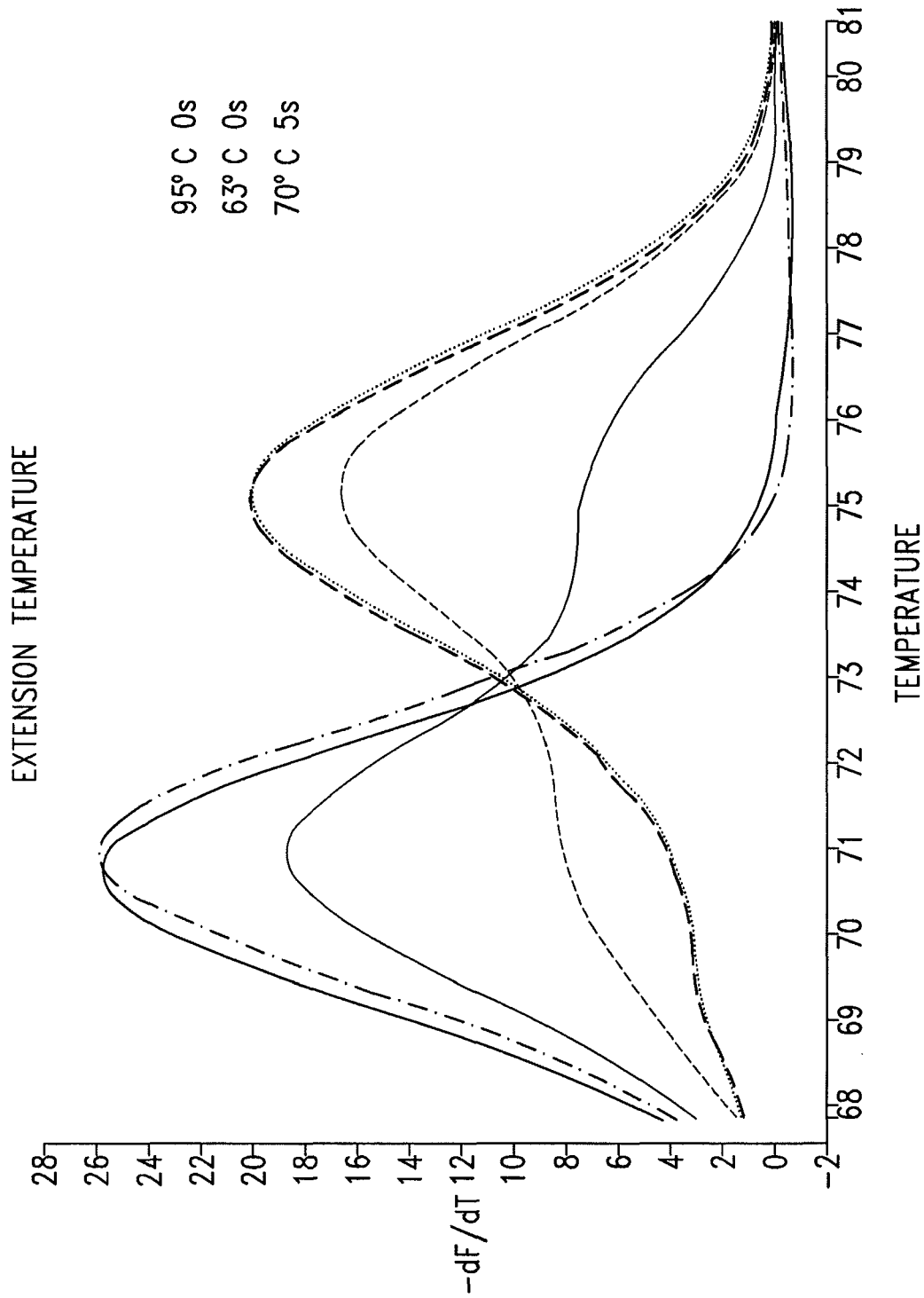
Figure 16D:
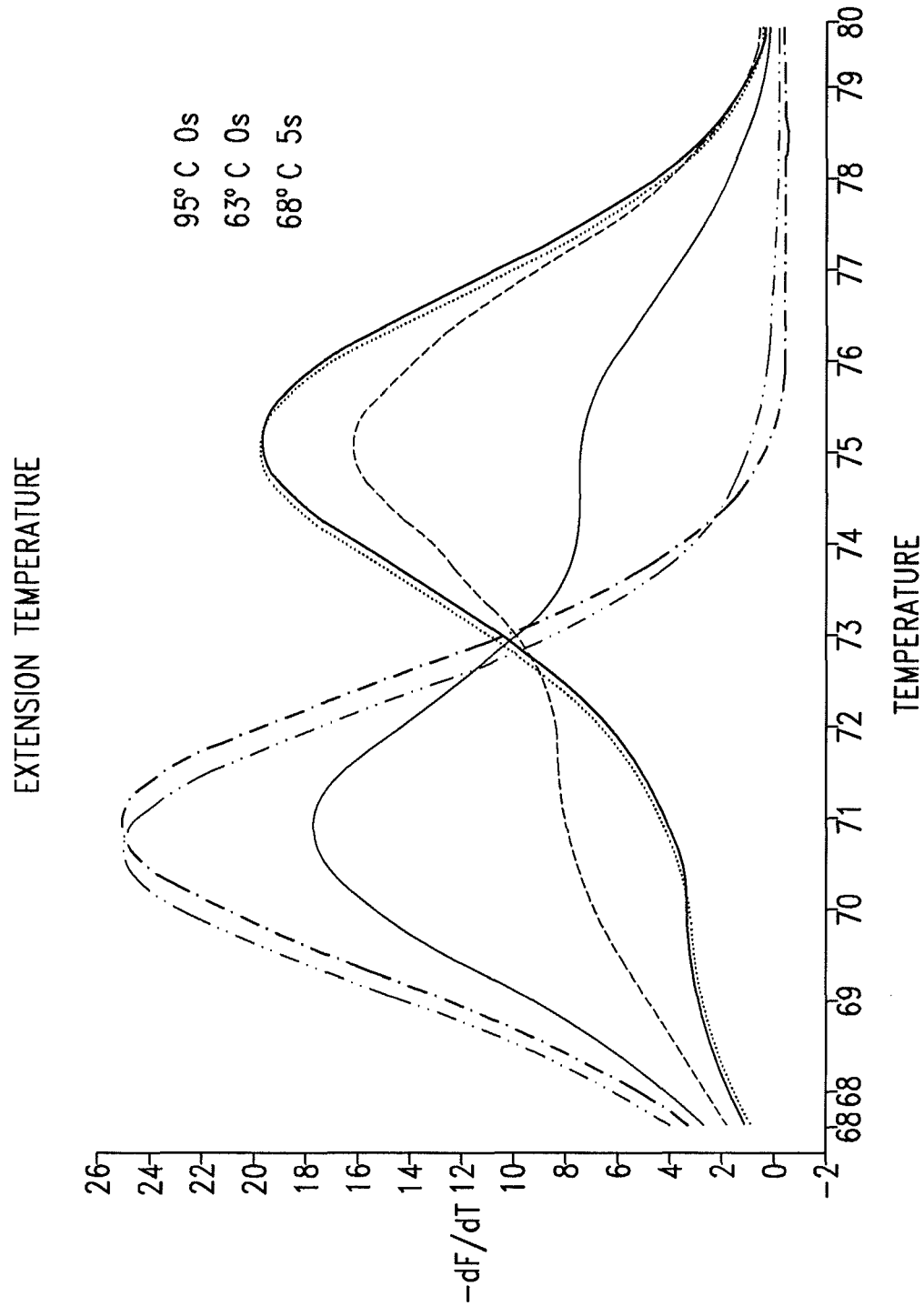

FIGS. 13a-c show the results with a 70° C. annealing temperature. This annealing temperature is approximately the same temperature as the Tm of the high Tm allele. Amplification of the high Tm homozygote is delayed only about 0.4 cycles. The melting peaks show that amplification the low Tm allele is only slightly favored.

Due to the Tm of the primers in this example, it is difficult to obtain amplification using annealing temperatures significantly above 70° C. Still, if the primers are extended to raise their Tm, it is expected that annealing temperatures above but near the high allele Tm would interfere with amplification of that allele, while not interfering with amplification of the low Tm allele, provided that the annealing temperature is under the curve of the high Tm melting peak.

In some embodiments, it may be desired only to detect the presence of the low Tm allele, which may be present in very small allele fractions. In that case, a low annealing temperature may be desired, as shown in FIG. 6b or 6b. In other embodiments, it may be desired to select an annealing temperature that favors the low Tm allele but still allows amplification of the higher Tm allele. In such embodiments, an annealing temperature at or slightly above the Tm of the low Tm allele may be desired, such as shown in FIG. 9b or 10b. Other degrees of allele bias may be desired, depending on the specific assay.

In one embodiment, the annealing temperature for a particular assay is determined by running samples at a 50:50 wildtype: mutant mix, using the Tm of the mutant allele. If allele amplification bias exists, a decrease in WT peak will be observed. If the WT peak has not decreased significantly, the annealing temperature may be dropped, illustratively in 2° C. increments, although other increments may be used, and the sample mixture re-run until complete extinction of the WT allele occurs. It is often desirable to use an annealing temperature somewhat higher than the extinction temperature. Thus, the optimized annealing temperature may be illustratively 2° C. above the extinction temperature. Appropriateness of the annealing temperature may be confirmed using serial dilutions of the mutant allele in the presence of the WT allele down to the desired sensitivity levels.

Example 6. Allele Amplification Bias Using Snapback Primers

In this example, an SNP of rs149041370 with an A/G variation is used to study allele enrichment with Snapback primers.

DNA was extracted from human blood by using a DNA-isolation kit from Puregen (Gentra Systems). DNA concentrations were quantified by NanoDrop (Thermo Scientific) and PCR crossing point. It is understood that the same PCR crossing points indicate the same concentration of DNA templates. The following primers were used:

Forward primer:
(SEQ ID NO. 10)
AGCTCAGAACTGCCTGGTGT

Reverse primer:
(SEQ ID NO. 11)
acGTTCTTTGCAGAACTGGCTGGtctctgggctgtccacacctgaa.

The probe element is shown in upper case in the Reverse primer, with the SNP site shown underlined therein. The primer is the 23 bp section on the 3'-end of the Reverse primer. The two bases shown in lower case at the 5'-end of the Reverse primer are mismatched to prevent extension when the probe element is bound in the complement amplicon. The Reverse primer tail is a perfect complement for the G allele. The amplicon size is 133 bp PCR was performed in 10 µl reaction volumes containing 1.5, 2, or 3 mmol/L MgCl$_2$, 50 mmol/L Tris (pH 8.3), 500 mg/L bovine serum albumin, 200 µmol/L of each dNTP, 0.4 units KLENTAQ polymerase (AB Peptides), 64 ng/µl Ati-Taq Monoclonal antibody (eENZYME), 0.5× LCGREEN Plus, 0.05 µm forward primer, 0.5 µm Snapback primer (reverse), and 50 ng human genomic DNA. PCR was performed in a LIGHTCYCLER (Roche) for 70 cycles with denaturing at 95° C. (0 s hold), annealing at 63° C. (0 hold), and extension at 63° C. (2 s hold). After PCR, the capillary samples were then removed from the LIGHTCYCLER, placed in the high-resolution melting instrument HR-1 (Idaho Technology), and melted from 60° C. to 92° C. with a 0.5° C./s ramp. It is understood that this PCR method, using a LIGHTCYCLER, with melting following in an HR-1, is equivalent to amplification and post-PCR melting in an LS32. Ramp speeds in the LIGHTCYCLER are comparable to the rapid cycling of the LS32 instrument.

Figure 24:
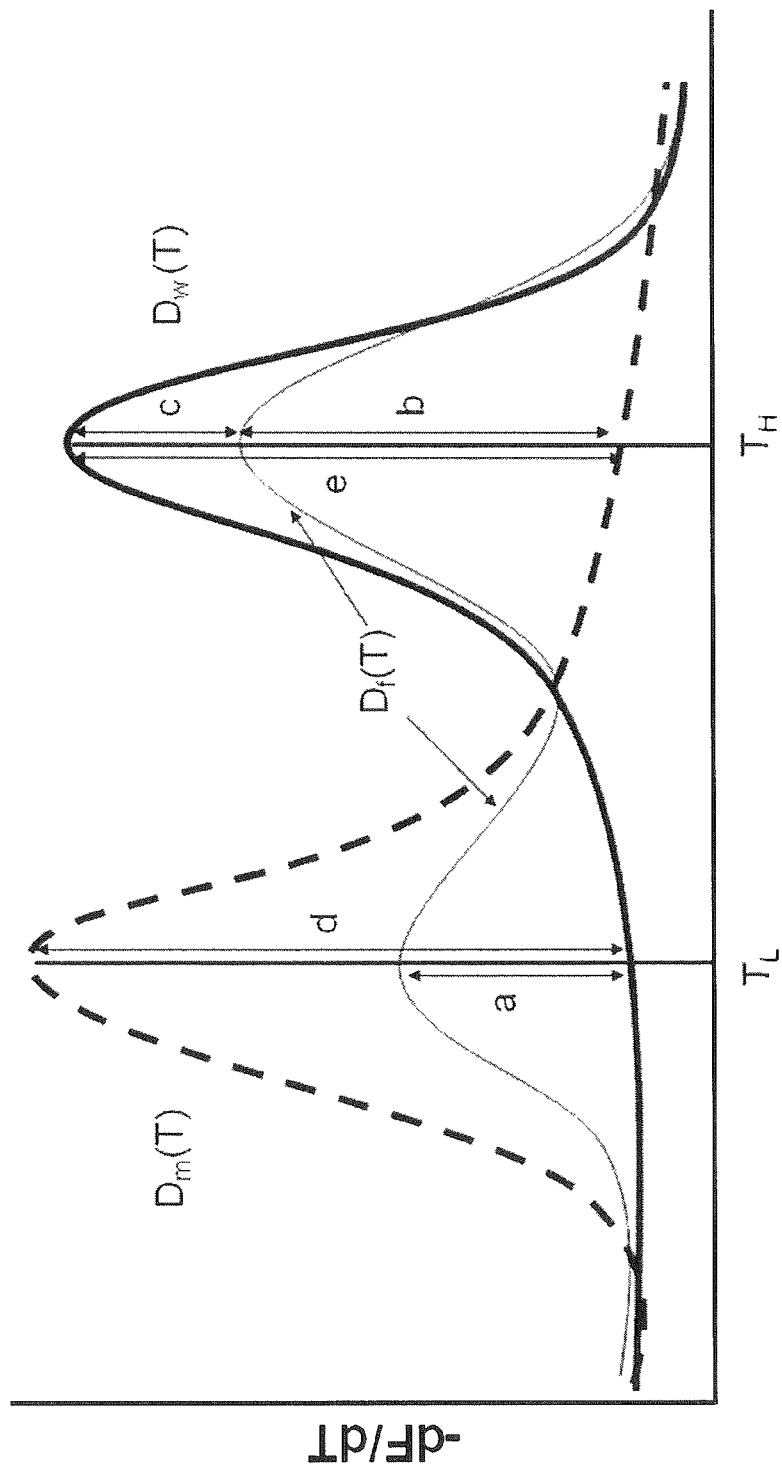
FIG. 24. shows the negative derivative of the normalized melting curves of three samples: wild-type, $D_w(T)$, homozygous mutant, $D_m(T)$, and a fractional mixed sample, $D_f(T)$. The lower and higher temperatures of the allele peaks, $T_L$ and $T_H$ are both indicated. The magnitude differences a-e are used to calculate the mutant allele fraction $F_m$ as a weighted average of two allele fraction estimates, $f(T_L)=a/d$ and $f(T_H)=c/e$, with weighting factors, $w_L=a/(a+b)$ and $w_H=b/(a+b)$. The mutant allele fraction is then calculated as $F_m=w_L f(T_L)+w_H f(T_H)=(a^2 e+bcd)/(de(a+b))$.

Melting curves were normalized using exponential background subtraction (see U.S. Patent Application No. 2009-0222503, herein incorporated by reference), and differentiated using Savitzky-Golay fitting (Palais R, Wittwer C T. Methods Enzymol 2009; 454:323-43). In one embodiment, allele fractions for a particular protocol are calculated by weighted peaks heights as illustrated in FIG. 24. Specifically, $D_w(T)$ is the negative derivative of the normalized melting curve of a wild type sample, $D_m(T)$ is the negative derivative of the normalized melting curve of a 50:50 homozygous mutant sample, and $D_f(T)$ is the negative derivative of the normalized melting curve of a fractional mixture of the two. If the snapback probe element matches the wild type allele, $D_m(T)$ will have a peak at a low temperature $T_L$ and $D_w(T)$ will have a peak at a high temperature $T_H$ with $T_L<T_H$. $D_f(T)$ typically exhibits two peaks corresponding to melting of the mismatched allele at $T_L$ and the matched allele at $T_H$. The mutant allele fraction is calculated as the weighted average of two estimates as $F_m=w_Lf(T_L)+w_Hf(T_H)$ where $w_L$ and $w_H$ are the weights and $f(T_L)$ and $f(T_H)$ are the individual estimates at each temperature peak. The weights are determined by the relative magnitudes of the mixed sample above the baselines of the unmixed samples to favor the larger peak: $w_L=a/(a+b)$ and $w_H=b/(a+b)$ (FIG. 24). The individual estimates $f(T_L)$ and $f(T_H)$ are obtained proportionally at each temperature: $f(T_L)=a/d$ and $f(T_H)=c/e$. Therefore $F_m=(a^2e+bcd)/(de(a+b))$. It is understood that if the protocol changes to affect the heterozygote peak heights (e.g. a change in annealing temperature, Mg$^{++}$ concentration, extension time, etc.), the values of a, b, c, d, and e will change, and the equation is valid for that specific 50:50 heterozygote curve shape. Thus, the formula provides an adjustment to calculate back to the starting concentration of each allele. It is understood that allele fractions according to any of the embodiments described herein may be calculated using this or other methods, such as by comparison to a dilution series. Other methods are known in the art. See U.S. Patent Application No. 2003-0104438, herein incorporated by reference. Further information on methods for calculating allele fractions are presented below in Example 9.

Effects of Rare Allele Enrichment During PCR

Figure 17A:
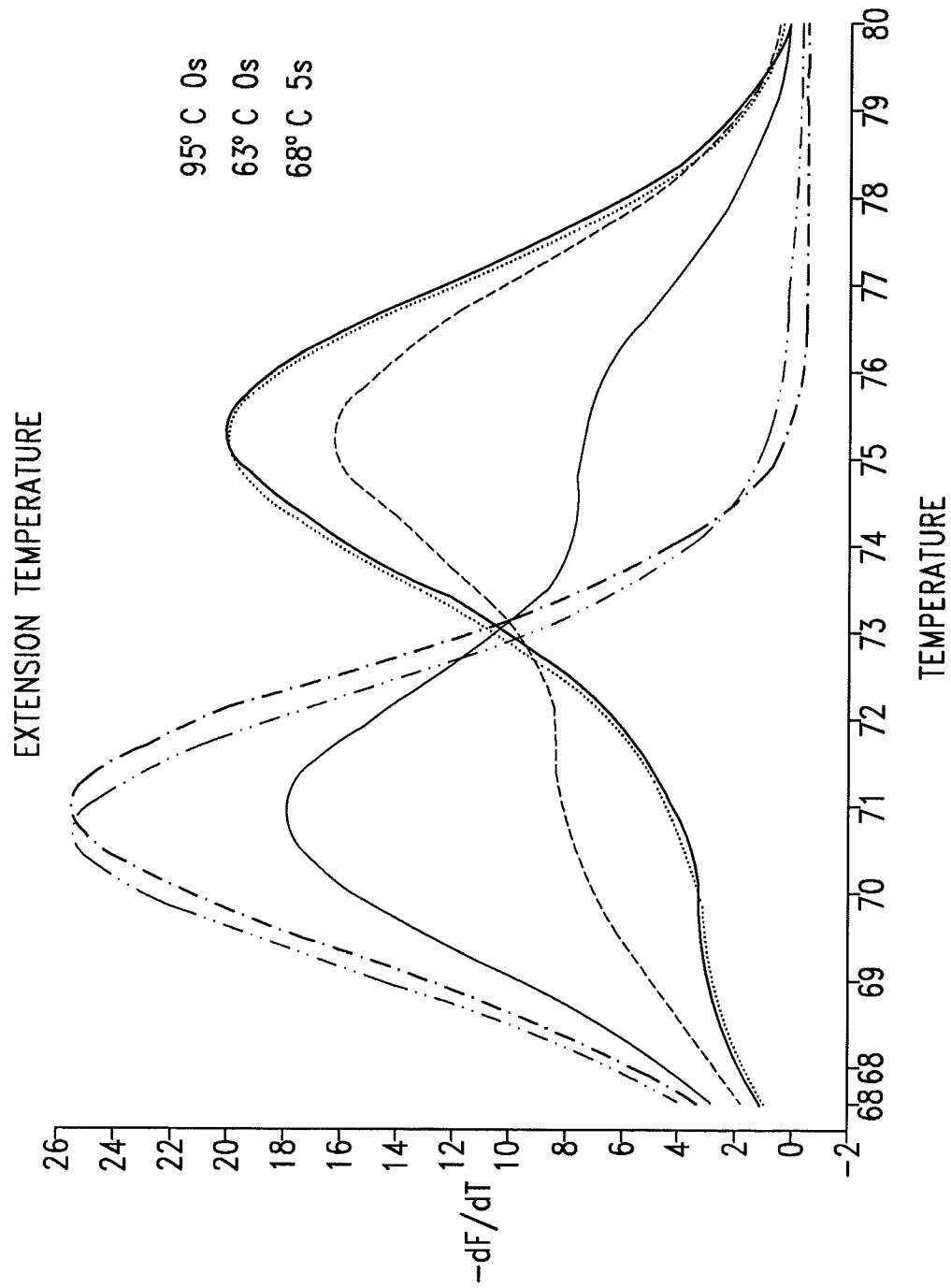
FIGS. 17a-b are similar to FIGS. 14a-d, except using different extension times ((———)=1A:10G; (------)=1A:100G; (— — —)=1A:1000G; (—··—··—)=A:G; (········)=G; (—·—·—)=A).
Figure 17B:
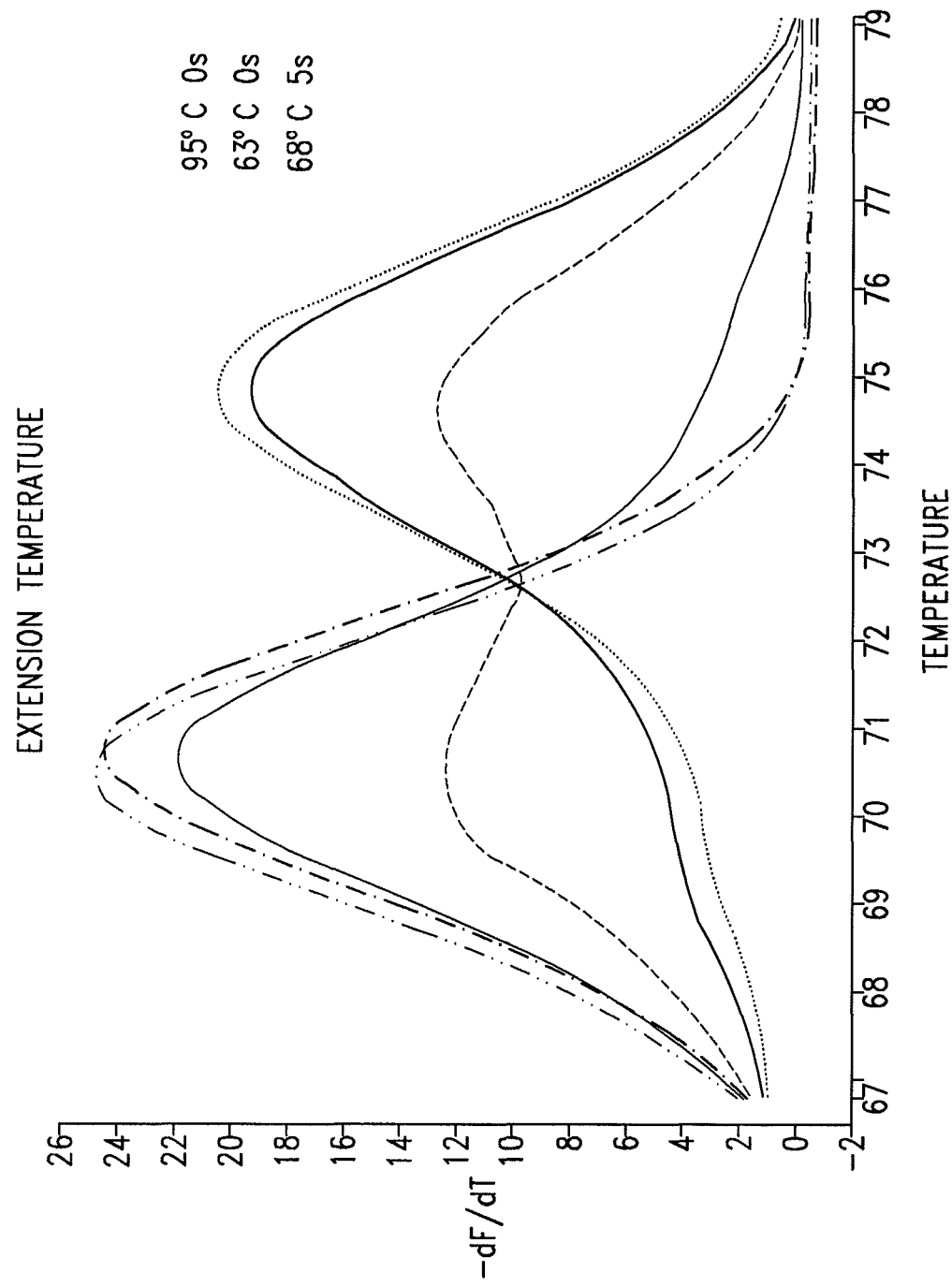
Figure 18A:
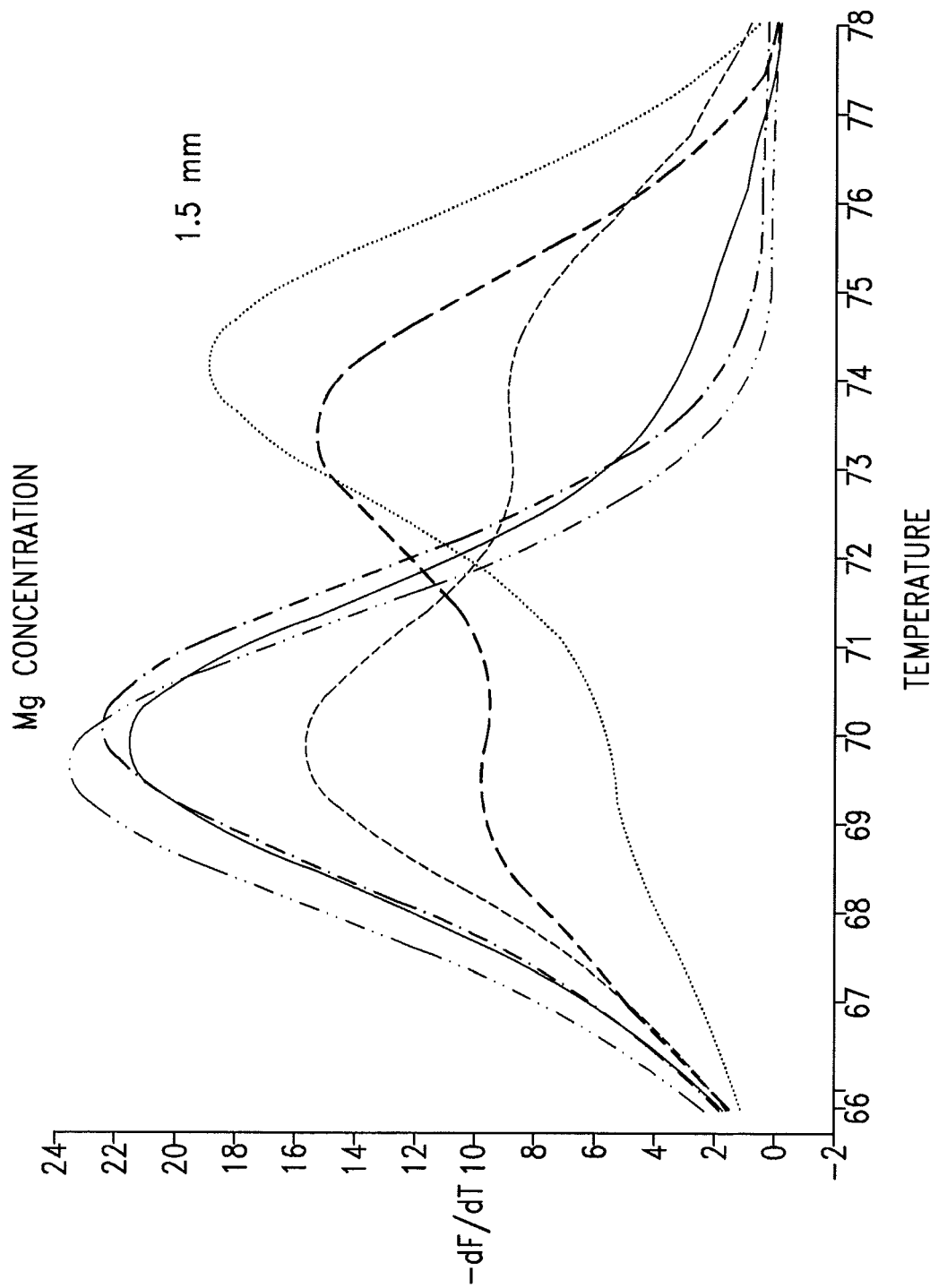
FIGS. 18a-c are similar to FIGS. 14a-d, except using different magnesium concentrations ((———)=1A:10G; (------)=1A:100G; (— — —)=1A:1000G; (—··—··—)=A:G; (········)=G; (—·—·—)=A).
Figure 18B:
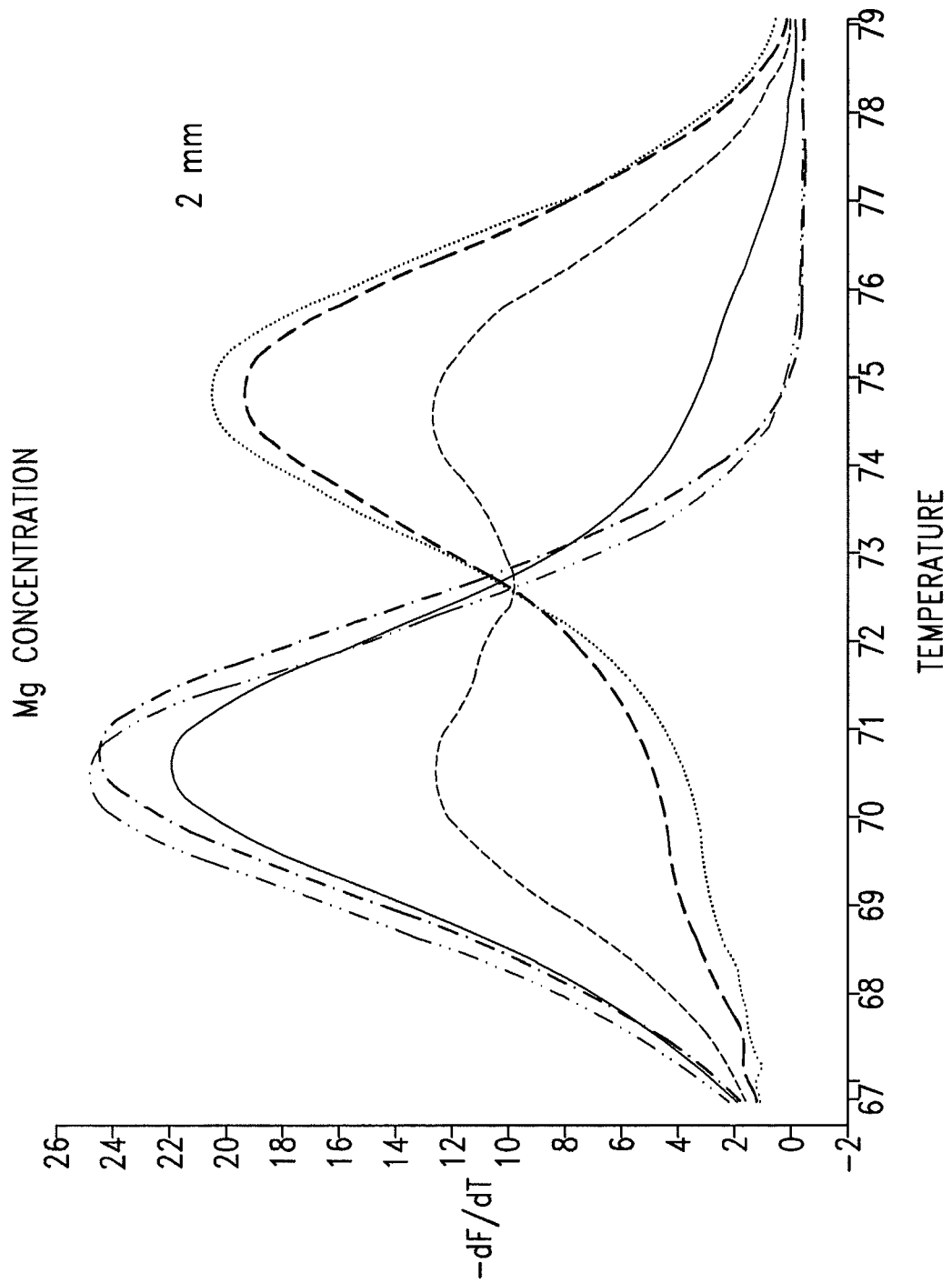
Figure 18C:
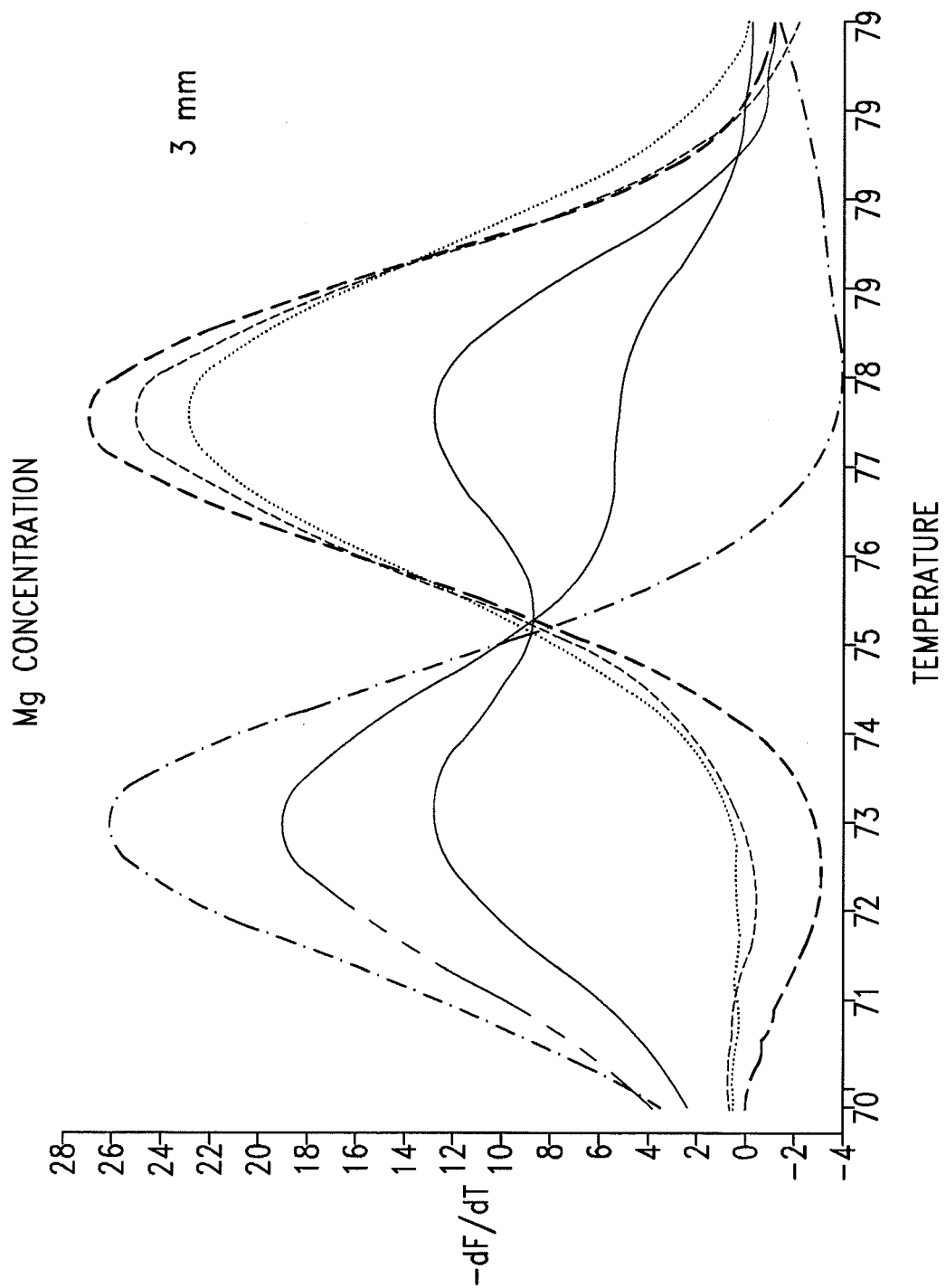
Figure 19A:
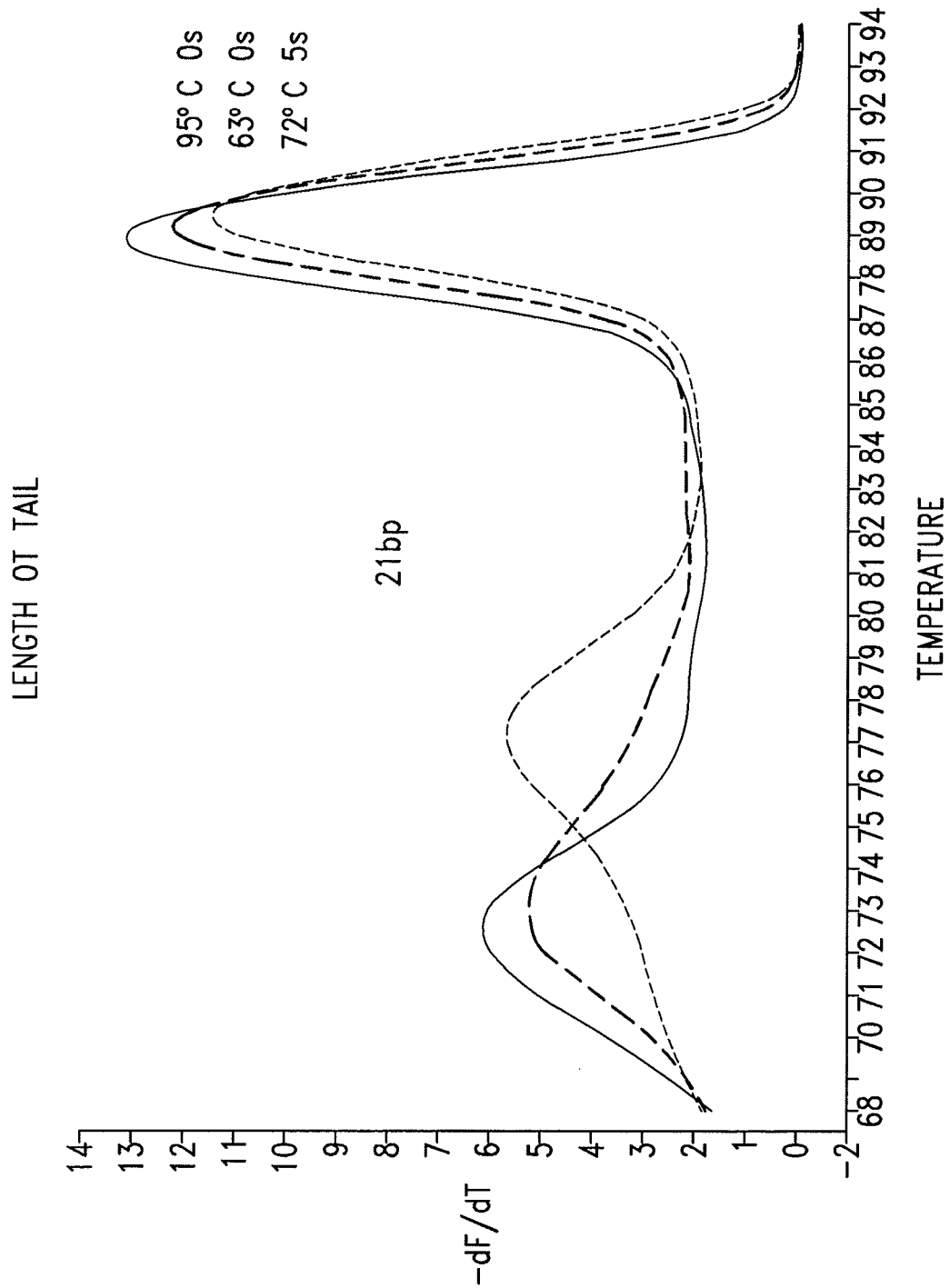
FIGS. 19a-d are similar to FIGS. 14a-d, except showing probe elements having different lengths ((———)=A; (------)=G; (— — —)=A:G).
Figure 19B:
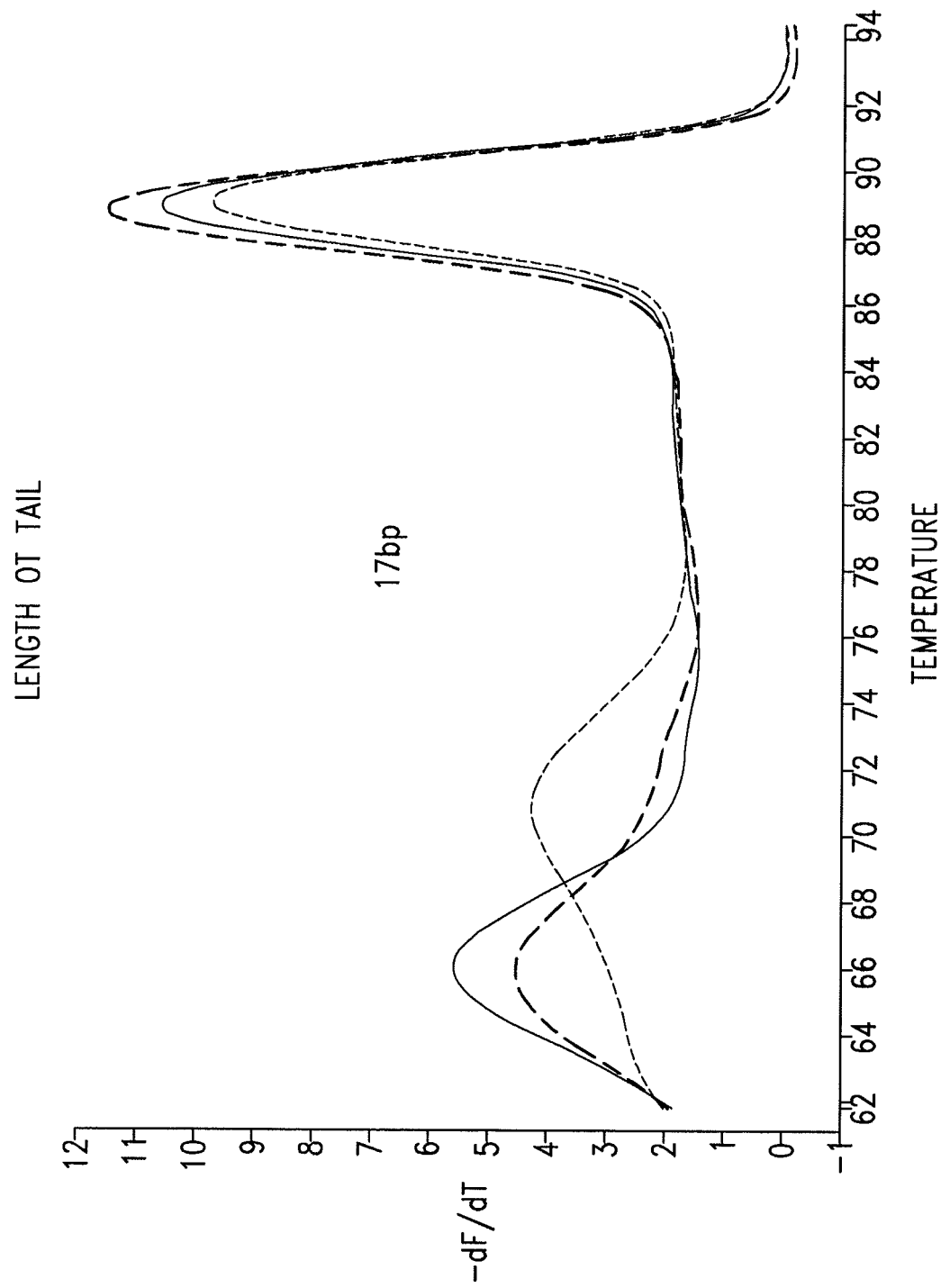
Figure 19C:
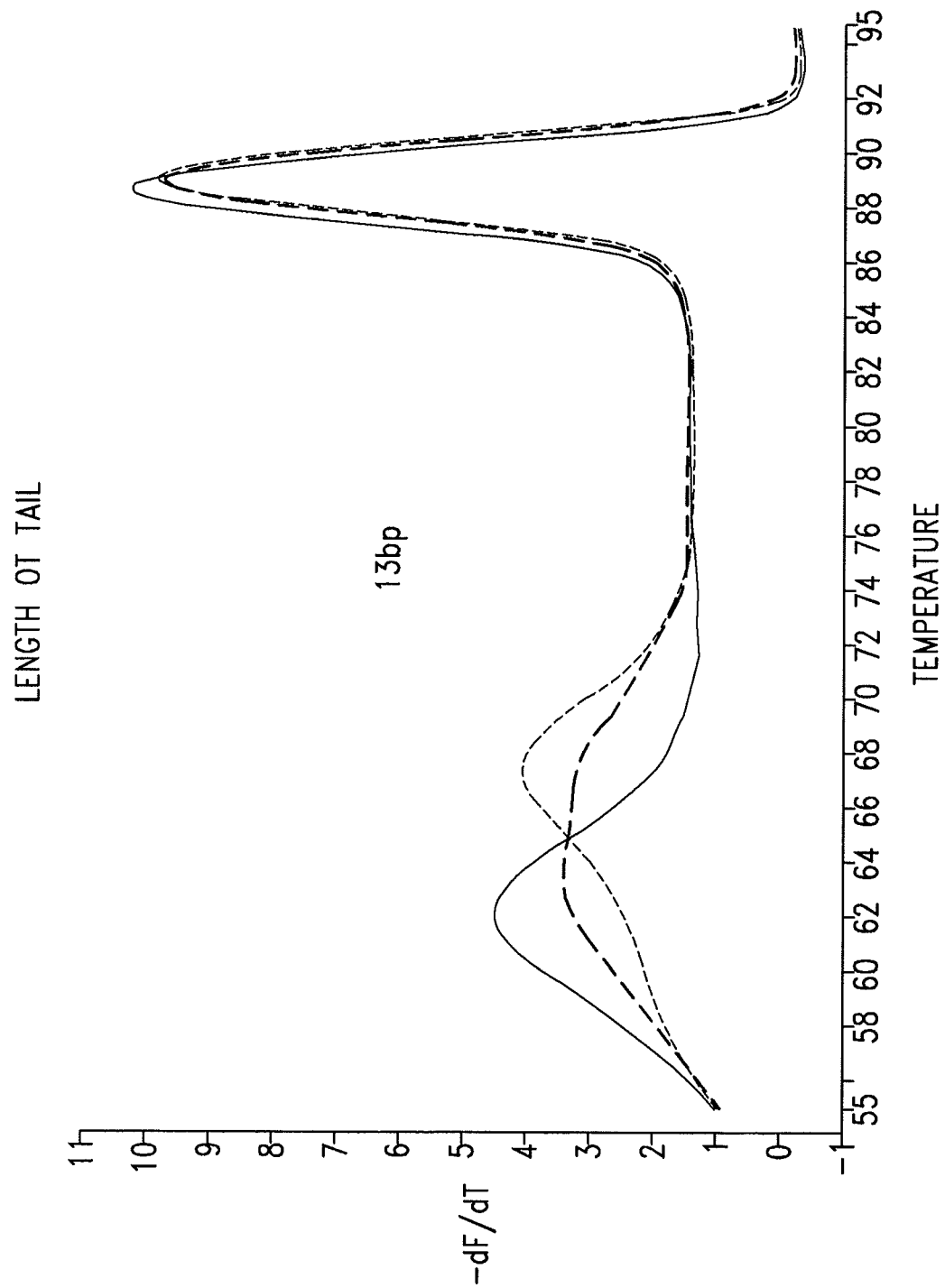
Figure 19D:
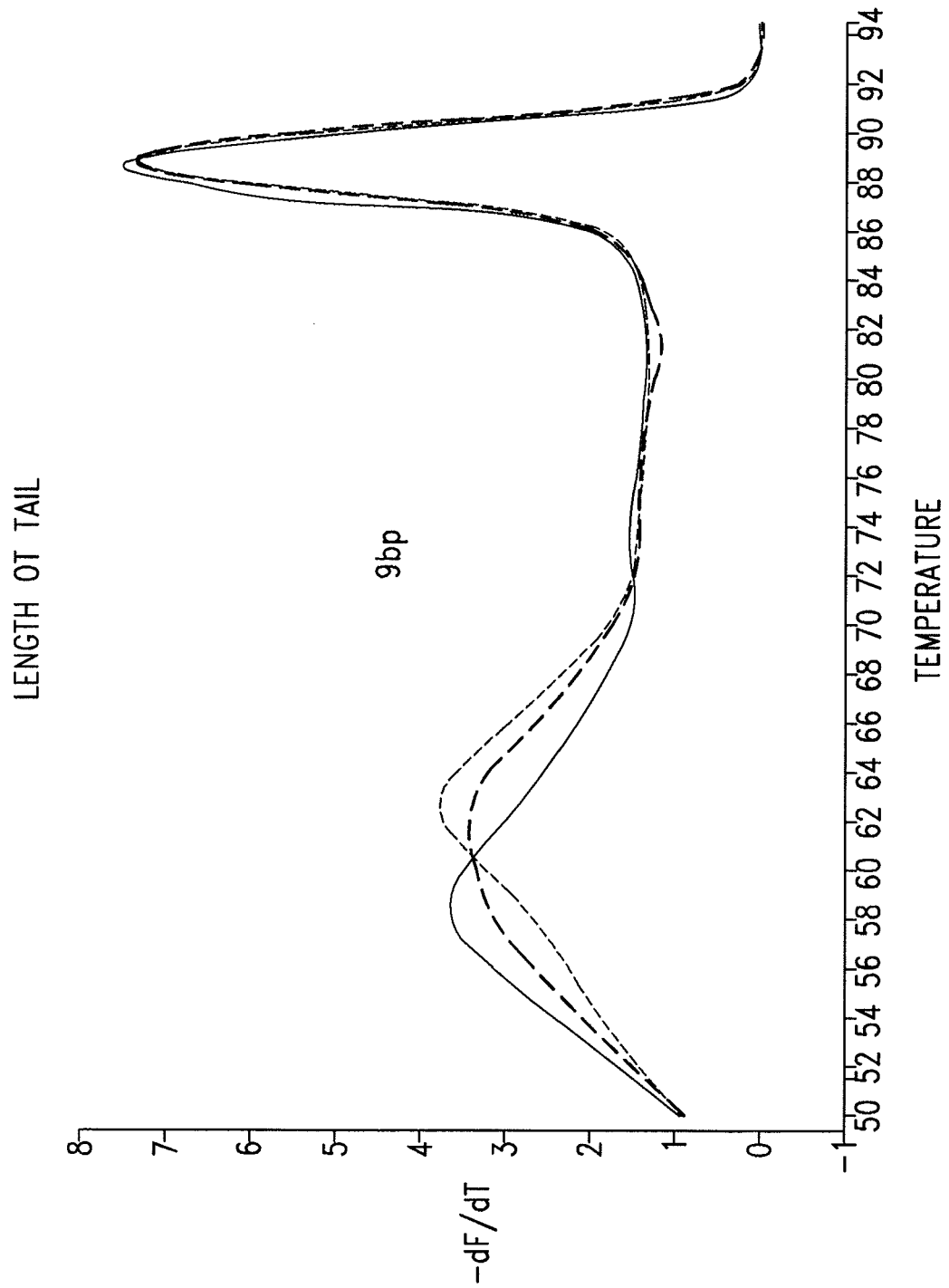

1. Denature temperature: PCR was performed with a denaturation temperature of 95° C., 90° C., 89° C. or 88° C. As seen in FIGS. 14a-d, a denaturation temperature of 95° C. vs. 90° C. had no effect on enriching the mismatch peak. 88° C. was too low of a denaturation temperature, and the template did not amplify well.
2. Annealing temperature: In FIGS. 15a-d, the denaturation temperature was maintained at 95° C. and extension at 76° C., while the annealing temperature was at 55° C., 58° C., 61° C., or 63° C. As was found with unlabeled probes, the annealing temperature did not have any effect on the allele amplification ratio when the extension temperature is kept near the Tm of the matched allele.
3. Extension temperature: In FIGS. 16a-d, the denaturation temperature was maintained at 95° C. and annealing temperature at 63° C., while the extension temperature was 74° C., 72° C., 70° C., or 68° C. As was found with unlabeled probes, the lower the extension temperature (to temperatures around that of the matched probe Tm), the more the amplification enriches the mismatch allele.
4. Extension time: FIGS. 17a-b show that with a shorter extension time, decreasing from 5 s to 1 s, the mismatch allele enriched significantly. With the 68° C. extension temperature and the 1 second extension time, in the 1:1 and 1:10 mixtures the amplification product is now mostly the A allele, and in the 1:100 mixture, the amplification product is now about 50% of each allele. The 1:1000 mixture is noticeably different from the pure G allele. Thus, the degree of allele enrichment is strongly related to the PCR extension time. As summarized in FIG. 26a, when the extension time was 20 seconds (typical of conventional PCR) samples with a ratio of 1:1000 (mutant to wild type) did not enrich sufficiently for detection. However, as the extension time is reduced, these rare alleles become easy to detect. In the extreme case with an extension time of 0 seconds, the resulting fraction of the mutant allele was increased from 0.1% (1:1000) to 29%. The improved sensitivity of short extension times has the added advantage of accelerating the completion of PCR, illustratively to only 20 to 25 minutes (~20 s/cycle).
5. Mg concentration: In FIGS. 18a-c, cycling conditions from step 4 above were used, and the Mg concentrations were 1.5 mM, 2 mM, and 3 mM. The lowest magnesium concentration (1.5 mm Mg buffer) provided good amplification of the minor allele in the 1:1000 mixture. The highest magnesium concentration appeared to result in essentially even amplification of the major and minor alleles. FIG. 26b summarizes further work with free Mg$^{++}$ concentrations ranging from 2.2 mM to 0.8 mM, with a 1:1000 ratio of mutation to wild type template. The apparent mutation fraction increased from undetectable to 48% as the Mg$^{++}$ concentration was lowered. One explanation may be that a lower Mg$^{++}$ concentration increases heterozygote amplification, thus increasing the heteroduplex ratio. Another explanation may be that the mutation allele does not form a hairpin at the lower Mg$^{++}$ concentration, thus allowing the mutation allele to amplify more readily.

6. Tail length: The tail lengths (probe elements) were varied, using 9 bp (Tm 64° C.), 13 bp (Tm 72° C.), 17 bp (Tm 74° C.) and 21 bp (Tm 77° C.). Longer tails have higher Tm and, as seen in FIGS. 19a-d, the higher Tm enriches the mismatch allele. When shorter tails are used, it is possible to obtain enrichment of the minor allele by lowering the extension temperature to below the Tm of the matched allele, provided that the extension temperature is not lowered below the effective temperature of the polymerase.

Figure 20A:
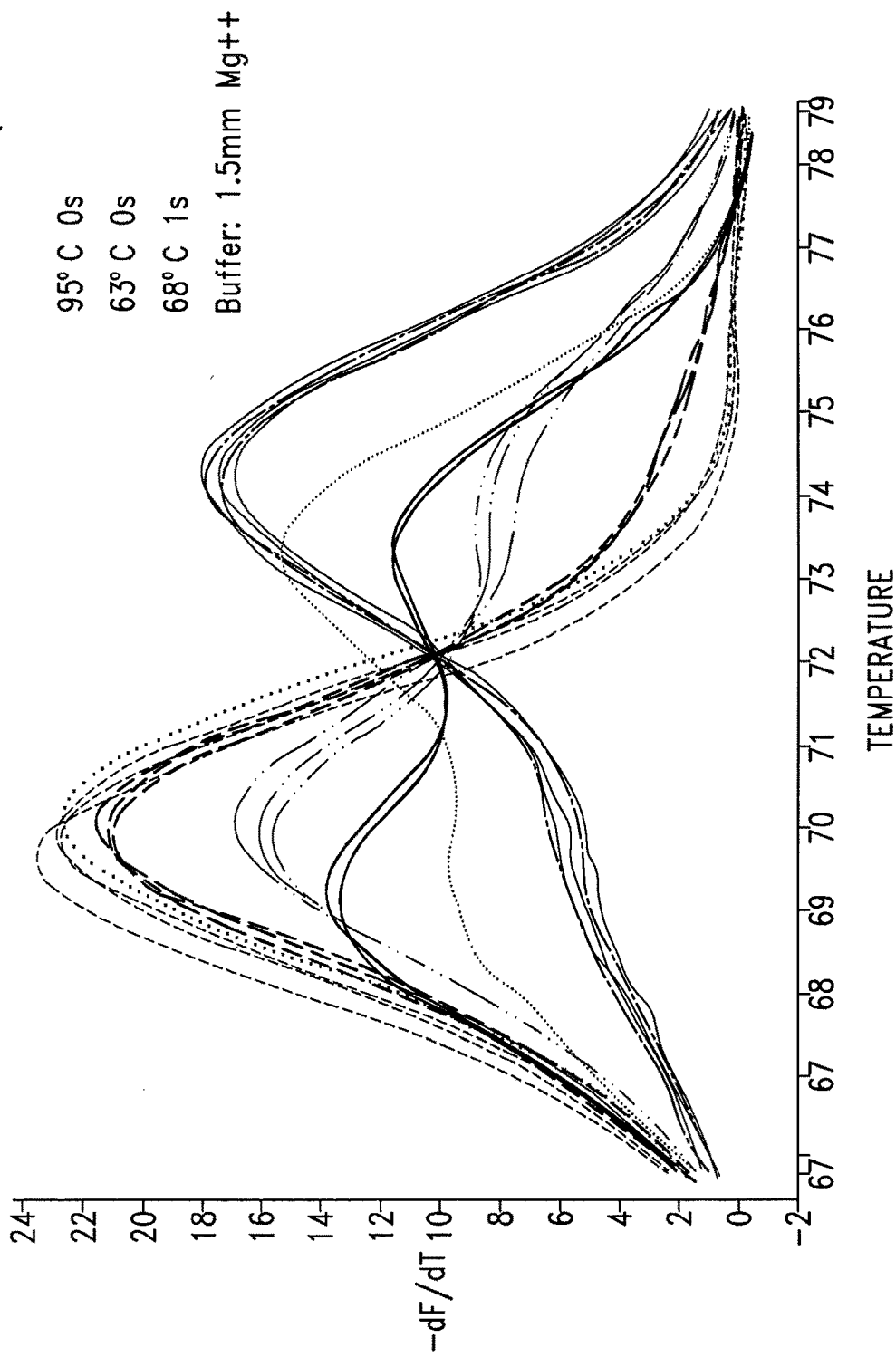
FIGS. 20a-b show triplicate runs similar to FIG. 20a ((—·—·—)=1:10000; (········)=1:1000; (—··—··—)=1:100; (— — —)=1:10; (------)=A:G; (———)=G; (········)=A).
Figure 20B:
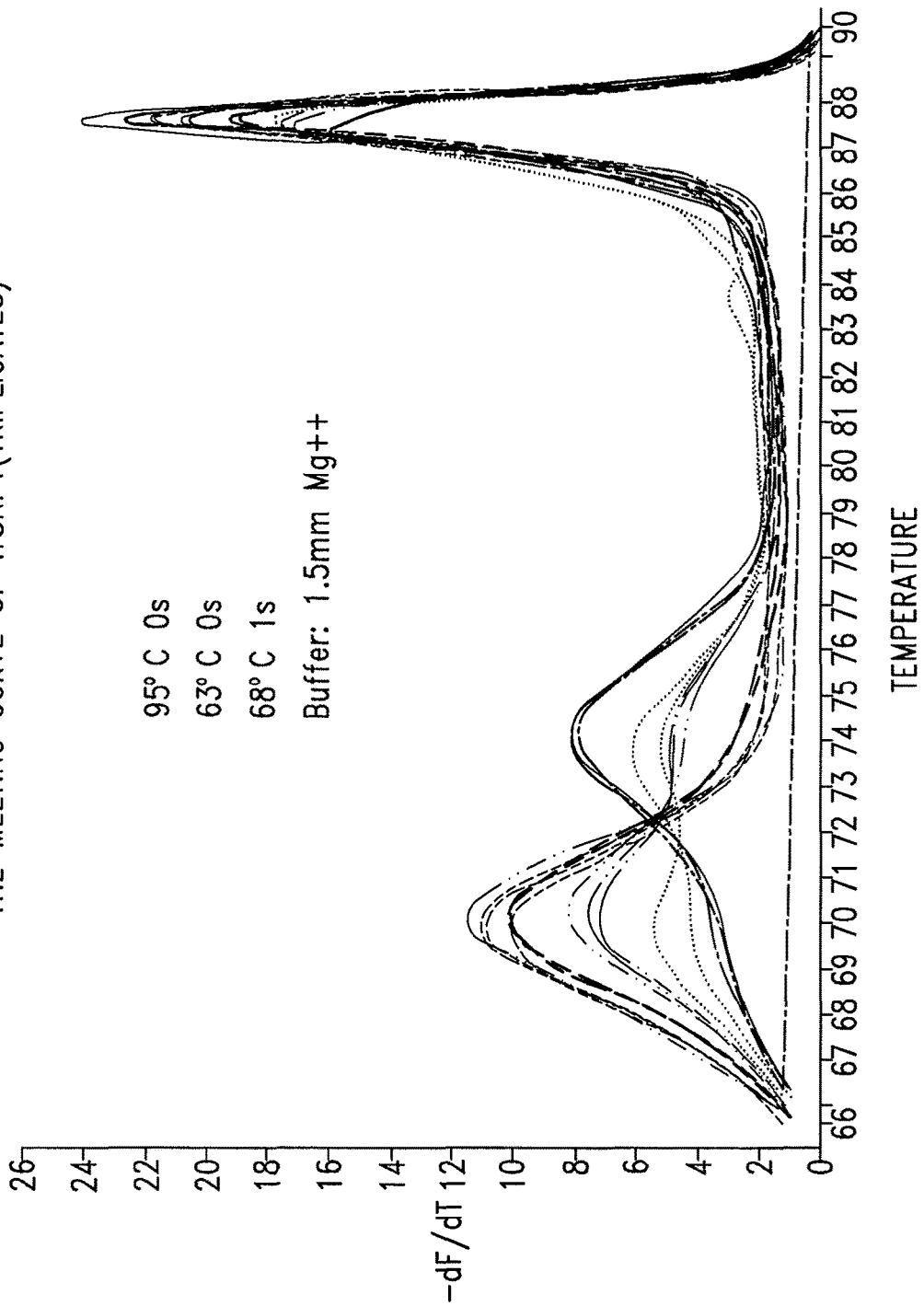

The results shown in FIGS. 14-19 are consistent with the results shown above for the unlabeled probes. In this Example, separate annealing and extension temperatures were used, but when extension temperatures were chosen such that most or all of the matched probe element is bound and most of the mismatched probe element is melted off, then the mismatched allele is preferentially amplified. FIG. 16 shows that, as the extension temperature is lowered, amplification of the mismatched allele is increasingly favored. Further, in this Example, with Snapback primers it has also been found that short extension time and lower Mg concentration favors amplification of the mismatched allele, such that a DNA ratio of 1:1000 or even greater can be analyzed, as can be seen in FIG. 20. It is expected that these effects would also been seen with unlabeled probes and other probes according to this invention.

Figure 25:
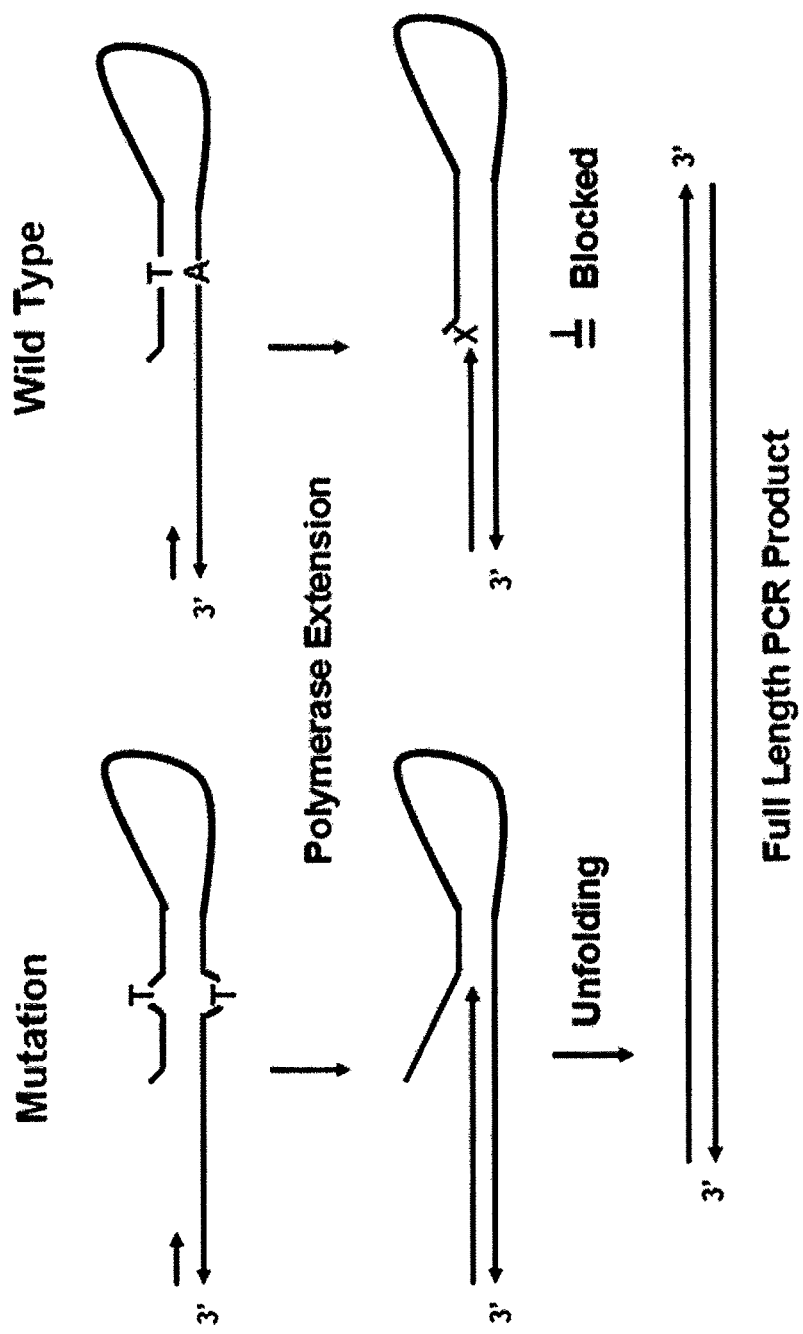
FIG. 25 diagrams the Snapback probe element with both a mismatch to the mutant (or minor) allele and to the wild type (or major) allele. If the PCR extension conditions are carefully chosen, the polymerase is free to extend the destabilized mutant hairpin, but wild type extension is hindered, resulting in enrichment of the mutant allele.

Without being bound by any particular theory, it is believed that amplification using Snapback primers favors the mismatched allele for the reasons discussed above with respect to unlabeled probes. However, since Snapback primers form intramolecular loop structures, it is believed that not only will the matched probe section interfere with extension in an intermolecular interaction with another target sequence or where the loop is downstream (as with amplification of an amplicon using the forward primer discussed above), but will also interfere with annealing of the Snapback (reverse) primer to the looped amplification product. The probable mechanism of allele enrichment by snapback primers is shown in FIG. 25. The Snapback probe element is mismatched to the mutation allele, destabilizing the hairpin and allowing the polymerase to unfold the secondary structure and complete extension of the full length PCR product (FIG. 25, left). However, the Snapback probe element is completely matched to the wild type allele, blocking extension with a more stable hairpin and preventing formation of the full length PCR product (FIG. 25, right). Since differential amplification depends on the relative hairpin stability resulting from a single mismatch, successful enrichment is likely to depend on amplification conditions, including displacement activity of the polymerase, the annealing temperature relative to the hairpin stability and the extension time. It is believed that Snapback primers may be able to bias amplification of the mismatched allele to an extent greater than that of unlabeled probes. Finally, it has been found that an exo+ polymerase is more compatible with allele enrichment using Snapback primers than it is with unlabeled probes. This may be due to the 5' mismatch on the probe element.

Example 7. Blind Tumor Identification Using Snapback Primers

Thyroid nodules are rather common and found in about 5% of women and in 1% men, whereby more than 90% are benign hyperplastic nodules or follicular adenomas. If malignant, the diagnosis is usually papillary thyroid carcinoma, PTC. Often, one of the 15 chimeric mRNAs involving the proto-oncogene RET, a tyrosine-kinase, is cited as the cause for PTC. Both medullary thyroid cancer and papillary thyroid cancer are strictly linked to activating mutations in the RET gene. RET rearrangements, caused by chromosomal inversions or translocations, are present in 20-40% of cases of PTC. However, recently a somatic mutation of the BRAF gene, c.1799 T>A, causing a Valine to Glutamate substitution, p.V600E, was cited as the most common change in PTCs resulting in more than 80% of thyroid cancers. This amino acid substitution leads to the constitutive activation and de-regulation of the mitogen-activated protein kinase (MAPK) pathway. In this example, the point mutation of the B-raf mutation V600E (T→A) is studied.

B-raf V600E homozygote mutation DNA was extracted from human cell line HTB-72 (ATCC) by using a DNA-isolation kit from Puregen (Gentra Systems). DNA concentrations were quantified by NanoDrop (Thermo Scientific) and adjusted by using the PCR crossing point. 47 pairs of pre-tested tumor tissue and needle thyroid nodule DNA samples were provided by ARUP (Salt Lake City, Utah) for a blind test (Leslie R Rowe, et al. *CytoJournal* 2006, 3:10). The following primers were used, with the same notation as in Example 6:

```
Forward primer:
                                    (SEQ ID NO. 12)
tgttttcctttacttactacacctcag Reverse primer:
                                    (SEQ ID NO. 13)
aaTCTAGCTACAGTGAAATCTCGATGtcag tggaaaaatagcctcaattc
```

The amplicon size is 145 bp.

PCR was performed in 10 µl reaction volumes containing 2 mmol/L MgCl$_2$, 50 mmol/L Tris (pH 8.3), 500 mg/L bovine serum albumin, 200 µmol/L of each dNTP, 0.4 units KLENTAQ polymerase (AB Peptides), 64 ng/µlAti-Taq Monoclonal antibody (eENZYME), 0.5=LCGREEN Plus, 0.05 µm forward primer, 0.5 µm Snapback primer (reverse), and 50 ng human genomic DNA. PCR performed in a LIGHTCYCLER (Roche) for 70 cycles with denaturing at 95° C. (0 s hold), annealing at 52° C. (0 hold), and extension at 64° C. (0 s hold). After PCR, the capillary samples were then removed from the LIGHTCYCLER, placed in the high-resolution melting instrument HR-1, and melted from 60° C. to 88° C. with a 0.5° C./s ramp.

Figure 21A:
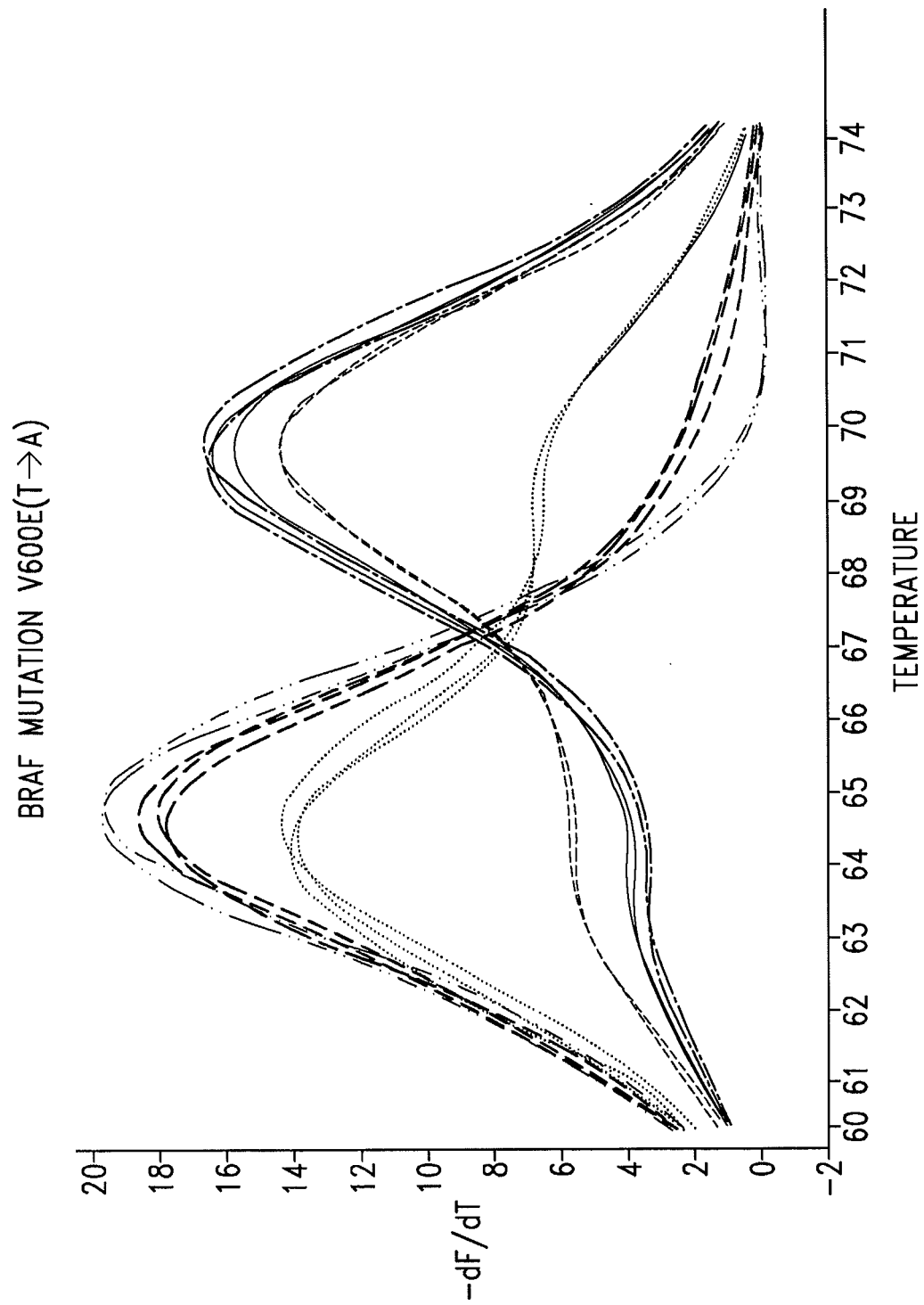
FIGS. 21a-b show melting of the B-raf mutation V600E amplicon subsequent to amplification using a Snapback primer ((—·—·—)=wt; (—··—··—)=B-raf mutation; (———)=1:1000; (------)=1:100; (········)=1:10; (— — —)=1:1).
Figure 21B:
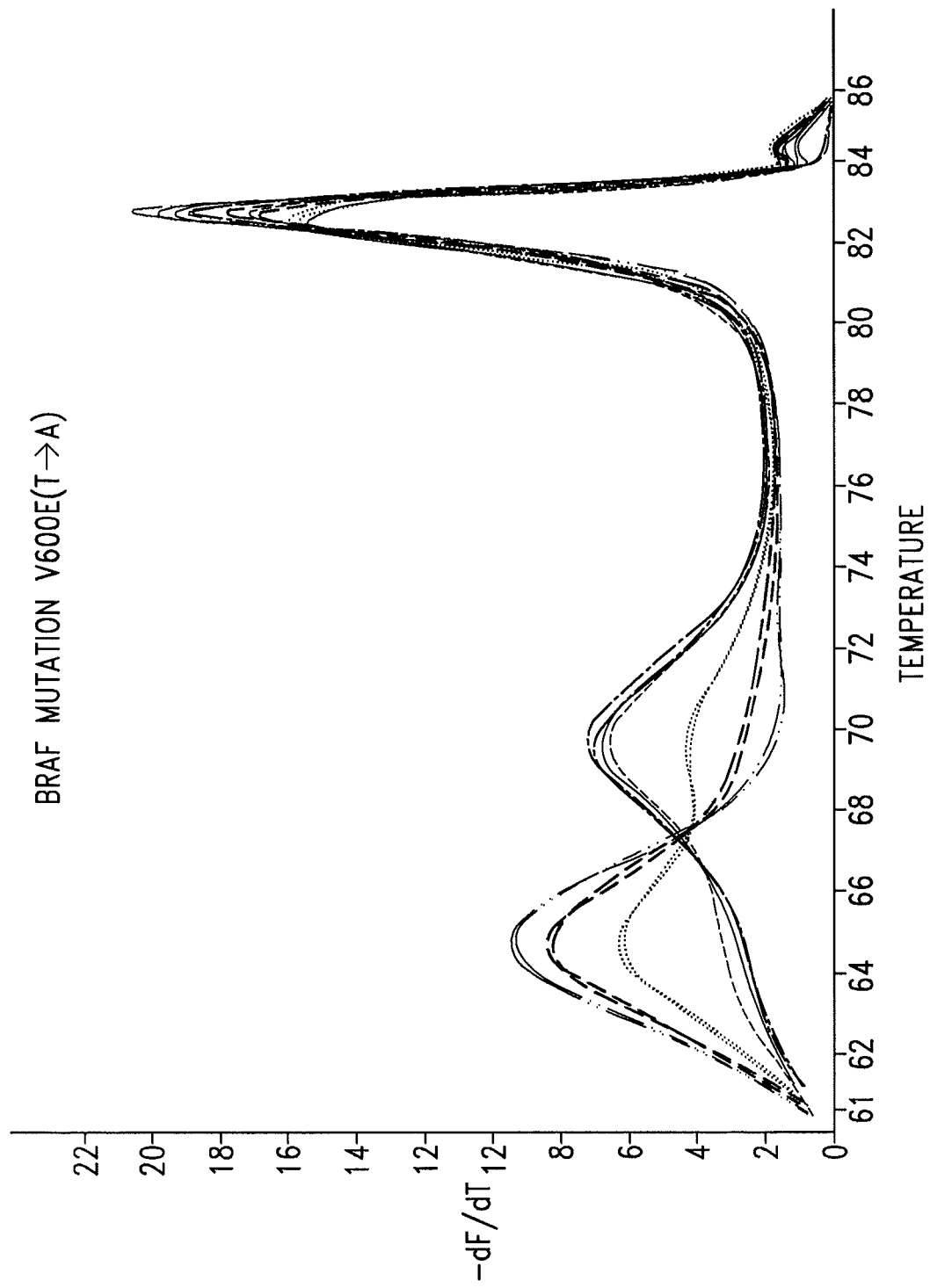

For comparison, the same forward primer was used with the primer element from the reverse primer above (tcagtggaaaaatagcctcaattc (SEQ ID NO. 14)) in standard symmetric PCR to amplify a 183 bp amplicon in standard symmetric PCR. Using this standard PCR, one could detect B-raf mutation-to-wild type DNA ratio of 1:25, while the Snapback primer PCR protocol outlined in the above paragraph can enrich PCR to detect 1:100 (FIGS. 21a-b). The results were confirmed using sequencing.

Figure 22:
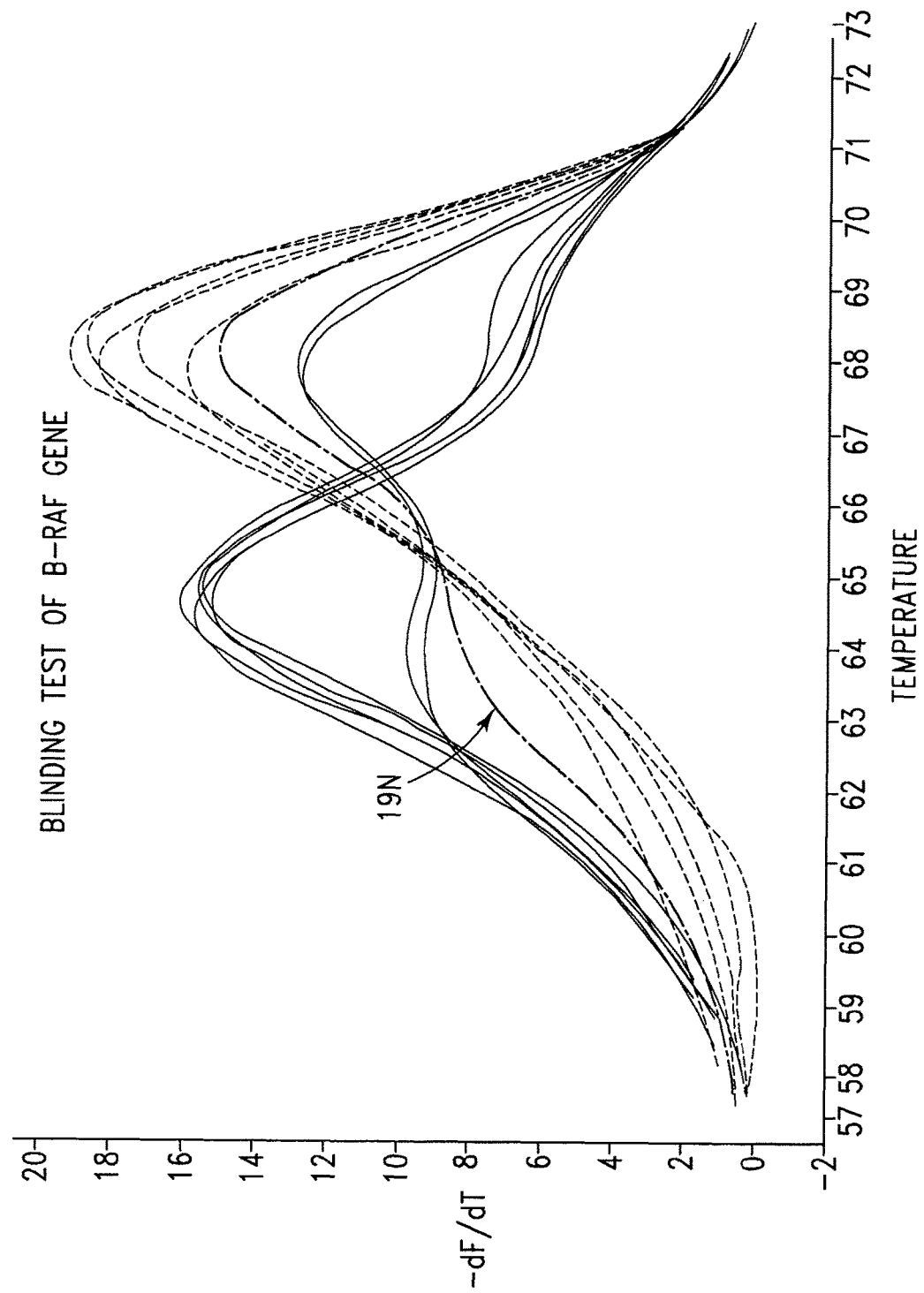
FIG. 22 shows the melting results of a blind study of the B-raf mutation.

After blinded analysis, all samples were concordant except for 2 samples that were positive by snapback primers but negative by hybridization probes. One needle sample contained V600E in an amount less than 1%. Such a small frequency cannot be detected by standard PCR, but as seen as the (— — — —) line ((— — — —) is 1:100 control) in FIG. 22, this is detectable by Snapback primer enrichment.

Example 8. Small Deletion Detection Using Snapback Primers

Somatic mutations in the epidermal growth factor receptor (EGFR) have been detected in patients with non-small cell lung cancer (NSCLC) and are associated with sensitivity to treatment with the drugs Gefitinib or Erlotinib. Two of the most common types of somatic EGFR mutations are exon 19 small deletions and the L858R point mutation (accounting for about 85%). In this Example, the EGFR exon19 is used to show that Snapback primer enrichment method could detect small deletion.

EGFR homozygote mutation E746-A750 DNA was extracted from human cell line CRL-5883 (ATCC) by using DNA-isolation kit from Puregen (Gentra Systems). DNA concentrations were quantified by NanoDrop (Thermo Scientific) and adjusted by using the PCR crossing point. The following primers were used, with the same notation as in Example 6:

```
Forward primer:
                                        (SEQ ID NO. 15)
TGGATCCCAGAAGGTGAGAA Reverse primer:
                                        (SEQ ID NO. 16)
ccAGAGAAGCAACATCTCCGAAAGagcagaaactcacatcgagga
```

As above, the probe element matches the wild type. The wild type amplicon size is 131 bp in the wild type. Several deletions were studied, both of which partially overlaps the probe element.

PCR was performed in 10 µl reaction volumes containing 2 mmol/L MgCl$_2$, 50 mmol/L Tris (pH 8.3), 500 mg/L bovine serum albumin, 200 µmol/L of each dNTP, 0.4 units KLENTAQ polymerase (AB Peptides), 64 ng/µlAti-Taq Monoclonal antibody (eENZYME), 0.5× LCGREEN Plus, 0.05 µm forward primer, 0.5 µm Snapback primer (reverse), and 50 ng human genomic DNA. PCR was performed in a LIGHTCYCLER (Roche) for 70 cycles with denaturing at 95° C. (0 s hold), annealing at 55° C. (0 hold), and extension at 64° C. (0 s hold—detection at this temperature for a 0.2° C. hold per sample). After PCR, the capillary samples were then removed from the LIGHTCYCLER, placed in the high-resolution melting instrument HR-1 (Idaho Technology), and melted from 60° C. to 88° C. with a 0.5° C./s ramp.

Figure 23:
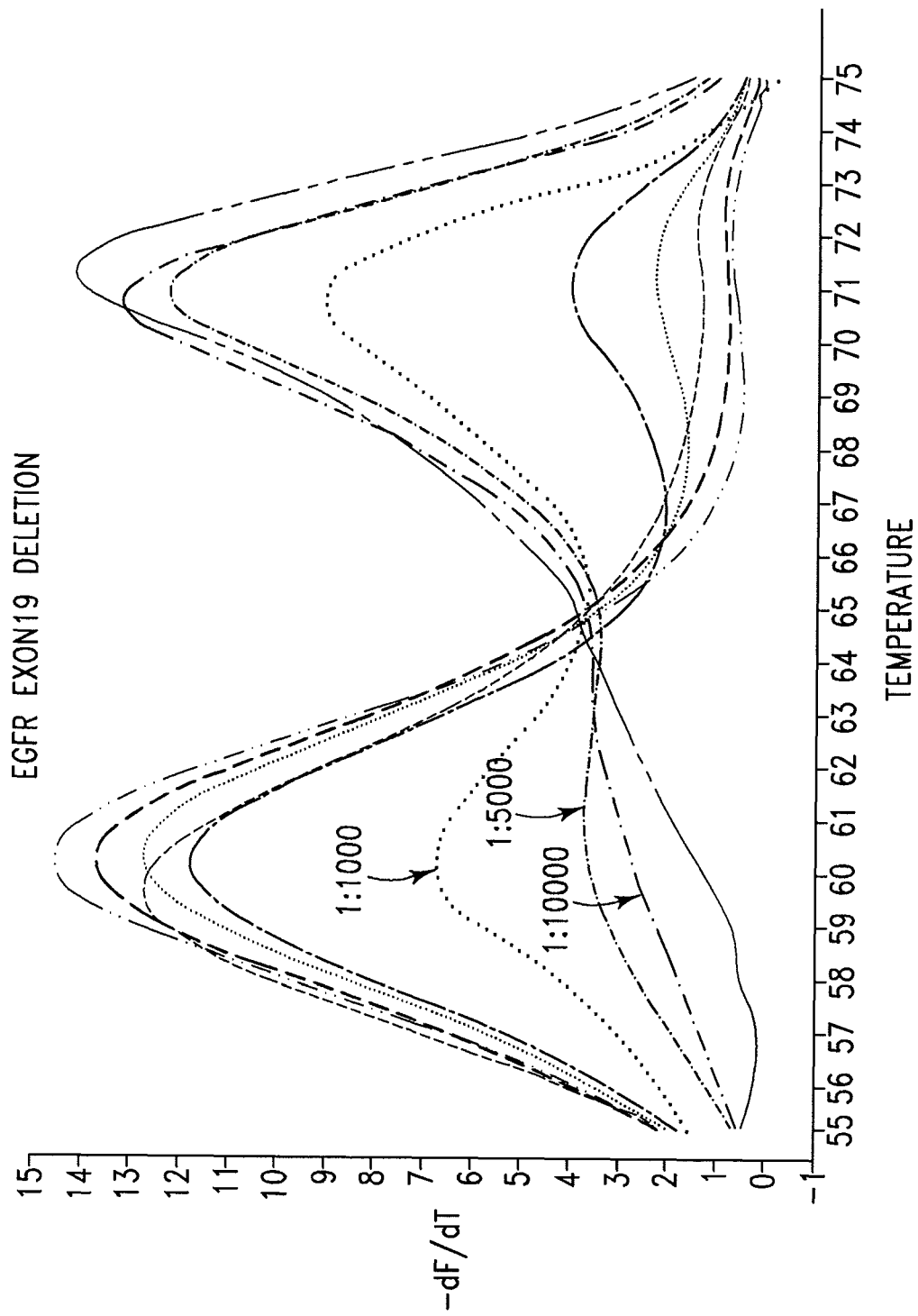
FIG. 23 shows melting curve analysis of the EGFR exon 19 deletion, subsequent to amplification using a Snapback primer ((———)=wt; (—··—··—)=del; (— — —)=1:1; (------)=1:10; (········)=1:50; (—·—·—)=1:100; (········)=1:1000; (—··—··—)=1:5000; (— — —)=1:10000).

In this example, due to the deletion, there is substantial separation of the melting peaks and the annealing and extension temperatures used are both below that of virtually the entire wild type peak. As seen in FIG. 23, the EGFR exon 19 deletion E476-A750 to wild type DNA ratios of 1:1000 (mutant is the rare allele) are easily distinguishable from wild type, and even a ratio of 1:10000 can be distinguished from wild type by Snapback primer enrichment PCR.

Example 9. Methods for Determining Allele Fractions

When the PCR products are melted in the presence of DNA dyes, the measured dependence of raw fluorescence R(T) on temperature T includes two primary components. For a saturating, intercalating (high-resolution) dye, M(T) is closely proportional to the total quantity of DNA that is in its double stranded state, dsDNA, at temperature T. The remainder of the raw fluorescence, B(T), illustratively may be modeled by an exponential decay, particularly in the temperature regimes of current interest, i.e., those in which short oligonucleotide (unlabeled or Snapback) probes denature to their random coil form. After B(T) is removed, illustratively using the exponential background subtraction method (see U.S. Patent Application No. 2009-0222503, already incorporated by reference), and M(T) is scaled to normalized and background removed fluorescence F(T), illustratively in the range [0,1], the resulting curve is well approximated by the convex combination (i.e., a sum of nonnegative coefficients whose total sum is equal to 1) of two-state van 'tHoff thermodynamic melting curves. These models for B(T) and F(T) are both described in (Palais R and Wittwer C T, Methods in Enzymology 454:323-43, 2009).

In the illustrative embodiments presented herein, the model may be simplified considerably by the reduction in the number of species involved in the reactions in temperature regimes in which probes melt. Because probes such as unlabeled probes and Snapback primers are used, only two of the four possible duplexes that normally occur in natural bialleic diploid heterozygote and synthetic mixture amplicon melting are present in the melt curve in the probe temperature ranges.

From this perspective, F(T), is a convex combination $$F(T)=c_M F_M(T)+c_W F_W(T),$$

i.e., wherein the nonnegative allele fraction coefficients, $c_M$ and $c_W$ satisfy $c_M+c_W=1$.

By linearity of differentiation, the negative derivative curves of the properly normalized melting curves, D(T), is a convex combination of the similarly defined and normalized negative derivative curves corresponding to the two duplex species (illustratively, probe with WT and probe with MUT):

$$D(T)=-F'(T)=c_M D_M(T)+c_W D_W(T).$$

Therefore, as illustrated in FIG. 24, the negative derivative exhibits two peaks whose magnitudes are measured by any of several methods described below and reflect the relative proportion of the two species of product, presumably one that matches the probe (in the reverse complement sense), and another with a lower Tm that contains some mismatch. Herein, the former is referred to as WT and the latter as MUT, although it is understood that the perfect match may not always be the wild type allele and the allele with the mismatch may not always contain a mutation.

It is an important caveat that, for the problem of quantifying initial template fractions, that information regarding the relative efficiency of amplification is needed to assess original allele frequencies. As shown by multiple examples above, two samples with the same initial allele ratio could be amplified with varying levels of selective enrichment of a particular allele, to result in products that are measured with very different final allele ratios. Conversely, samples with distinct initial ratios can yield end products with the same ratio, illustratively if the appropriately different amplification protocols are used. In addition to the methods presented herein, methods such as standard curves derived from dilution series, as well as various theoretical methods, also may be used to convert from end product ratios to obtain initial template ratios in any particular reproducible amplification protocol (e.g., extension time, magnesium concentration.

In one illustrative method of calculating allele fractions, let $D_a(T)$ denote negative derivative of the normalized melting curve of a sample, where the subscript a represents either wild-type (w), homozygous mutant (m), or a fractional mixture of the two (f). If a Snapback primer (or unlabeled probe or other probe) matches the wild-type allele, the pure mutant negative derivative curve, $D_m(T)$, will exhibit a peak at a temperature $T_L$ and the pure wild-type negative derivative curve, $D_w(T)$, will exhibit a peak at a temperature $T_H$, with L for lower and H for higher as $T_L<T_H$. (It is understood that if the Snapback matches the mutant allele, then one may simply reverse the roles of $T_L$ and $T_H$ in what follows.) The negative derivative curve of a fractional mixture, $D_f(T)$, typically exhibits two peaks corresponding to melting of the snapback primer, one from the mismatched allele at a lower temperature $T_L$, and one from the matched allele at a higher temperature $T_H$. When the allele mixture proportions are far from equal, the minority allele exhibits a weak peak, or no peak at all, at the corresponding temperature. To take this into account, the mutant allele may be quantified using a weighted average of two estimates, $$F_m = w_L f(T_L) + w_H f(T_H),$$

each obtained at one of these melting temperatures. The weights for each temperature peak are determined by relative heights of the magnitudes of the mixed sample above that of the baselines of the unmixed samples that melt at the other temperature:

$$w_L = (D_f(T_L) - D_w(T_L))/(D_f(T_L) + D_f(T_H) - (D_w(T_L) + D_m(T_H))) \; (=a/(a+b) \text{ in FIG. 24})$$

and $$w_H = (D_f(T_H) - D_m(T_H))/(D_f(T_L) + D_f(T_H) - (D_w(T_L) + D_m(T_H))) \; (=b/(a+b) \text{ in FIG. 24}).$$

The weights are positive, their sum is 1, and they favor the more clearly defined peak.

The individual estimates $f(T_L)$, $f(T_H)$, may be obtained by linear interpolation of $D_f(T)$ between $D_w(T)$ and $D_m(T)$ at the two temperatures:

$$f(T_L) = (D_f(T_L) - D_w(T_L))/(D_m(T_L) - D_w(T_L)) \; (=a/d \text{ in FIG. 24})$$

and $$f(T_H) = (D_f(T_H) - D_w(T_H))/(D_m(T_H) - D_w(T_H)) \; (=c/e \text{ in FIG. 24}).$$

In the extreme case that the mixture is pure wild-type, such that $D_f = D_w$, we find that $f(T_L) = 0$ and $f(T_H) = 0$, and also $w_L = 0$ and $w_H = 1$, so that $F_m = 0$. In the extreme case that the mixture is pure mutant, such that $D_f = D_m$, we find that $f(T_L) = 1$ and $f(T_H) = 1$, and also $w_L = 0$ and $w_H = 1$, so that $F_m = w_L + w_H = 1$.

Altogether, in terms of the quantities in FIG. 24, $$F_m = a/(a+b)(a/d) + b/(a+b)(c/e) = (aae+bcd)/(de(a+b))$$

as discussed above in Example 6.

The choice of weighting may be used to provide some cancellation of nonlinear effects due to reannealing of probes from mismatched to matched templates and during melting. While this and other illustrative examples are presented using two alleles, it is understood that generalizations of these formulas to mixtures of more than two alleles is straightforward.

An alternate implementation is to use only the values associated with the higher peak, i.e., either a/d or c/e. In such an embodiment, it is understood that a and c are directly related, and, therefore, only one of these values is used. Another alternative is to include a natural heterozygous sample (HET) in the experimental protocol, and using amplification conditions designed to result in peaks of the product that are essentially equal according to the quantification procedures above, interpolate the sample peaks and those of WT and MUT to interpolate inversely the relative sample magnitude between 0.5 and 1 as was done above between 0 and 1. For example:

$$f(T_L) = 0.5 + 0.5(D_f(T_L) - D_h(T_L))/(D_m(T_L) - D_h(T_L))$$

$$f(T_H) = 0.5 - 0.5(D_f(T_L) - D_h(T_L))/(D_w(T_L) - D_h(T_L))$$

and estimate the mutant allele fraction using the HET and MUT peak at $T_L$ and the mutant allele fraction using the HET and WT peaks at $T_H$, respectively. As a check, if Df=Dh, both allele fractions are 0.5, if $D_f = D_w$, the mutant allele fraction is 0.0, and if $D_f = D_m$, the mutant allele fraction is 1.0. Illustratively, these values can then be weighted exactly the same as before.

Optionally, these values may be weighted according to the formula above, or full weight may be given to the value corresponding to the higher peak.

The quantities a,b,c,d,e can be determined in alternate manners. Instead of simply finding the temperature and corresponding value of the pointwise maximum value, the peaks may be fit using quadratic fitting and obtain the temperature and value of the highest point of the quadratic fit of the highest peak, and the value of the fits of the other curves at the same temperatures.

In addition, peak height may be replaced by the area between the corresponding curves over a temperature interval containing the peaks (illustratively using either method above of locating the peaks) whose width is illustratively determined by where the highest peak has decayed to 1/e (the natural exponential decay factor) times its maximum value.

Like the TMBSP quantification method in U.S. Patent Application No. 2003-0104438, the methods described below are thermodynamically based. However, the illustrative methods presented herein are non-iterative. Rather, the methods presented herein are fast and easy to implement, while retaining a high degree of accuracy. Also included is a method based on simple Levenberg-Marquardt best non-linear least-squares fit of D(T) by a convex combination of van 'tHoff derivative curves whose thermodynamic parameters ΔH and ΔS associated with each of the two duplex species (probe with WT and probe with MUT) are considered as variables in addition to the allele fractions. One may also set those values from the known sequences and nearest-neighbor parameters (including dedicated parameters derived using high-resolution melting under standard laboratory conditions) in which case the fit reduces to a two-parameter linear least-squares problem.

Thermodynamically based nonlinear least squares (TMBNLS): Obtain the best nonlinear least squares fit of D(T) with respect to six unknown parameters, $c_M$, $\Delta H_M$, $\Delta S_M$, $c_w$, $\Delta H_w$, $\Delta S_w$.

$$D(T) = c_M D(\Delta H_M, \Delta S_M) + c_W D(\Delta H_W, \Delta S_W).$$

Here, D(ΔH, ΔS) is the negative derivative of the analytical van 'tHoff melting curve uniquely determined by the two parameters ΔH and ΔS and the particular experimental conditions. The fit is performed using the Levenberg-Marquardt algorithm.

Thermodynamically based least squares (TMBLS): Obtain the best linear least squares fit of D(T) with respect to two unknown parameters, $c_M$, $c_w$.

$$D(T) = c_M D(\Delta H_M, \Delta S_M) + c_W D(\Delta H_W, \Delta S_W)$$

Here, D(ΔH, ΔS) is the negative derivative of the analytical van 'tHoff melting curve uniquely determined by the two parameters ΔH and ΔS and the particular experimental conditions. The parameters $\Delta H_M$, $\Delta S_M$, $\Delta H_W$, $\Delta S_W$ are specified using nearest-neighbor summation, with known tetrad parameters obtained using high-resolution melting under standard laboratory conditions. The fit is performed using the normal equations for the 2×2 matrix system.

Although the invention has been described in detail with reference to preferred embodiments, variations and modifications exist within the scope and spirit of the invention as described and defined in the following claims.

We claim:

1. A kit for amplification and allele detection of a biological sample wherein the biological sample comprises a first allele and a second allele of a target nucleic acid, the first allele being present in a higher concentration than the second allele, the kit comprising:
- a thermostable polymerase lacking a 5' to 3' exonuclease activity, a ds DNA binding dye
- a pair of primers configured for amplification of the target nucleic acid in the biological sample, wherein the probe is configured to hybridize to the target nucleic acid and the probe has a first Tm when hybridized to the first allele and second Tm when hybridized to the second allele, wherein the first Tm is higher than the second Tm,
- an oligonucleotide probe, wherein the probe is a probe element attached to a 5' end of one primer of the pair of primers, and
- instructions for amplifying the target nucleic acid in the biological sample by thermal cycling between a denaturation temperature and an annealing temperature, wherein the annealing temperature is below the first Tm, and thermal cycling through an extension temperature between at least the annealing temperature and the denaturation temperature at a ramp rate of at least 4° C./sec.

2. The kit of claim 1, further comprising a buffer to provide a Mg++ concentration less than 2.0 mM when added to the biological sample.

3. The kit of claim 1, wherein the second allele is present in an allele fraction of 10% or less.

4. The kit of claim 1, wherein the second allele is present in an allele fraction of 5% or less.

5. The kit of claim 1, wherein the instructions further include instructions for detecting the preferentially amplified second allele through melting curve analysis of the probe and the amplified second allele.

6. The kit of claim 1, wherein the kit includes only one probe.

7. The kit of claim 1, wherein the instructions further include instructions for calculating allele fractions of the first allele and the second allele, wherein the calculating step comprises estimating the second allele fraction as $Fm=wLf(TL)+wHf(TH)$, where wL and wH are weights and f(TL) and f(TH) are individual estimates at each temperature peak calculated from standards of a homozygote of the first allele, a homozygote of the second allele, and a 50:50 mix of the first allele and second allele.

8. A kit for amplification and allele detection of a biological sample wherein the biological sample comprises a first allele and a second allele of a target nucleic acid, the first allele being present in a higher concentration than the second allele, comprising:
- a thermostable polymerase lacking a 5' to 3' exonuclease activity,
- a pair of primers configured for amplification of the target nucleic acid in the biological sample, wherein the probe is configured to hybridize to the target nucleic acid and the probe has a first Tm when hybridized to the first allele and second Tm when hybridized to the second allele, wherein the first Tm is higher than the second Tm,
- an oligonucleotide probe configured to hybridize to the target nucleic acid without being extended by the thermostable polymerase, wherein the probe is a probe element attached to a 5' end of one primer of the pair of primers, the probe having a first Tm when hybridized to the first allele and a second Tm when hybridized to the second allele, wherein the first Tm is higher than the second Tm,
- instructions for amplifying the target nucleic acid in the biological sample by thermal cycling between a denaturation temperature and an annealing temperature, wherein the annealing temperature is below the first Tm, and thermal cycling through an extension temperature between at least the annealing temperature and the denaturation temperature at a ramp rate of at least 4° C./sec, and for detecting the preferentially amplified second allele through melting curve analysis of the probe and the amplified second allele.

9. The kit of claim 8, wherein the kit includes only one probe.

10. The kit of claim 8, wherein the instructions further include instructions for calculating allele fractions of the first allele and the second allele, wherein the calculating step comprises estimating the second allele fraction as $Fm=wLf(TL)+wHf(TH)$, where wL and wH are weights and f(TL) and f(TH) are individual estimates at each temperature peak calculated from standards of a homozygote of the first allele, a homozygote of the second allele, and a 50:50 mix of the first allele and second allele.

* * * * *